US010038148B2

(12) United States Patent
Ingleson et al.

(10) Patent No.: US 10,038,148 B2
(45) Date of Patent: Jul. 31, 2018

(54) BORYLATED COMPOUNDS

(71) Applicant: The University of Manchester, Manchester (GB)

(72) Inventors: Michael James Ingleson, Manchester (GB); Michael Lewis Turner, Manchester (GB); Daniel Luke Crossley, Manchester (GB)

(73) Assignee: The University of Manchester, Manchester (GB)

( * ) Notice: Subject to any disclaimer, the term of this patent is extended or adjusted under 35 U.S.C. 154(b) by 0 days.

(21) Appl. No.: 15/318,177

(22) PCT Filed: Jun. 11, 2015

(86) PCT No.: PCT/GB2015/051726
§ 371 (c)(1),
(2) Date: Dec. 12, 2016

(87) PCT Pub. No.: WO2015/189627
PCT Pub. Date: Dec. 17, 2015

(65) Prior Publication Data
US 2017/0110660 A1    Apr. 20, 2017

(30) Foreign Application Priority Data

Jun. 13, 2014  (GB) .................................. 1410567.0

(51) Int. Cl.
*H01L 51/00* (2006.01)
*C07F 5/02* (2006.01)
*C09K 11/06* (2006.01)
*C08G 61/10* (2006.01)
*H01L 51/50* (2006.01)
*C08G 61/12* (2006.01)

(52) U.S. Cl.
CPC ............ *H01L 51/008* (2013.01); *C07F 5/027* (2013.01); *C08G 61/10* (2013.01); *C08G 61/126* (2013.01); *C09K 11/06* (2013.01); *H01L 51/0036* (2013.01); *H01L 51/0039* (2013.01); *H01L 51/0052* (2013.01); *H01L 51/0068* (2013.01); *H01L 51/0071* (2013.01); *C08G 2261/12* (2013.01); *C08G 2261/149* (2013.01); *C08G 2261/1412* (2013.01); *C08G 2261/316* (2013.01); *C08G 2261/3223* (2013.01); *C08G 2261/52* (2013.01); *C08G 2261/95* (2013.01); *C09K 2211/1011* (2013.01); *C09K 2211/1022* (2013.01); *C09K 2211/1037* (2013.01); *C09K 2211/1044* (2013.01); *C09K 2211/1051* (2013.01); *C09K 2211/1092* (2013.01); *C09K 2211/1483* (2013.01); *H01L 51/5004* (2013.01); *H01L 51/5012* (2013.01); *H01L 2251/552* (2013.01)

(58) Field of Classification Search
CPC . C07F 5/02; C07F 5/027; C08G 61/10; C08G 61/126; C08G 2261/12; C08G 2261/1412; C08G 2261/149; C08G 2261/316; C08G 2261/3223; C08G 2261/52; C08G 2261/95; C09K 11/06; C09K 2211/1011; C09K 2211/1022; C09K 2211/1037; C09K 2211/1044; C09K 2211/1051; C09K 2211/1092; C09K 2211/1483; H01L 51/0036; H01L 51/0039; H01L 51/0043; H01L 51/0052; H01L 51/0068; H01L 51/0071; H01L 51/0074; H01L 51/008; H01L 2251/552; H01L 51/5004; H01L 51/5012
See application file for complete search history.

(56) References Cited

FOREIGN PATENT DOCUMENTS

| CN | 102899027 A | 1/2013 |
|---|---|---|
| EP | 2233490 A1 | 9/2010 |
| WO | 2015189627 A1 | 12/2015 |

OTHER PUBLICATIONS

Ishida et al., "Synthesis of Azaaromatic Borane Intramolecular Complexes by Palladium-Catalyzed Reaction of Azaaromatic Halides with Alkynyl(triaryl)borates," Helvetica Chimica Acta, vol. 95, 2012, 2474-2480.*
PCT/GB2015/051726 International Search Report and Written Opinion dated Aug. 12, 2015; 4 pages.
GB 1410567.0 UKIPO Search Report dated Feb. 18, 2015; 3 pages.
Enders et al. Novel Reactivity of Ferrocene Derivatives toward Lewis Acids: Decomplexation with Boron Trichloride and Synthesis of a Triple-Decker-like Iron-Zinc Complex. Organometallics (2002). 21:3856-3859.
Ishida et al. Synthesis of Azaaromatic-Borane Intramolecular Complexes by Palladium-Catalyzed Reaction of Azaaromatic Halides with Alkynyl(triaryl)borates. Helvetica Chimica Acta (2012). 95:2474-2480.

* cited by examiner

*Primary Examiner* — Pancham Bakshi
*Assistant Examiner* — Mark R Luderer
(74) *Attorney, Agent, or Firm* — Linda B. Huber; Nixon Peabody LLP

(57) ABSTRACT

Borylated compounds are disclosed, as well as their methods of preparation and their applications. The disclosed borylated compounds are highly stable, and have reduced band gap properties, thereby making them attractive candidates for incorporation into semiconducting materials for use in a variety of electronic, optical or electro-optical devices or components.

23 Claims, 18 Drawing Sheets

Extinction coefficient = 20303 M⁻¹ cm⁻¹
$\lambda_{max}$ = 539 nm
Absorption Onset = 613 nm
Band-gap = 2.02 eV
Emission $\lambda_{max}$ = 707 nm R = $^n$octyl

BORYLATED COMPOUNDS

CROSS-REFERENCE TO RELATED APPLICATIONS

This application is a National Phase of International Application No. PCT/GB2015/051726 filed Jun. 11, 2015, which designated the U.S. and that International Application was published under PCT Article 21(2) in English. Both applications also include a claim of priority under 35 U.S.C. § 119(a) and § 365(b) to British patent application No. GB 1410567.0 filed Jun. 13, 2014, the entirety of which is hereby incorporated by reference.

INTRODUCTION

The present invention relates to borylated compounds, their methods of manufacture and their use in semiconducting materials.

BACKGROUND OF THE INVENTION

In recent years, a considerable effort has been made towards the synthesis of conjugated systems with low bandgaps[1]. A highly effective methodology for achieving low band gap materials is through the synthesis of donor-acceptor π-conjugated systems[2]. Donor-acceptor (D-A) π-conjugated systems contain alternating electron rich (donor) and electron deficient (acceptor) conjugated moieties incorporated into the main chain. The properties of such systems hold potential for application in organic field effect transistors (OFETs), organic light-emitting diodes (OLEDs) and photovoltaic cells (OPV)[3]. The synthetic flexibility of D-A polymers enables the modulation of the frontier orbital energy levels resulting in the ability to fine tune the material's properties[4]. A reduction in band gap can be achieved through enhancing the strength of donor and acceptor moieties as larger orbital interactions result in an increased double bond character and stabilisation of the quinoidal mesomer.[1] Whilst current donor-acceptor motifs are highly promising, there is still ongoing research into the modification of the donor and acceptor units to engineer materials that show ever improving performance.

One methodology is increasing the electron deficiency of the acceptor moiety by appending electron withdrawing groups, which reduces the band-gap by lowering the LUMO level[2]. Binding of a Lewis acid onto an acceptor moiety has been shown to be an effective way of significantly increasing the electron withdrawing power of the acceptor. This produces a considerable decrease in the energy of the LUMO, which is essential for developing high performance organic electronics with high electron affinities and mobilities[3].

Poverenov et. al.[4] recently demonstrated that benzothiadiazole (BT) containing D-A polymers could be doped by coordination of low amounts of a Lewis acid, which led to a dramatic increase in conductivity. However, the drawback of such Lewis acid binding strategies is that the resulting systems are highly sensitive, with the BT→Lewis acid dative bond being readily cleaved by both water and Lewis bases.

It is therefore desirable to develop stable D-A compounds having optimized conductivity characteristics.

The present invention was devised with the foregoing in mind.

SUMMARY OF THE INVENTION

According to a first aspect of the present invention there is provided a compound comprising one or more moieties of formulae (I)-(V) defined herein, wherein $R_1$, $R_2$, $R_3$, $R_4$, $\pi_a$, $\pi_b$ and $\pi_c$ are as defined herein.

According to a second aspect of the present invention there is provided a method of preparing a compound comprising one or more moieties of any of formulae (I)-(V) defined herein, the method comprising the steps of:

a) reacting a moiety of any of formulae (I')-(V') defined herein with a reagent $BX_3$, wherein X, $\pi_a$, $\pi_b$ and $\pi_c$ are as defined herein, b) reacting the product of step a) with a weak nucleophile either in the presence or absence of a halophilic Lewis acid: and c) performing one or more subsequent steps on the product of step b) to functionalise the boron atom with or more $R_1$, $R_2$, $R_3$ and $R_4$ groups as defined herein.

According to a further aspect of the present invention there is provided a method of preparing a compound comprising one or more moieties of any of formulae (I)-(V) defined herein, the method comprising the steps of:

a) reacting a moiety of any of formulae (I')-(V') defined herein with a reagent $BX_3$, wherein X, $\pi_a$, $\pi_b$ and $\pi_c$ are as defined herein, b) reacting the product of step a) with a weak nucleophile in the presence of a halophilic main group Lewis acid: and c) performing one or more subsequent steps on the product of step b) to functionalise the boron atom with or more $R_1$, $R_2$, $R_3$ and $R_4$ groups as defined herein.

According to a third aspect of the present invention there is provided a method of preparing a compound comprising one or more moieties of formula (I) defined herein, the method comprising the steps of:

a) reacting a moiety of formula (I') defined herein with a reagent $BX_3$, wherein X, $\pi_a$, $\pi_b$ and $\pi_c$ are as defined herein, and b) performing one or more subsequent steps on the product of step a) to functionalise the boron atom with or more $R_1$, $R_2$, $R_3$ and $R_4$ groups as defined herein.

According to a fourth aspect of the present invention there is provided a semiconducting material comprising a compound as defined herein.

According to a fifth aspect of the present invention there is provided an electronic device comprising a semiconducting material as defined herein.

DETAILED DESCRIPTION OF THE INVENTION

Definitions

Unless stated otherwise, the following terms have the following meanings in this specification:

The term "alkyl" includes both straight and branched chain alkyl groups. References to individual alkyl groups such as "propyl" are specific for the straight chain version only and references to individual branched chain alkyl groups such as "isopropyl" are specific for the branched chain version only. For example, "(1-20C)alkyl" includes (1-4C)alkyl, (1-3C)alkyl, propyl, isopropyl and t-butyl. A similar convention applies to other radicals mentioned herein.

The terms "alkenyl" and "alkynyl" include both straight and branched chain alkenyl and alkynyl groups.

The term "hydrocarbyl" encompasses the definitions of "alkyl", "alkenyl" and "alkynyl".

The term "halo" refers to fluoro, chloro, bromo and iodo.

The term "fluoroalkyl" means an alkyl group as defined herein which is substituted with one or more fluoro atoms, e.g. —$CF_3$, or —$CH_2CF_3$ and the like. Suitably, a fluoroalkyl group is a trifluoro-substituted alkyl group.

The term "π-conjugated ring system" refers to conjugated aromatic ring system that may comprise one, two, three or four rings joined to form a π-conjugated ring system. In one embodiment, the π-conjugated ring system may be an aryl and/or heteroaromatic ring system comprising one, two or three fused aromatic or heteroaromatic rings. In another embodiment, the ring system may comprise a conjugated system comprising a central non-aromatic ring fused between two aromatic or heteroaromatic rings, provided the ring system overall remains conjugated.

The term "π-donor ring system" refers to an aromatic ring system having a π-electron rich character (i.e. having an electron density per aromatic nucleus that is greater than benzene). Exemplary π-donor ring systems are furan, thiophene, pyrrole, oxazole and imidazole.

The term "π-acceptor ring system" refers to an aromatic ring system having a π-electron deficient character (i.e. having an electron density per aromatic nucleus that is lower than benzene). Exemplary π-acceptor ring systems are benzothiadiazole, pyridine, pyrimidine and purine.

The term "aryl" is used herein to denote phenyl, naphthalene or anthracene ring. In an embodiment, an "aryl" is phenyl or naphthalene, and particularly is phenyl.

The term "heteroaryl" or "heteroaromatic" means an aromatic mono-, bi-, or tri-cyclic ring incorporating one or more (for example 1-4, particularly 1, 2 or 3) heteroatoms selected from N, O, S, Si or Se. Examples of heteroaryl groups are monocyclic, bicyclic and tricyclic groups containing from five to eighteen ring members. The heteroaryl group can be, for example, a 5- or 6-membered monocyclic ring, a 8-, 9- or 10-membered bicyclic ring or a 15-, 16-, 17- or 18-membered tricyclic ring. Suitably each ring in a bicyclic or tricyclic ring system comprises five or six ring atoms.

The term "heterocyclyl", "heterocyclic" or "heterocycle" means a non-aromatic saturated or partially saturated monocyclic, fused, bridged, or spiro bicyclic heterocyclic ring system(s). The term heterocyclyl includes both monovalent species and divalent species. Monocyclic heterocyclic rings contain from about 3 to 12 (suitably from 3 to 7) ring atoms, with from 1 to 5 (suitably 1, 2 or 3) heteroatoms selected from nitrogen, oxygen or sulfur in the ring. Bicyclic heterocycles contain from 7 to 17 member atoms, suitably 7 to 12 member atoms, in the ring. Bicyclic heterocycles contain from about 7 to about 17 ring atoms, suitably from 7 to 12 ring atoms. Bicyclic heterocyclic(s) rings may be fused, spiro, or bridged ring systems. As the skilled person would appreciate, any heterocycle may be linked to another group via any suitable atom, such as via a carbon or nitrogen atom.

The term "weak nucleophile" means any tertiary amine or phosphine that binds reversibly to $BX_3$, wherein X is Cl or Br. Exemplary weak nucleophiles are 2,6-ditertbutyl pyridine, 2,4,6-tritertbutylpyridine, 2,6-dimethylpyridine, 2,6-dichloropyridine, di(isopropyl)ethylamine, N,N,4-trimethylaniline, tri(mesityl)phosphine, and diphenylmethylamine.

The term "halophilic main group Lewis acid" means any main group Lewis acid having an affinity for halide ions (including Cl and Br). Exemplary halophilic main group Lewis acids include $AlCl_3$, $AlBr_3$, $GaCl_3$, $GaBr_3$, $BBr_3$, and other main group Lewis acids having comparably high halide ion affinity. The skilled person will, however, appreciate that other, non-main group, Lewis Acids (e.g. $FeCl_3$) may also be used as part of the present invention.

Compounds of the Invention

As discussed herein before, in one aspect, the present invention provides compounds comprising one or more moieties of formulae (I)-(V):

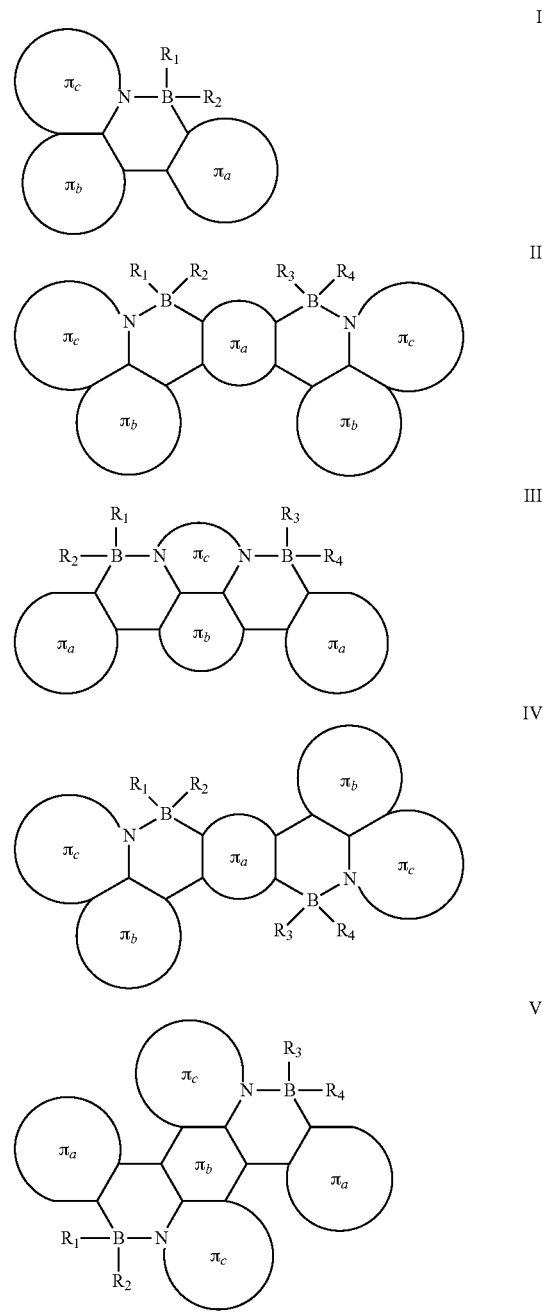

wherein:

$R_1$, $R_2$, $R_3$ and $R_4$ are each independently selected from hydrogen, fluoro, chloro, bromo, substituted or unsubstituted (1-10C)alkyl, substituted or unsubstituted (2-10C)alkenyl, substituted or unsubstituted (2-10C)alkynyl, substituted or unsubstituted aryl, substituted or unsubstituted heteroaryl, substituted or unsubstituted amino, substituted or unsubstituted (1-10C)alkoxy, substituted or unsubstituted arylalkoxy, and hydroxyl;

each $\pi_a$ independently represents a π-conjugated π-donor ring system formed from one, two, three or four 6-membered aryl or 5 to 6-membered heteroaryl rings;

each $\pi_b$ independently represents a π-conjugated 6-membered aryl or 5-6 membered heteroaryl ring;

each $\pi_n$ independently represents a π-conjugated 5-6 membered heteroaryl ring, which when taken in combination with $\pi_b$, forms a π-acceptor ring system;

wherein:
any or all of the rings forming $\pi_a$, $\pi_b$ and $\pi_c$ may be independently optionally substituted with one more ring substituents selected from halo, (1-20C)alkyl, (2-20C)alkenyl, (2-20C)alkynyl, aryl, heteroaryl, cycloalkyl, heterocyclyl, carboxyl, phosphoryl, sulfonyl, hydroxyl, (1-20C)alkoxy, nitro, amino, mercapto, silyl, siloxy, azido, boronic acid group, sulfonic acid group, hydroxamic acid group, cyanoacrylate group, and dioxocyclobutenyl group having at least one functional group selected from the group consisting of a carboxyl, phosphoryl, sulfonyl, hydroxyl, alkoxy, nitro, amino, mercapto, silyl, siloxy, azido, boronic acid group, sulfonic acid group, hydroxamic acid group and cyanoacrylate group.

It has been found that the stability of coordinated Lewis acid systems can be enhanced by twinning N→B dative bond formation at the acceptor moiety with C—B bond formation at the donor moiety, in order to form a fused C—N chelated Lewis acid adduct. In addition to the significant lowering of the acceptor LUMO energy level by coordination of boron, borylation of the aromatic donor may raise the HOMO energy level due to the inductive effect of the 4-coordinate boron, thereby resulting in it being a better donor group. Hence, the HOMO-LUMO band gap is further reduced with respect to prior art compounds. Furthermore, once borylated, the donor and acceptor units are locked in a co-planar geometry, which results in better communication along the conjugated system and modifies the intermolecular packing of the oligomer/polymer. Enforcing a co-planar arrangement between the materials consecutive repeat units by preventing monomer twisting through the formation of irreversible linkages is advantageous as it maximizes the extended π-conjugation, which may also lead to a further lowering of the band-gap.

In addition to the advantages discussed above, metathesis of the B—X bond for B—$R_{1-4}$ significantly improves moisture stability, and in certain cases resulting in a further lowering of the LUMO level on the acceptor moiety as electron density is removed, thus resulting in a higher electron affinity.

Insofar as $R_1$, $R_2$, $R_3$ and $R_4$ are concerned, it will be appreciated by the skilled person that the term "substituted or unsubstituted" refers to any suitable substituent, providing it is chemically feasible. Suitable substituents include, for example, hydroxyl, (1-10C)alkyl, (2-10C)alkenyl, (2-10C)alkynyl, aryl, aryl(1-10C)alkyl, heteroaryl(1-10C)alkyl, perhaloaryl and fluorenyl (optionally additionally substituted with one or more substituents selected from hydroxyl, (1-10C)alkyl, (2-10C)alkenyl, (2-10C)alkynyl, aryl, aryl(1-10C)alkyl, heteroaryl(1-10C)alkyl, perhaloaryl and fluorenyl).

In an embodiment, any or all of the rings forming $\pi_a$, $\pi_b$ and $\pi_c$ may be independently optionally substituted with one more ring substituents selected from halo, (1-10C)alkyl, (2-10C)alkenyl, (2-10C)alkynyl, aryl, heteroaryl, cycloalkyl, heterocyclyl, carboxyl, phosphoryl, sulfonyl, hydroxyl, (1-10C)alkoxy, nitro, amino, mercapto, silyl, siloxy, azido, boronic acid group, sulfonic acid group, hydroxamic acid group, cyanoacrylate group, and dioxocyclobutenyl group having at least one functional group selected from the group consisting of a carboxyl, phosphoryl, sulfonyl, hydroxyl, alkoxy, nitro, amino, mercapto, silyl, siloxy, azido, boronic acid group, sulfonic acid group, hydroxamic acid group and cyanoacrylate group.

In an embodiment, any or all of the rings forming $\pi_a$, $\pi_b$ and $\pi_c$ may be independently optionally substituted with one more ring substituents selected from halo, (1-10C)alkyl, (2-10C)alkenyl, (2-10C)alkynyl, aryl, heteroaryl, cycloalkyl, heterocyclyl, carboxyl, hydroxyl, (1-10C)alkoxy and amino.

Suitably, any or all of the rings forming $\pi_a$, $\pi_b$ and $\pi_c$ may be independently optionally substituted with one more ring substituents selected from halo, (1-10C)alkyl, (2-10C)alkenyl, (2-10C)alkynyl, aryl, heteroaryl, cycloalkyl and heterocyclyl.

More suitably, any or all of the rings forming $\pi_a$ may be independently optionally substituted with one or more ring substituents selected from bromo or (1-8C)alkyl (e.g. methyl or octyl).

In another embodiment, $R_1$, $R_2$, $R_3$ and $R_4$ are each independently selected from hydrogen, fluoro, chloro, bromo, substituted or unsubstituted (1-10C)alkyl, substituted or unsubstituted (2-10C)alkenyl, substituted or unsubstituted (2-10C)alkynyl, substituted or unsubstituted aryl, substituted or unsubstituted heteroaryl, and hydroxyl.

Suitably, $R_1$, $R_2$, $R_3$ and $R_4$ are each independently selected from hydrogen, fluoro, chloro, bromo, substituted or unsubstituted (1-10C)alkyl (e.g. fluoroalkyl), substituted or unsubstituted aryl, substituted or unsubstituted heteroaryl, and hydroxyl. Exemplary $R_1$, $R_2$, $R_3$ and $R_4$ substituents include methyl, n-octyl, phenyl, p-tolyl, perfluorophenyl, substituted or unsubstituted fluorene, 2-octylthiophene and hydroxyl.

More suitably, $R_1$, $R_2$, $R_3$ and $R_4$ are each independently selected from hydrogen, fluoro, substituted or unsubstituted (1-10C)alkyl (e.g. fluoroalkyl), substituted or unsubstituted aryl, substituted or unsubstituted heteroaryl, and hydroxyl. Exemplary $R_1$, $R_2$, $R_3$ and $R_4$ substituents include methyl, n-octyl, phenyl, p-tolyl, perfluorophenyl, substituted or unsubstituted fluorene, 2-octylthiophene and hydroxyl.

In another embodiment, each $\pi_b$ is independently a 6 membered phenyl ring or a 6 membered heteroaryl ring containing 1, 2 or 3 nitrogen atoms; and each $\pi_c$ is independently a 5-6 membered heteroaryl ring containing 1, 2 or 3 heteroatoms selected from N, O, Se or S; wherein each $\pi_b$ and $\pi_c$ is independently optionally substituted with one or more ring substituents as defined herein. Suitably, each $\pi_b$ is a 6 membered aryl ring.

In another embodiment, when taken in combination, each $\pi_b$ and r, independently forms a moiety $\pi_{bc}$ selected from:

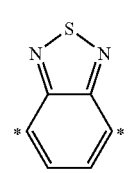

$\pi_{bc1}$

$\pi_{bc2}$

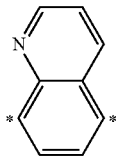

$\pi_{bc3}$

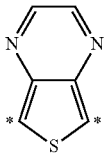

$\pi_{bc4}$ wherein moieties $\pi_{bc1}$, $\pi_{bc2}$, $\pi_{bc3}$ and $\pi_{bc4}$ are directly bonded to 1 or 2 boron atoms via either or both nitrogen atoms respectively;

moieties $\pi_{bc1}$, $\pi_{bc2}$, $\pi_{bc3}$ and $\pi_{bc4}$ are directly bonded to 1 or 2 $\pi_a$ moieties via either or both C*; and moieties $\pi_{bc1}$, $\pi_{bc2}$, $\pi_{bc3}$ and $\pi_{bc4}$ are each independently optionally substituted with one or more ring substituents as defined herein.

It will be understood that for $\pi_{bc}$ moieties having two N atoms, either or both of the N atoms may form a dative bond to boron. It will be further understood that where the $\pi_{bc}$ moieties are linked by C* to only one $\pi_a$ moiety, such $\pi_{bc}$ moieties may (i) be substituted at the other C* by any ring substituent defined herein, or (ii) be linked at the other C* to another moiety of formulae (I) to (V) in any manner described herein.

Suitably, when taken in combination, each $\pi_b$ and $\pi_c$ independently forms a moiety $\pi_{bc}$ selected from:

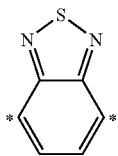

$\pi_{bc1}$

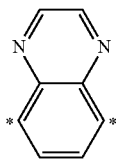

$\pi_{bc2}$

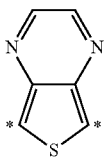

$\pi_{bc4}$ wherein moieties $\pi_{bc1}$, $\pi_{bc2}$ and $\pi_{bc4}$ are each independently optionally substituted with one or more ring substituents as defined herein.

More suitably, when taken in combination, each $\pi_b$ and $\pi_c$ independently forms the moiety $\pi_{bc1}$ shown below:

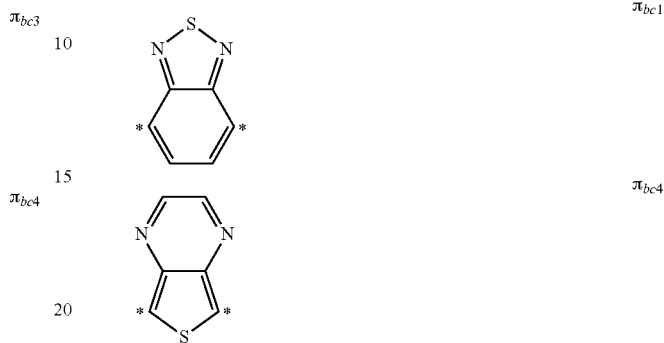

wherein each of moieties $\pi_{bc1}$ and $\pi_{bc4}$ are independently optionally substituted with one or more ring substituents as defined herein.

More suitably, when taken in combination, each $\pi_b$ and $\pi_c$ independently forms the moiety $\pi_{bc1}$ shown below:

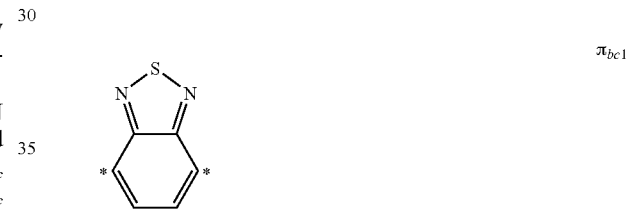

wherein each moiety $\pi_{bc1}$ is independently optionally substituted with one or more ring substituents as defined herein.

In another embodiment, each $\pi_a$ is independently formed from one, two or three 6-membered aryl or 5 to 6-membered heteroaryl rings, and wherein any or all of the rings are optionally substituted with one or more ring substituents as defined herein.

Suitably, each $\pi_a$ is a moiety independently selected from:

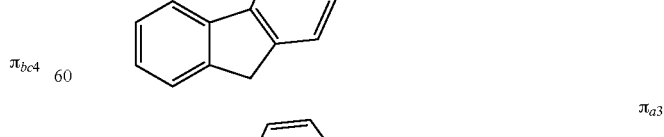

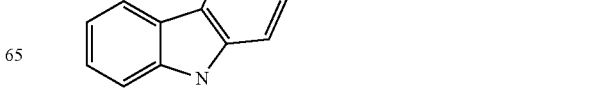

-continued

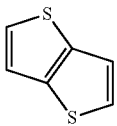
$\pi_{a4}$

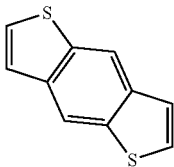
$\pi_{a5}$

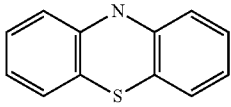
$\pi_{a6}$ wherein moieties $\pi_{a1}$, $\pi_{a2}$, $\pi_{a3}$, $\pi_{a4}$, $\pi_{a5}$ and $\pi_{a6}$ are independently optionally substituted with one or more ring substituents as defined herein.

More suitably, each $\pi_a$ is a moiety independently selected from:

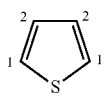
$\pi_{a1}$

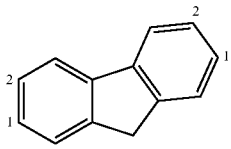
$\pi_{a2}$

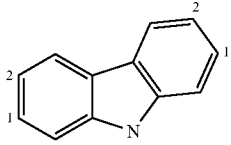
$\pi_{a3}$

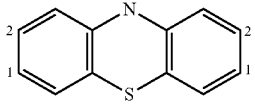
$\pi_{a6}$ wherein
i) moieties $\pi_{a1}$, $\pi_{a2}$, $\pi_{a3}$ and $\pi_{a6}$ are directly bonded to 1 or 2 $\pi_b$ moieties via either or both of C1 respectively; and
moieties $\pi_{a1}$, $\pi_{a2}$, $\pi_{a3}$ and $\pi_{a6}$ are directly bonded to 1 or 2 boron atoms via either or both of C2 respectively;
or
ii) moieties $\pi_{a1}$, $\pi_{a2}$, $\pi_{a3}$ and $\pi_{a6}$ are directly bonded to 1 or 2 $\pi_b$ moieties via either or both of C2 respectively; and
moieties $\pi_{a1}$, $\pi_{a2}$, $\pi_{a3}$ and $\pi_{a6}$ are directly bonded to 1 or 2 boron atoms via either or both of C1 respectively;
and
moieties $\pi_{a1}$, $\pi_{a2}$, $\pi_{a3}$ and $\pi_{a6}$ are independently optionally substituted with one or more ring substituents as defined herein.

In an embodiment, each $\pi_a$ is a moiety independently selected from:

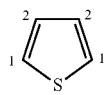
$\pi_{a1}$

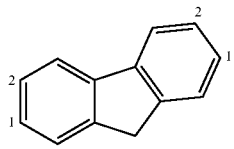
$\pi_{a2}$

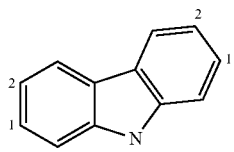
$\pi_{a3}$

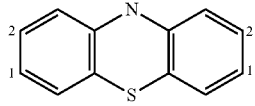
$\pi_{a6}$ wherein
moieties $\pi_{a1}$, $\pi_{a2}$, $\pi_{a3}$ and $\pi_{a6}$ are directly bonded to 1 or 2 $\pi_b$ moieties via either or both of C1 respectively;
moieties $\pi_{a1}$, $\pi_{a2}$, $\pi_{a3}$ and $\pi_{a6}$ are directly bonded to 1 or 2 boron atoms via either or both of C2 respectively; and
moieties $\pi_{a1}$, $\pi_{a2}$, $\pi_{a3}$ and $\pi_{a6}$ are independently optionally substituted with one or more ring substituents as defined herein.

It will be understood that moieties $\pi_{a1}$, $\pi_{a2}$, $\pi_{a3}$ and $\pi_{a6}$ may be independently optionally substituted at any available site with one or more ring substituents as defined herein. Hence, where a moiety $\pi_{a1}$, $\pi_{a2}$, $\pi_{a3}$ and $\pi_{a6}$ is bonded to only one boron atom (via one C2) and only one $\pi_b$ moiety (via one C1), the remaining C1 and C2 are freely substitutable. It will also be understood that the N atoms in $\pi_{a3}$ and $\pi_{a6}$ are bonded to a H atom, or any other substituent discussed herein in respect of $\pi_a$ groups. It will be further understood that moieties $\pi_{a1}$, $\pi_{a2}$, $\pi_{a3}$ and $\pi_{a6}$ may be linked at any available site, either directly or indirectly, to another moiety of formula (I) to (V) in any manner described herein.

In another embodiment, the compound comprises one or more moieties selected from:

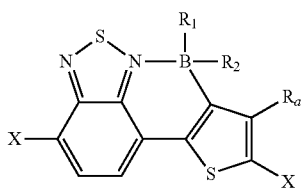

-continued

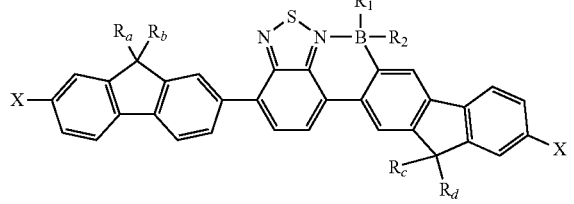

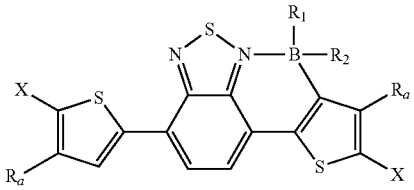

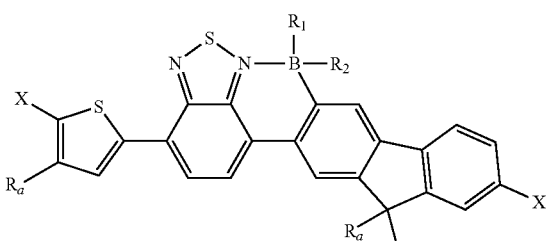

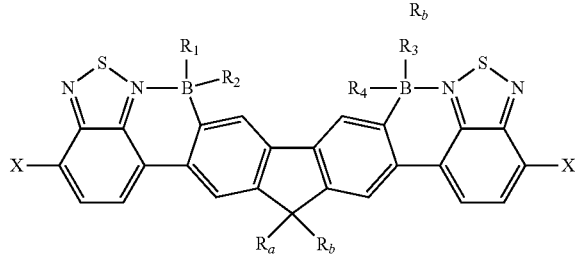

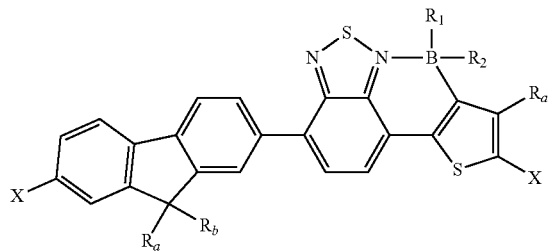

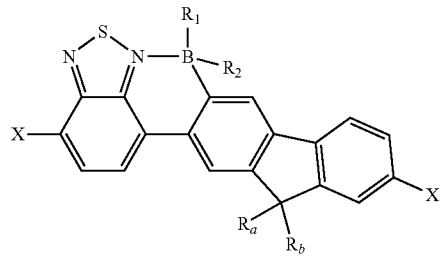

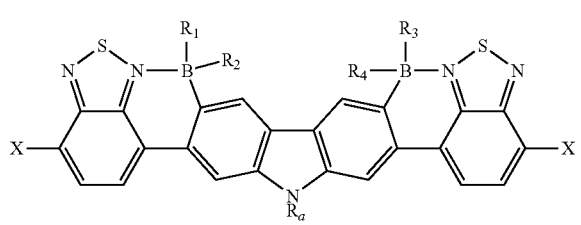

-continued

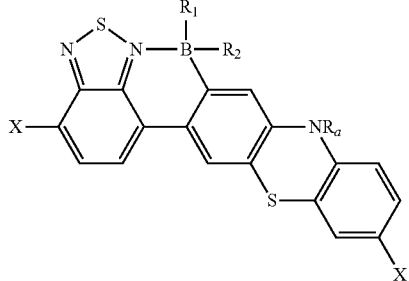

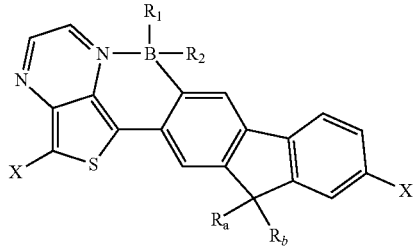

wherein $R_1$, $R_2$, $R_3$ and $R_4$ are independently as defined herein;

$R_a$, $R_b$, $R_c$ and $R_d$ are independently selected from hydrogen, (1-20C)alkyl, (2-20C)alkenyl and (2-20C)alkynyl; and each X is hydrogen, or is independently represented by:
  (i) bromo, (1-10C)alkyl, (2-10C)alkenyl or (2-10C)alkynyl; or
  (ii) another moiety having one of the structural formulae defined above.

In an embodiment, $R_1$, $R_2$, $R_3$ and $R_4$ are independently as defined herein;

$R_a$, $R_b$, $R_c$ and $R_d$ are independently selected from hydrogen, (1-10C)alkyl, (2-10C)alkenyl and (2-10C)alkynyl; and each X is hydrogen, or is independently represented by:
  (i) bromo, (1-10C)alkyl, (2-10C)alkenyl or (2-10C)alkynyl; or
  (ii) another moiety having one of the structural formulae defined above.

Suitably, $R_1$, $R_2$, $R_3$ and $R_4$ are each independently selected from hydrogen, fluoro, chloro, bromo, substituted or unsubstituted (1-10C)alkyl, substituted or unsubstituted aryl, substituted or unsubstituted heteroaryl, and hydroxyl; $R_a$, $R_b$, $R_c$ and $R_d$ are independently selected from hydrogen and (1-10C)alkyl; and each X is hydrogen, or is independently represented by:
  (i) bromo or (1-10C)alkyl; or
  (ii) another moiety having one of the structural formulae defined herein.

More suitably, $R_1$, $R_2$, $R_3$ and $R_4$ are each independently selected from methyl, n-octyl, phenyl, p-tolyl, perfluorophenyl, substituted or unsubstituted fluorene, 2-octylthiophene, hydroxyl, fluoro, chloro and bromo; $R_a$, $R_b$, $R_c$ and $R_d$ are independently selected from hydrogen and (1-10C)alkyl; and each X is hydrogen, or is independently represented by:
  (i) bromo or (1-10C)alkyl; or
  (ii) another moiety having one of the structural formulae defined herein.

More suitably, $R_1$, $R_2$, $R_3$ and $R_4$ are each independently selected from methyl, n-octyl, phenyl, p-tolyl, perfluorophenyl, substituted or unsubstituted fluorene, 2-octylthiophene, hydroxyl, fluoro; $R_a$, $R_b$, $R_c$ and $R_d$ are independently selected from hydrogen and (1-10C)alkyl; and each X is hydrogen, or is independently represented by:

(i) bromo or (1-10C)alkyl; or
(ii) another moiety having one of the structural formulae defined herein.

In another embodiment, the compound comprises two or more moieties of formulae (I)-(V), wherein the two or more moieties are linked by a direct bond, or by any suitable π-conjugated linker or linkers, $\pi_L$. Any suitable π-conjugated linker may be used. Suitable π-conjugated linkers ($\pi_L$) include the following:

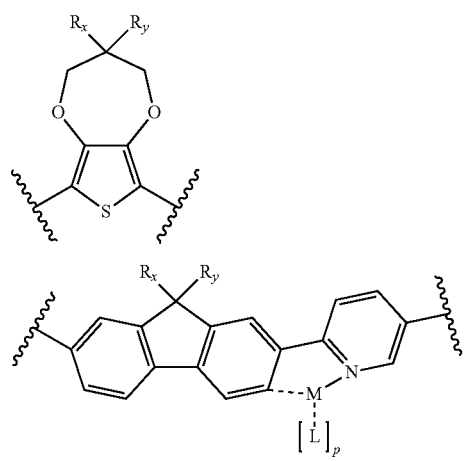
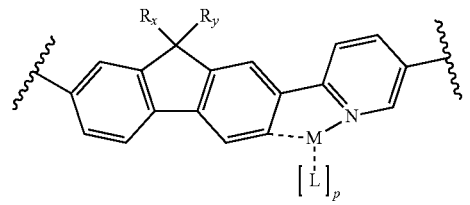
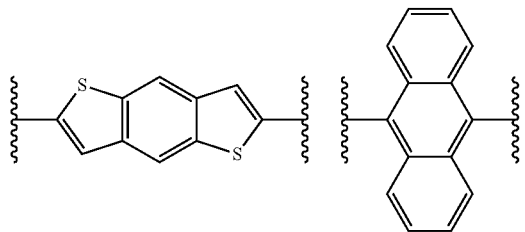
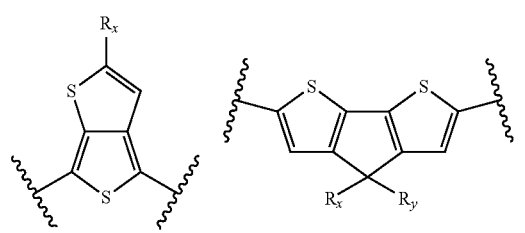
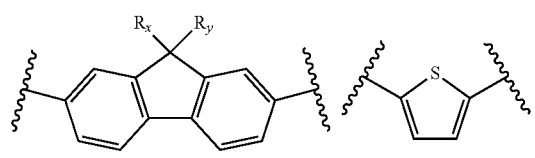
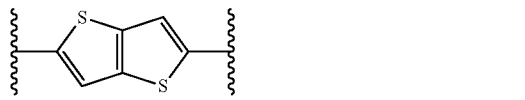
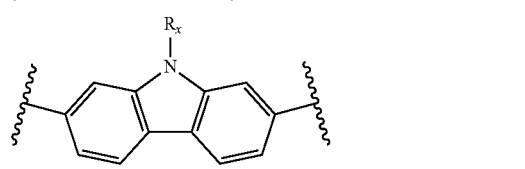

-continued

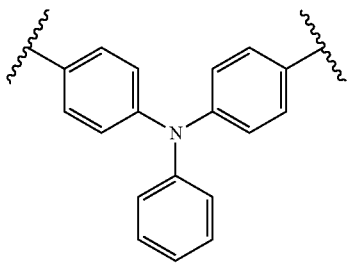
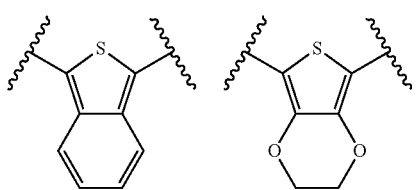
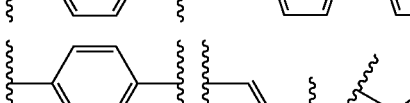
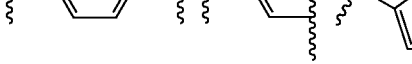
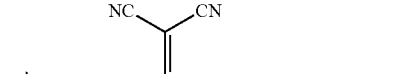
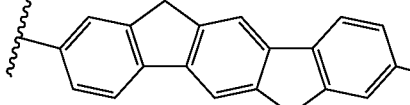
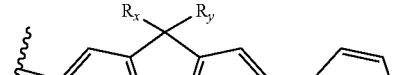
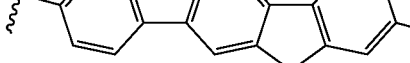

-continued

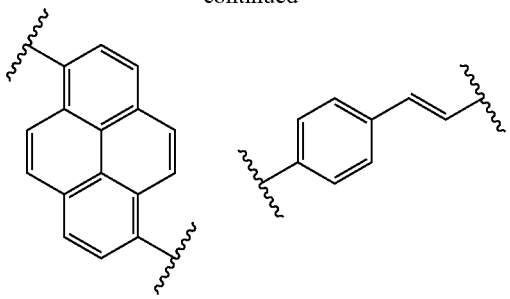

wherein
Rx and $R_y$ are each independently a group:

—$X^1$-$Q^1$ wherein
$X^1$ is selected from the group consisting of absent, (1-30C)alkylene, (2-30C)alkenylene, (2-30C)alkynylene, —[(CH$_2$)$_2$—O]$_n$— or —[O—(CH$_2$)$_2$]$_n$— (wherein n is 1 to 30), and
$Q^1$ is a terminal group selected from hydrogen, methyl, hydroxyl, carboxy, amino, —C=CH$_2$ or —C≡CH;
M is a metal selected from Ir, Pt, Rh, Re, Ru, Os, Cr, Cu, Pd and Au;
L is a ligand independently selected from the group consisting of halo, (1-30C)hydrocarbyl optionally comprising one or more heteroatoms selected from N, O, S, Si or P, or an aryl or heteroaryl group optionally substituted with one or more substituents selected from (1-4C)alkyl, halo, aryl or heteroaryl; and
p is 1 to 4.

A particularly suitable π-conjugated linker is:

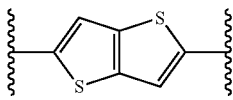 [SMILES: *c1cc2sc(*)cc2s1]

In embodiments where the compound comprises two moieties of formulae (I)-(V) that are linked together, the compound may comprise any of the following arrangements:
(I)-(I); (I)-(II); (I)-(III); (I)-(IV); (I)-(V); (II)-(I); (II)-(II); (II)-(III); (II)-(IV); (II)-(V); (III)-(I); (III)-(II); (III)-(III); (III)-(IV); (III)-(V); (IV)-(I); (IV)-(II); (IV)-(III); (IV)-(IV); (IV)-(V); (V)-(I); (V)-(II); (V)-(III); (V)-(IV); (V)-(V);
(I)-$\pi_L$-(I); (I)-$\pi_L$-(II); (I)-$\pi_L$-(III); (I)-$\pi_L$-(IV); (I)-$\pi_L$-(V); (II)-$\pi_L$-(I), (II)-$\pi_L$-(II), (II)-$\pi_L$-(III); (II)-$\pi_L$-(IV); (II)-$\pi_L$-(V); (III)-$\pi_L$-(I); (III)-$\pi_L$-(II); (III)-$\pi_L$-(III); (III)-$\pi_L$-(IV); (III)-$\pi_L$-(V); (IV)-$\pi_L$-(I); (IV)-$\pi_L$-(II); (IV)-$\pi_L$-(III); (IV)-$\pi_L$-(IV); (IV)-$\pi_L$-(V); (V)-$\pi_L$-(I); (V)-$\pi_L$-(II); (V)-$\pi_L$-(III); (V)-$\pi_L$-(IV); or (V)-$\pi_L$-(V).

For the avoidance of doubt, having regard to the notation used above, "(I)-(I)" means a moiety of formula (I) is bonded to another moiety of formula (I) by a direct bond. Hence, "(I)-(II)" denotes a moiety of formula (I) directly bonded to a moiety of formula (II). Similarly, the notation "(I)-$\pi_L$-(I)" means a moiety of formula (I) is bonded to another moiety of formula (I) by one or more π-conjugated linker, $\pi_L$, as defined herein. Hence "(I)-$\pi_L$-(II)" denotes a moiety of formula (I) bonded to a moiety of formula (II) by one or more π-conjugated linker, $\pi_L$, as defined herein.

A particularly suitable compound has the structure:

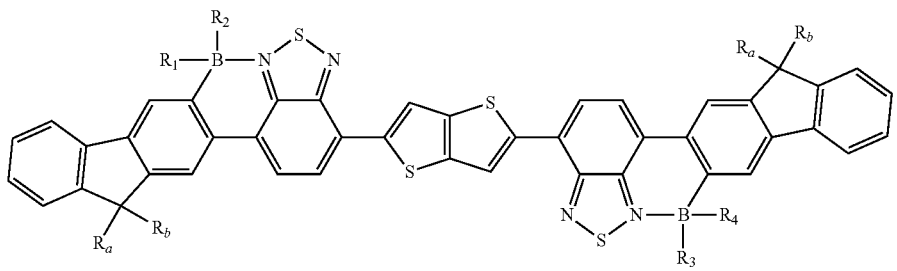

wherein $R_1$, $R_2$, $R_3$, $R_4$, $R_a$ and $R_b$ are as defined herein.

It will be understood that third and successive moieties of formulae (I)-(V) may be directly linked to the linked moieties, or linked via one or more $\pi_L$.

In another embodiment, the compound is a polymer or oligomer comprising two or more moieties of formulae (I)-(V) defined herein, each of the moieties representing a monomer. It will be understood that the polymer may comprise identical (i.e. a homopolymer) or different (i.e. a copolymer) monomers represented by formulae (I)-(V), each of which may be directly linked, or linked by one or more π-conjugated linker, $\pi_L$, defined herein. When the polymer or oligomer comprises a plurality of different monomers, the sequence of the monomers may be random or ordered (i.e. a block copolymer).

In one embodiment, the compound is a polymer, co-polymer or oligomer comprising one of the following monomeric moieties, where in the average percentage of the moieties of formulae (I)-(V) defined herein in the polymer chain ranges from >0% to ≤100%:

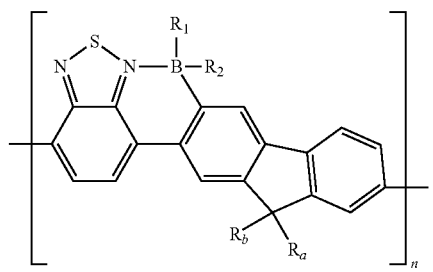

-continued

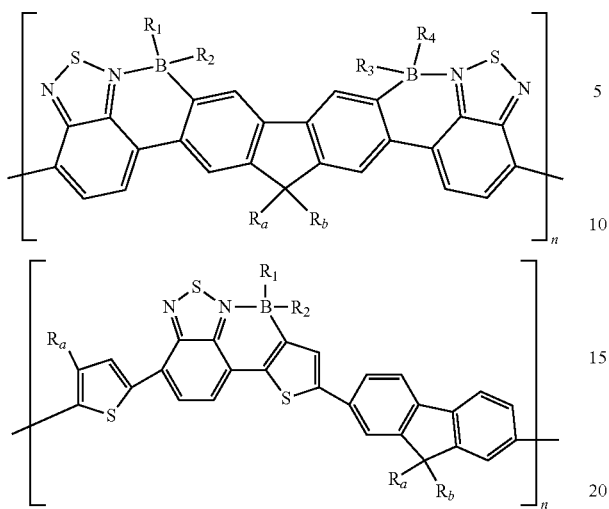

wherein $R_1$, $R_2$, $R_3$, $R_4$, $R_a$ and $R_b$ are as defined herein.

Methods of the Invention

As discussed hereinbefore, in one aspect, the present invention provides a method of preparing a compound comprising one or more moieties of any of formulae (I)-(V) defined herein, the method comprising the steps of:

a) reacting a compound comprising one or more moieties of any of formulae (I')-(V') shown below with a reagent $BX_3$:

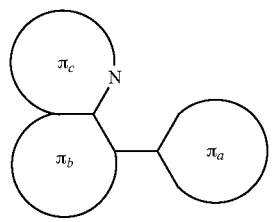
I'

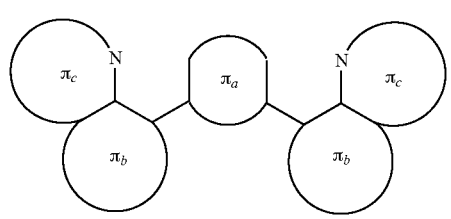
II'

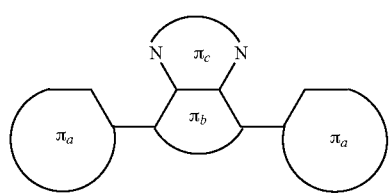
III'

-continued

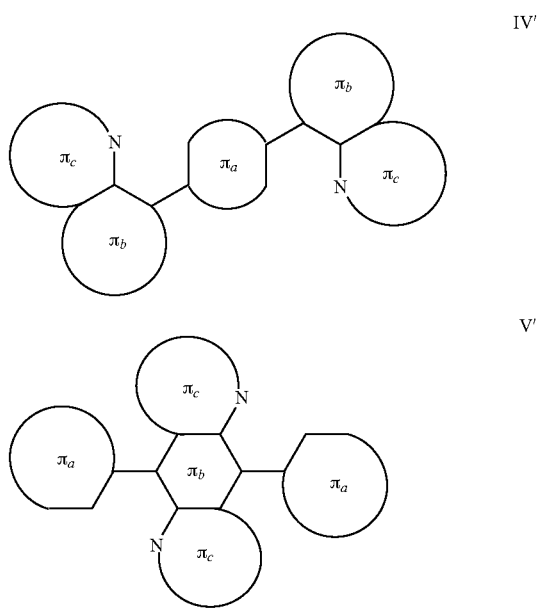

IV'

V' wherein moieties $\pi_a$, $\pi_b$ and $\pi_c$ are independently as defined herein; and each X is selected from Cl, Br, aryl or heteroaryl;

b) reacting the product of step a) with a weak nucleophile, in the presence or absence of a halophilic Lewis acid; and c) performing one or more subsequent steps on the product of step b) to functionalise the boron atom with or more $R_1$, $R_2$, $R_3$ and $R_4$ groups as defined herein.

In a further aspect, the present invention provides a method of preparing a compound comprising one or more moieties of any of formulae (I)-(V) defined herein, the method comprising the steps of:

a) reacting a compound comprising one or more moieties of any of formulae (I')-(V') shown below with a reagent $BX_3$:

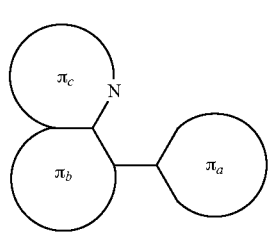
I'

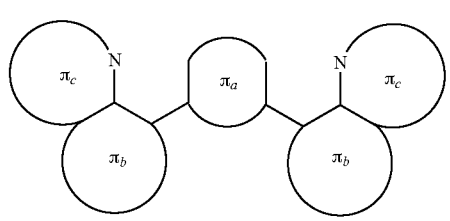
II'

-continued

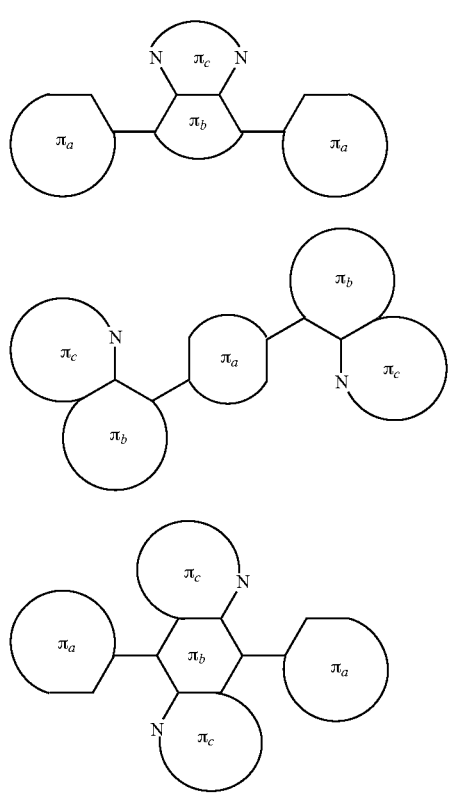

wherein
moieties $\pi_a$, $\pi_b$ and $\pi_c$ are independently as defined herein; and
X is selected from Cl or Br;
b) reacting the product of step a) with a weak nucleophile, in the presence of a halophilic main group Lewis acid; and
c) performing one or more subsequent steps on the product of step b) to functionalise the boron atom with or more $R_1$, $R_2$, $R_3$ and $R_4$ groups as defined herein.

In an embodiment, in step a), the compound comprising one or more moieties of formulae (I)'-(V)' is a polymer or oligomer.

In another embodiment, the compound comprising one or more moieties of any of formulae (I)-(V) defined herein is a compound consisting of one of the moieties of any of formulae (I)-(V) defined herein, and the method comprises an additional step or steps to formulate the compound into a polymer or oligomer.

In an embodiment, the weak nucleophile is selected from the group consisting of 2,6-ditertbutyl pyridine, 2,4,6-tritertbutylpyridine, 2,6-dimethylpyridine, 2,6-dichloropyridine, di(isopropyl)ethylamine, N,N,4-trimethylaniline, tri(mesityl)phosphine, and diphenylmethylamine.

Suitably, the weak nucleophile is 2,4,6-tri-tert-butylpyridine.

In another embodiment, the halophilic Lewis acid is selected from the group consisting of $AlCl_3$, $AlBr_3$, $GaCl_3$, $GaBr_3$, $BBr_3$ and $FeCl_3$. Suitably, the Lewis acid is selected from $AlCl_3$, $AlBr_3$, $GaCl_3$, $GaBr_3$ and $BBr_3$.

More suitably, the halophilic main group Lewis acid is $AlCl_3$.

In another embodiment, step c) comprises reacting the product of step b) with a reagent selected from the group consisting of $Al(Z)_3$, $Zn(Z)_2$, or $Sn(nBu)_3(Z)$, wherein each Z is independently represented by one or more $R_1$, $R_2$, $R_3$ or $R_4$ defined herein.

Suitably, step c) comprises reacting the product of step b) with a reagent selected from the group consisting of $Al(Z)_3$, $Zn(Z)_2$ or $Sn(nBu)_3(Z)$, wherein each Z is independently represented methyl, phenyl, p-tolyl or $C_6F_5$.

In another embodiment, prior to step c) the method further comprises the step of reacting the product of step b) with a chloride donating reagent. Suitably, the chloride donating reagent is a compound $NR_4Cl$, wherein R is (1-5C)alkyl, or a compound $PR_4Cl$, wherein R is (1-5C)alkyl or aryl. More suitably, the chloride donating reagent is $NMe_4Cl$ or $NBu_4Cl$.

In another embodiment, the method further comprises a step d) of linking the product of step c) with one or more other moieties of formulae (I)-(V) defined herein. Step d) may comprise directly linking the product of step c) with one or more other moieties of formulae (I)-(V), or linking the product of step c) with one or more other moieties of formulae (I)-(V) via one or more $\pi_L$ defined herein.

As discussed hereinbefore, in another aspect, the present invention provides a method of preparing a compound comprising one or more moieties of formula (I) defined herein, the method comprising the steps of:
a) reacting a compound comprising one or more moieties of formula (I') shown below with a reagent $BX_3$:

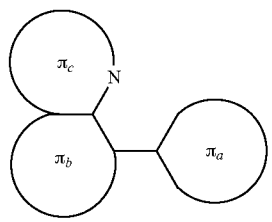

wherein
moieties $\pi_a$, $\pi_b$ and $\pi_c$ are independently as defined herein; and
X is selected from
i) Cl, Br, aryl or heteroaryl; or
ii) Cl or Br;
and
b) performing one or more subsequent steps on the product of step b) to functionalise the boron atom with or more $R_1$, $R_2$, $R_3$ and $R_4$ groups as defined herein.

In addition to affording moieties of formula (I), the above method may also be used to synthesise certain compounds comprising moieties of formulae (II)-(V) defined herein. One such compound is compound 32, described herein.

In one embodiment, the method further comprises a step c) of linking the product of step b) with one or more other moieties of formulae (I)-(V) defined herein. Step c) may comprise directly linking the product of step b) with one or more other moieties of formulae (I)-(V), or linking the product of step b) with one or more other moieties of formulae (I)-(V) via one or more $\pi_L$ defined herein.

In another embodiment, step b) comprises reacting the product of step a) with a reagent selected from the group consisting of $Al(Z)_3$, $Zn(Z)_2$ or $Sn(nBu)_3(Z)$, wherein each Z is independently represented by one or more $R_1$, $R_2$, $R_3$ or $R_4$ defined herein.

Suitably, step b) comprises reacting the product of step a) with a reagent selected from the group consisting of Al(Z)$_3$, Zn(Z)$_2$ or Sn(nBu)$_3$(Z), wherein each Z is independently represented methyl, phenyl, p-tolyl or C$_6$F$_5$.

Applications of the Invention

As discussed hereinbefore, in one aspect, the present invention provides a semiconducting material comprising a compound as defined herein.

In one embodiment, the semiconducting material comprises a compound as defined herein, wherein the compound is a polymer or an oligomer.

The present invention also provides an electronic, optical or electro-optical component or device comprising a semiconducting material as defined herein.

The novel C,N-chelated borane structures disclosed herein are a new member of a large family of tetracoordinate organoboron compounds that are used for the construction of highly emissive materials. In these materials the boron centre acts as a light atom rigidifying unit that decreases non-radiative relaxation processes and results in large quantum yields. Thus, compounds of this family have found widespread application in numerous electronic and optical components and devices, attributable in part to their intense luminescence and high carrier mobility.

Exemplary electronic, optical or electro-optical components or devices include organic field effect transistors (OFET), thin film transistors (TFT), components of integrated circuitry (IC), radio frequency identification (RFID) tags, organic light emitting diodes (OLED), electroluminescence displays, flat panel displays, backlights, photodetectors, sensors, logic circuits, memory elements, capacitors, photovoltaic (PV) cells, photoconductors, and electrophotographic elements.

EXAMPLES

One or more examples of the invention will now be described, by way of illustrations only, with reference to the accompanying figures, in which.

Figure 6:
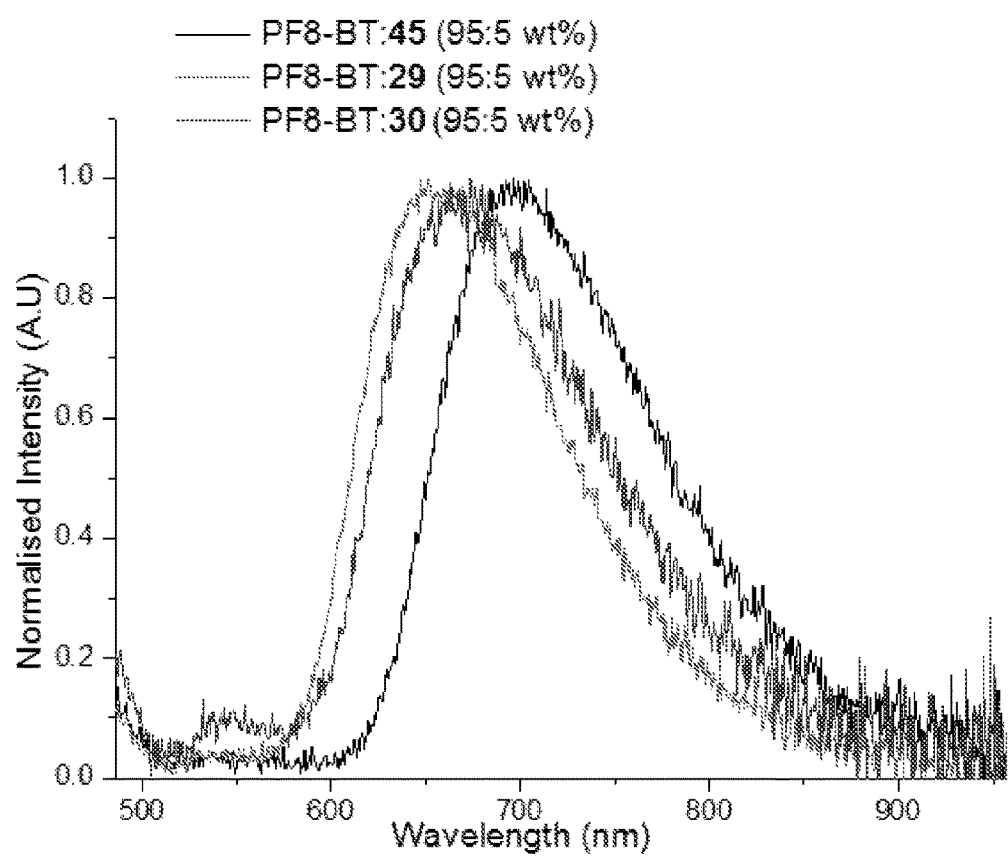

FIG. 6 solid state photoluminescence spectra of thin films from a 5 wt % mixture of borylated compounds 45, 29 and 30 dispersed in PF8-BT polymer (poly(9,9-dioctylfluorene-alt-benzothiadiazole) spin coated from toluene, excited at 468 nm.

Figure 7:
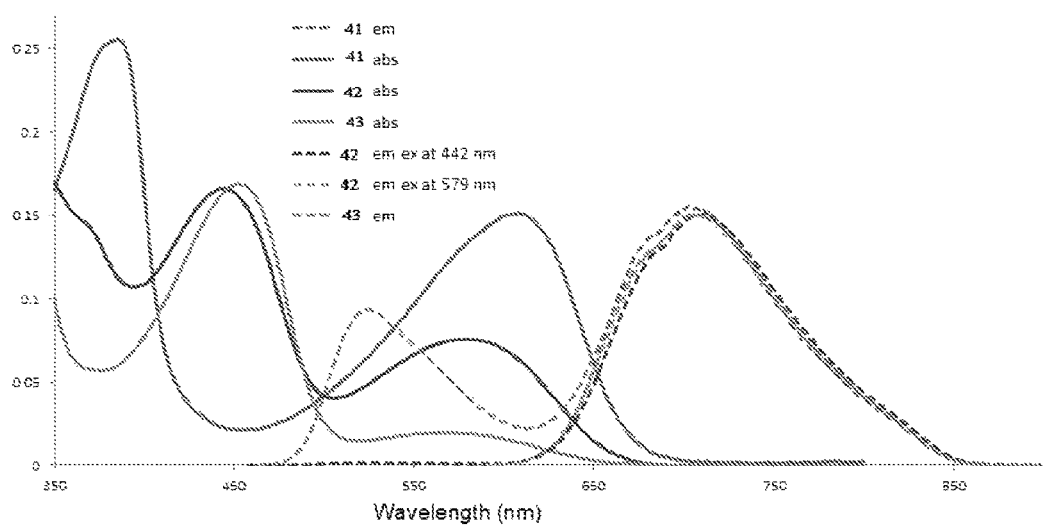

FIG. 7 shows absorption and emission spectra for borylated compounds 41, 42 and 43 dissolved in toluene.

Figure 8:
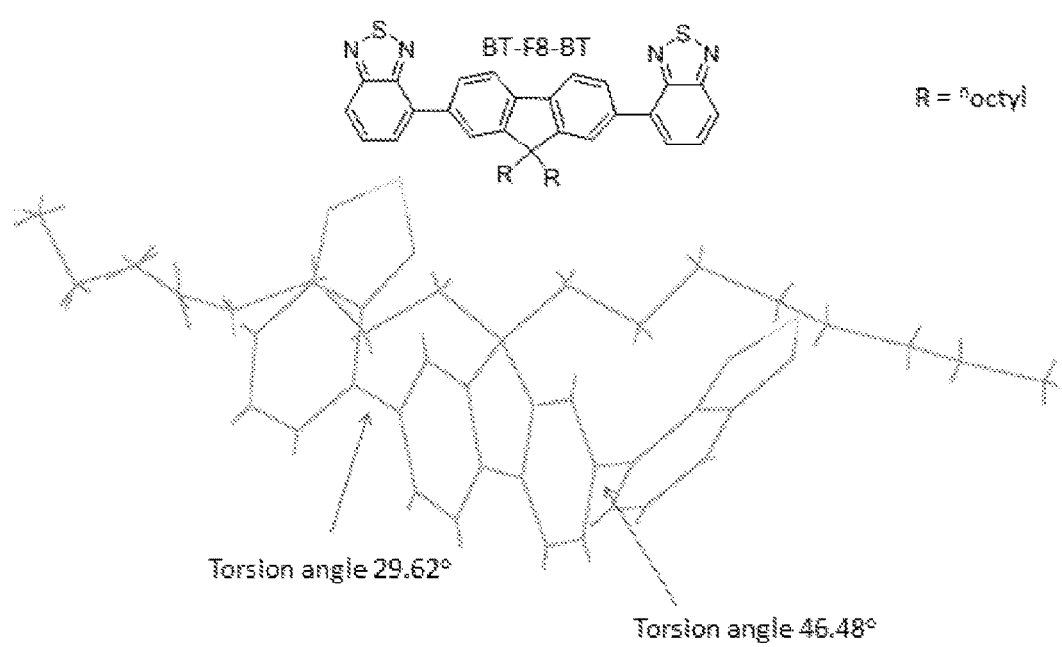

FIG. 8 shows the X-ray structure for the unborylated BT-F8-BT.

Figure 9:
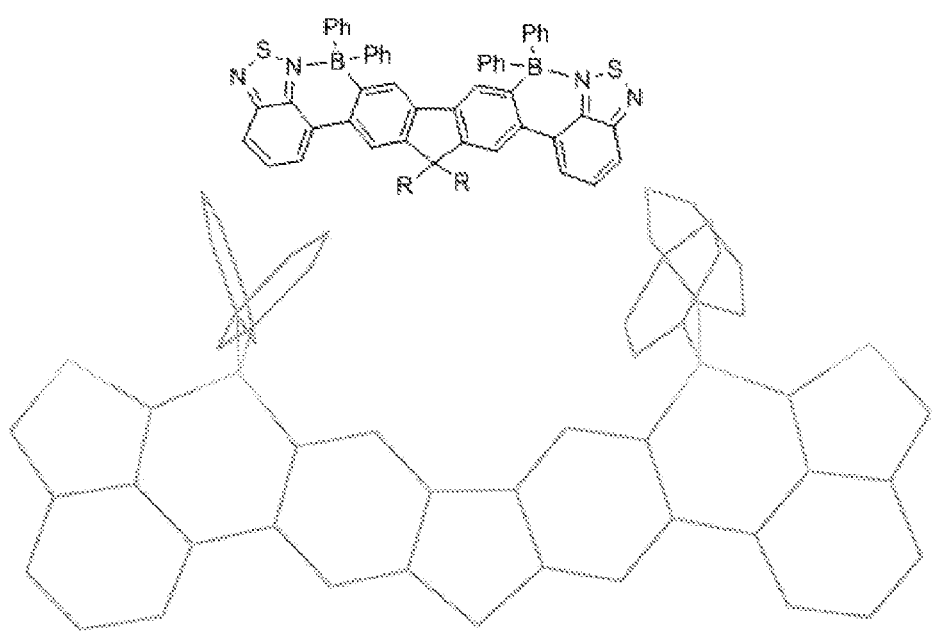

FIG. 9 shows the X-ray structure for the borylated compound 29

Figure 10:
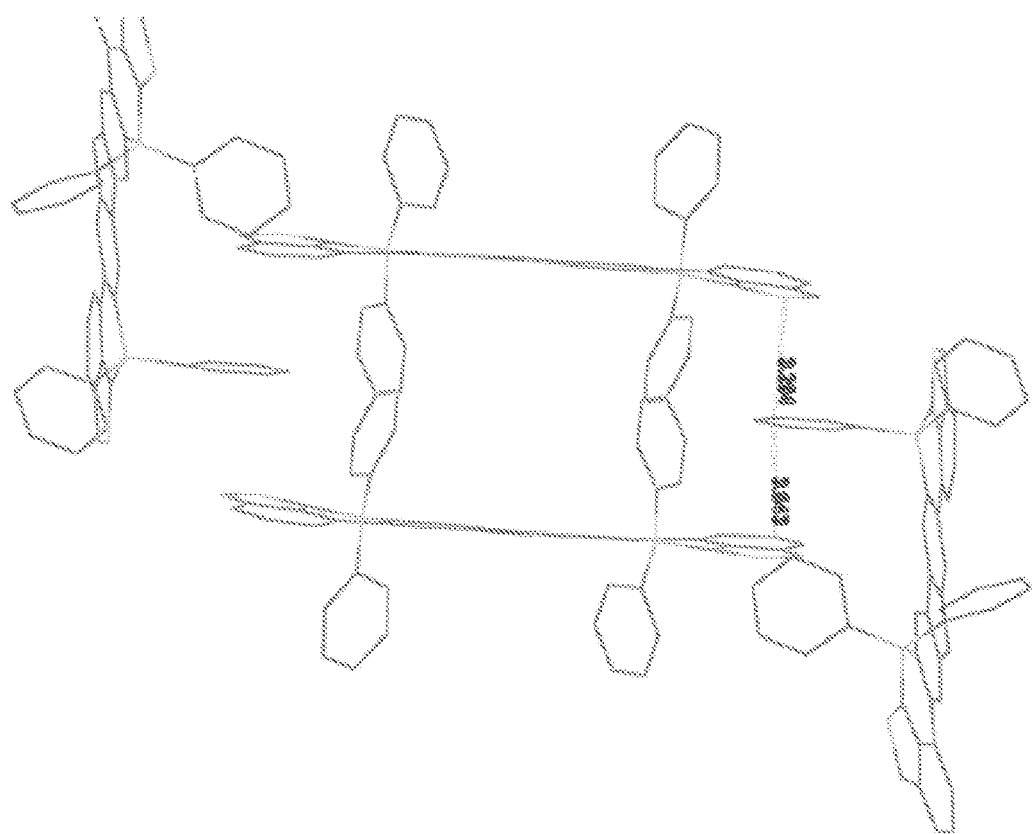

FIG. 10 shows the X-ray packing structure of compounds 29.

Figure 11:
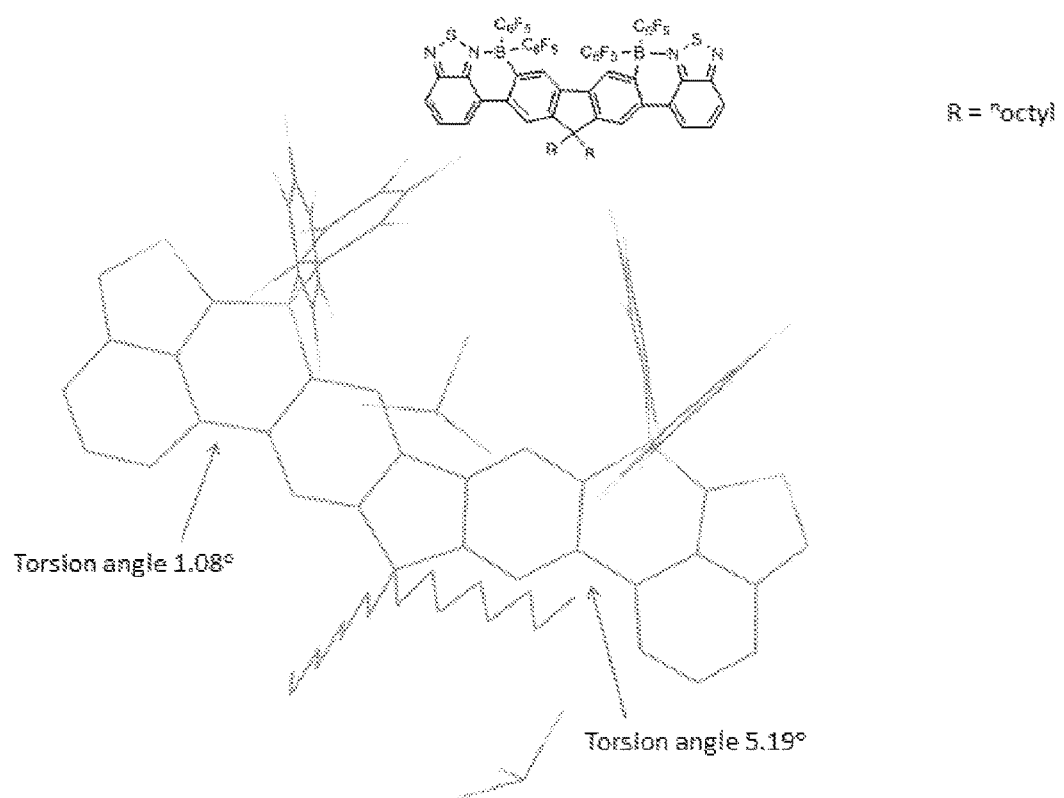

FIG. 11 shows the X-ray structure for the borylated compound 30.

Figure 12:
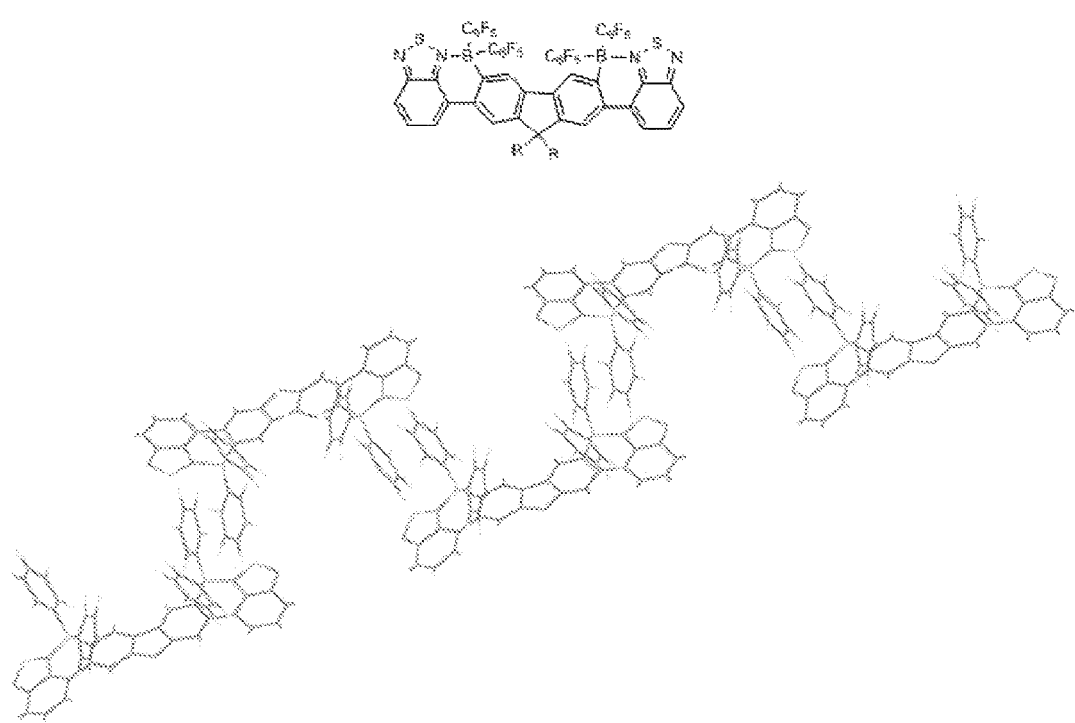

FIG. 12 shows the X-ray packing structure of compounds 30.

Figure 13:
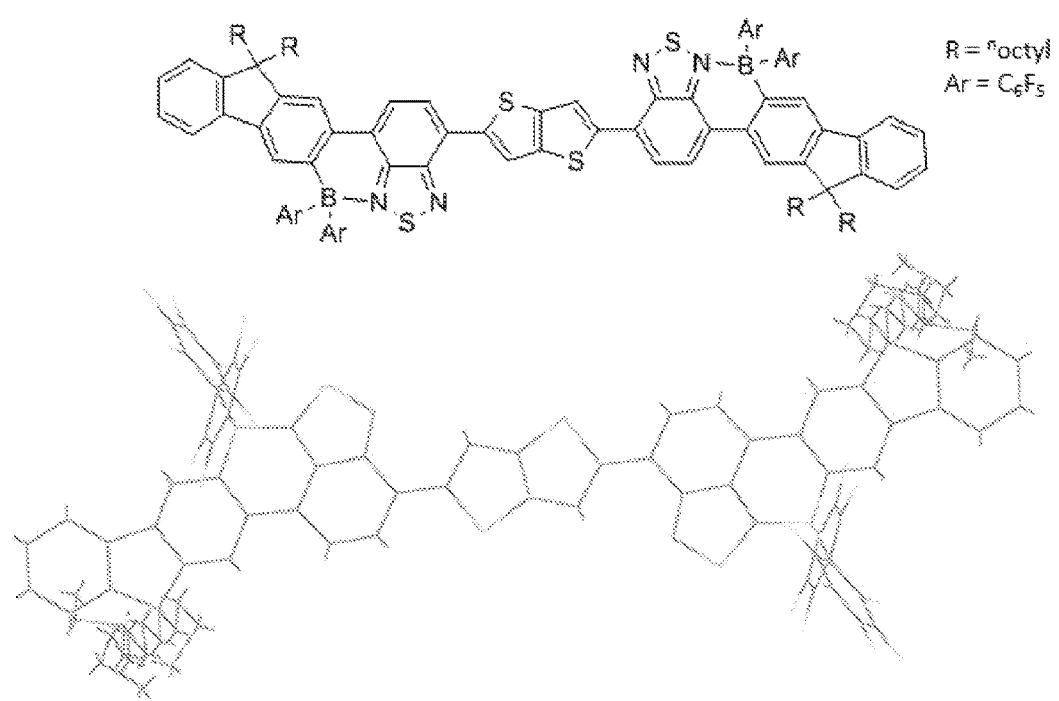

FIG. 13 shows the X-ray structure for the borylated compound 22.

Figure 14:
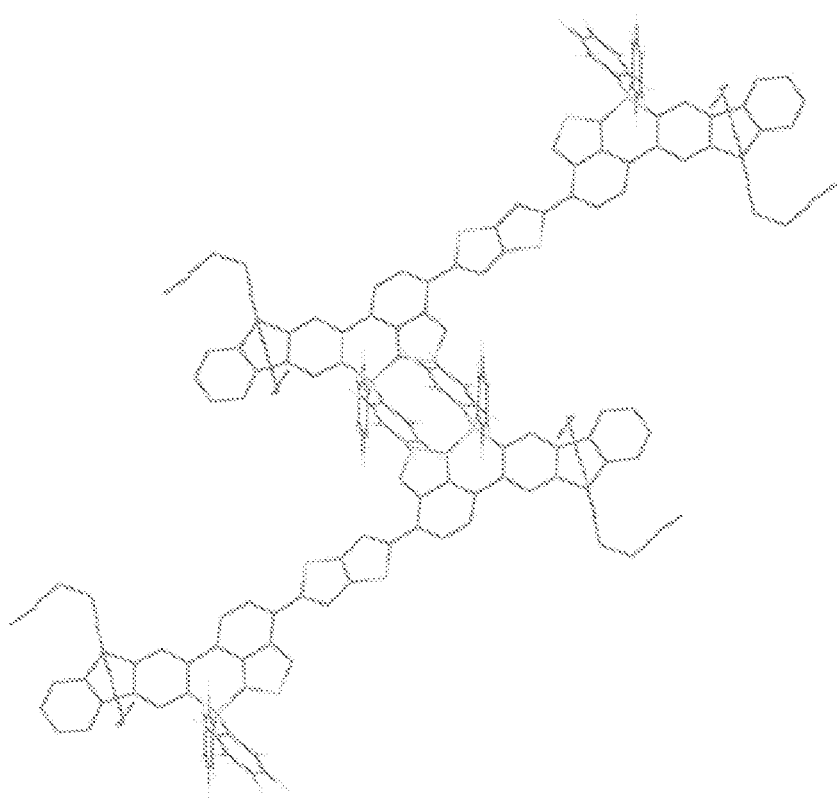

FIG. 14 shows the X-ray packing structure of compounds 22.

Figure 15:
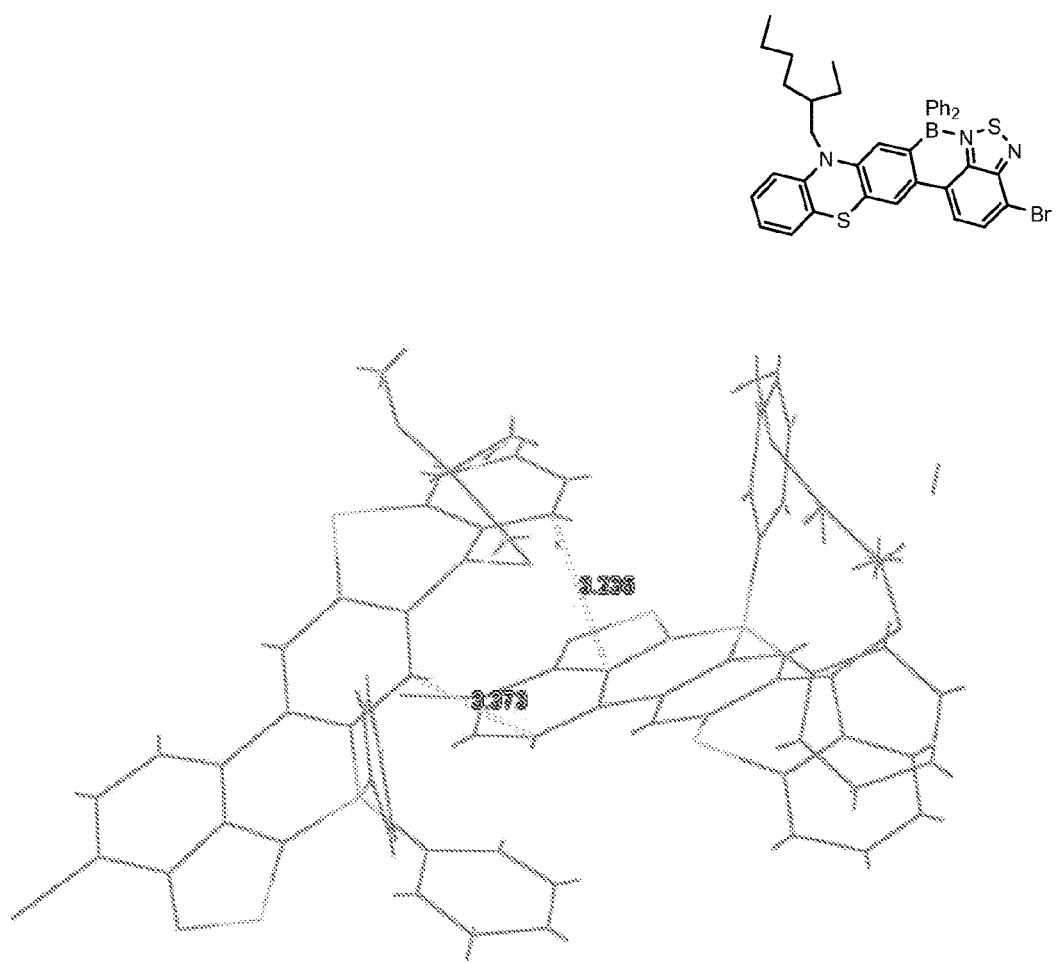

FIG. 15 shows the X-ray packing structure of compounds 35.

Figure 16:
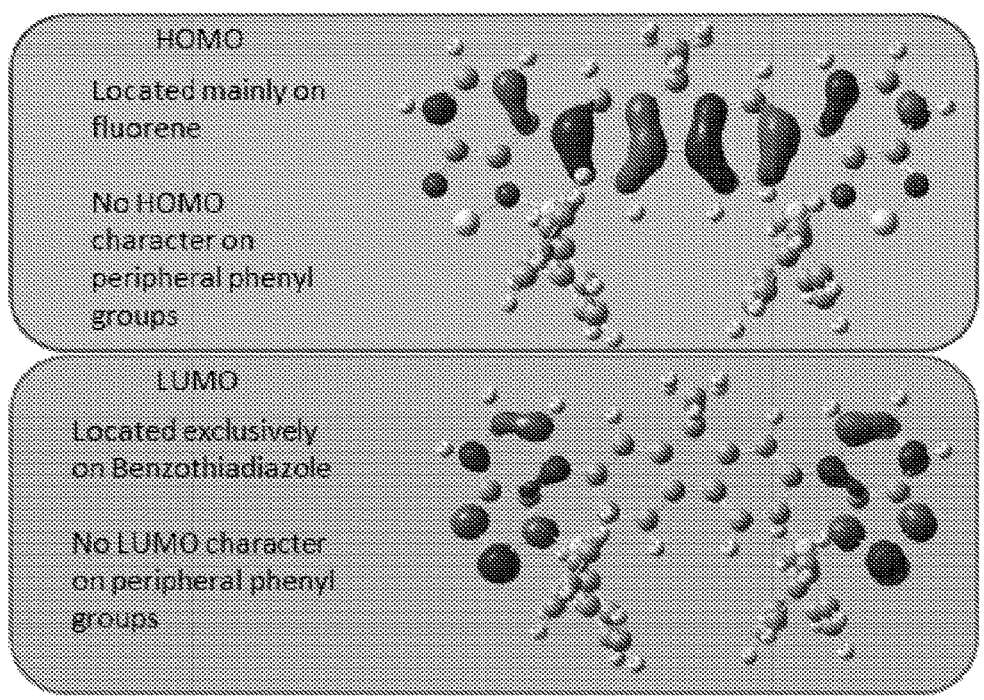

FIG. 16 shows computational modelling of the molecular orbital of compound 29.

Figure 17:
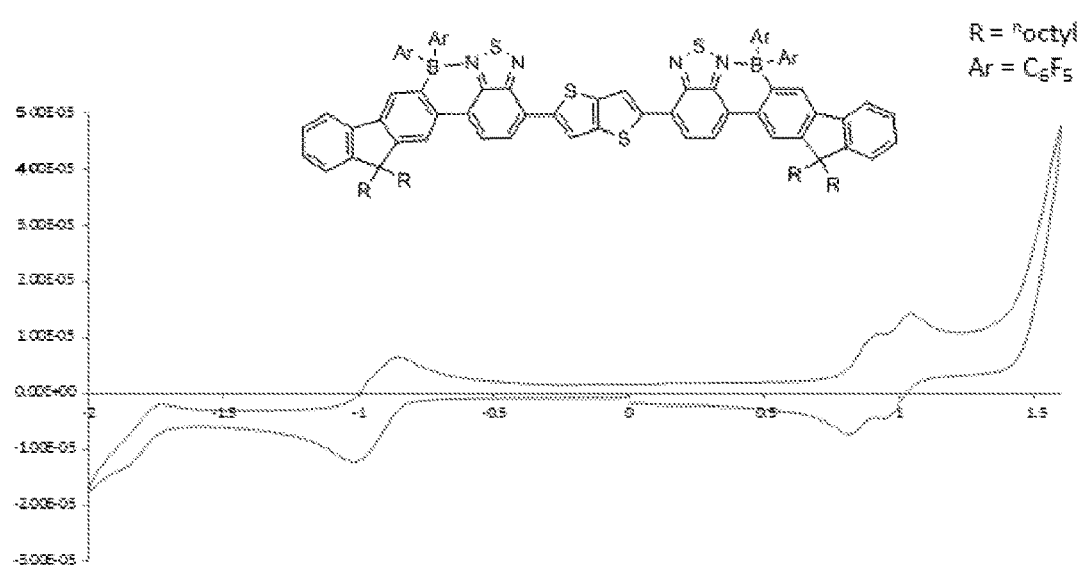

FIG. 17 shows the cyclic voltammogram for compound 22.

Figure 18:
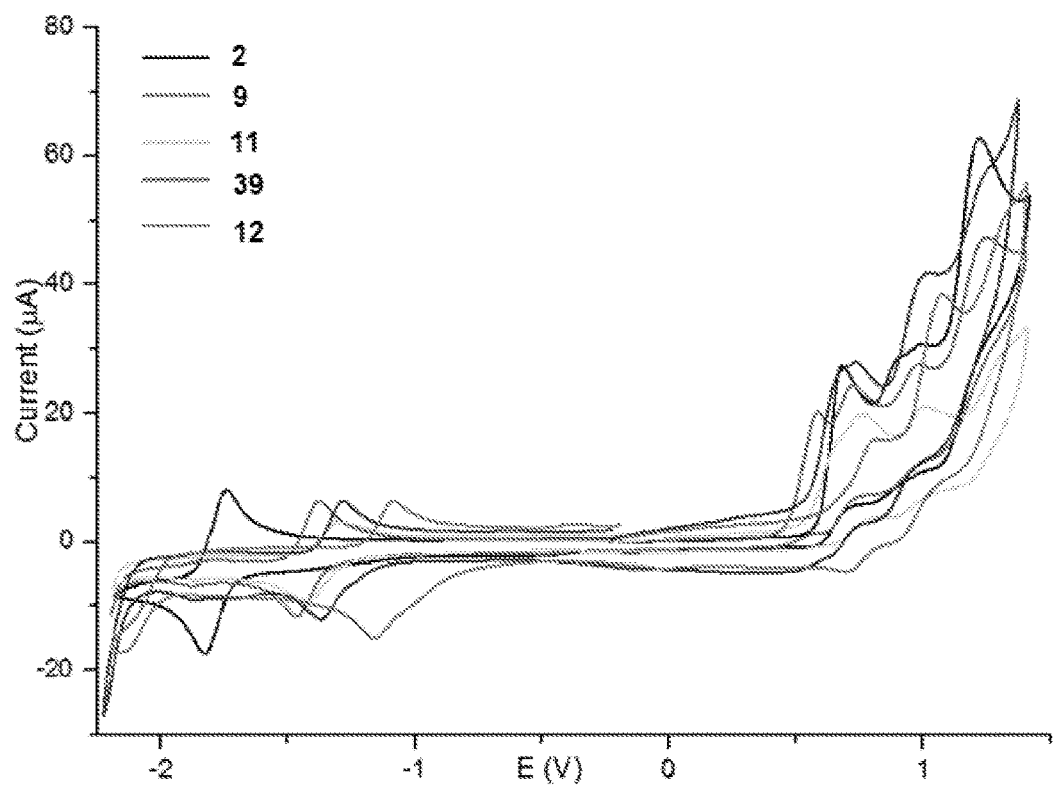

FIG. 18 shows the cyclic voltammograms for compounds 2, 9, 11, 39, and 12.

EXAMPLE 1—PREPARATION OF COMPOUNDS

Synthesis of 1

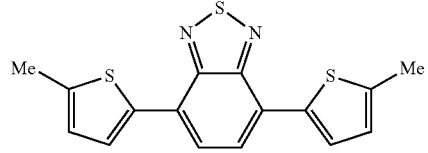 [SMILES: Cc1ccc(-c2ccc(-c3ccc(C)s3)c3nsnc23)s1]

4,7-dibromobenzo[c][1,2,5]thiadiazole (2.54 g, 8.65 mmol), trimethyl(5-methylthiophen-2-yl)stannane (4.57 g, 17.3 mmol) and Pd(PPh$_3$)$_4$ (1.00 g, 0.86 mmol) were mixed in dry toluene (50 ml) under an nitrogen atmosphere and stirred for 24 h at 100° C. under reflux. The mixture was cooled to room temperature and then diluted with DCM (150 mL). The reaction mixture was then washed with brine (1×100 mL), water (3×100 mL), and then dried over MgSO$_4$. After evaporating the solvent, the residue was purified by column chromatography on silica gel [eluent: hexane/DCM (3/2)] to afford 1 as a red powder. Yield: 0.981 g, 34%.

$^1$H NMR (400 MHz, CDCl$_3$) δ=7.91 (d, J=3.6 Hz, 2H), 7.78 (s, 2H), 6.87 (dd, J=1.2, 4.6 Hz, 2H), 2.59 (s, 3H) ppm.

Synthesis of 2

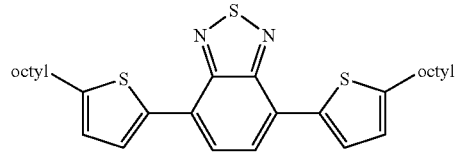

4,7-dibromobenzo[c][1,2,5]thiadiazole (2.00 g, 6.80 mmol), tri$^n$butyl(5-octylthiophen-2-yl)stannane (7.26 g, 14.96 mmol) and PdCl$_2$(PPh$_3$)$_2$ (0.48 g, 0.68 mmol) were mixed in dry THF (60 ml) under an nitrogen atmosphere and stirred for 22 h at 80° C. under reflux. The mixture was cooled to room temperature and then diluted with DCM (200 mL). The reaction mixture was then washed with saturated NaHCO$_3$ solution (1×100 mL), brine (1×200 mL), water (1×200 mL), and then dried over MgSO$_4$. After evaporating the solvent, the residue was purified by column chromatography on silica gel [eluent: hexane/chloroform (4/1)] to afford 2 as an orange powder. Yield: 1.08 g, 30%.

$^1$H NMR (400 MHz, CDCl$_3$) δ=7.94 (d, J=3.6 Hz, 2H), 7.79 (s, 2H), 6.88 (d, J=3.6 Hz, 2H), 2.90 (t, J=7.6, 4H), 1.76 (m, 4H), 1.47-1.22 (m, 20H), 0.89 (t, J=7.2, 6H);

$^{13}$C NMR (101 MHz, CDCl$_3$) δ=152.62, 147.80, 136.84, 127.32, 125.75, 125.22, 125.12, 31.90, 31.70, 30.33, 29.39, 29.28, 29.20, 22.70, 14.16;

MALDI-TOF: calc. for C$_{36}$H$_{44}$BN$_2$S$_3^+$ 524.2, found 523.9.

Synthesis of 3

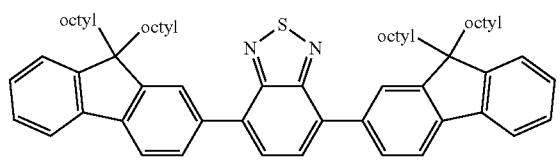

4,7-dibromobenzo[c][1,2,5]thiadiazole (1.36 g, 4.6 mmol), tri"butyl(9,9'-dioctyl-9H-fluoren-2-yl)-stannane, (6.70 g, 10.2 mmol) and PdCl$_2$(PPh$_3$)$_2$ (0.33 g, 0.047 mmol) were mixed in dry THF (80 ml) under an nitrogen atmosphere and stirred for 36 h at 80° C. under reflux. The mixture was cooled to room temperature and then diluted with ethyl acetate (100 mL). The reaction mixture was then washed with brine (2×100 mL), water (2×200 mL), and then dried over MgSO$_4$. After evaporating the solvent, the residue was purified by column chromatography on silica gel [eluent: hexane/DCM (9/1)] to afford 3 as a yellow viscous oil. Yield: 1.73 g, 41%.

$^1$H NMR (500 MHz, CDCl$_3$) δ=8.04 (dd, J=1.5, 8 Hz, 2H), 7.96 (d, J=1.0 Hz, 2H), 7.90 (s, 2H), 7.88 (d, J=8 Hz, 2H), 7.79 (dd, J=1.0, 6.5, 2H), 7.41-7.33 (m, 6H), 2.05 (m, 8H), 1.25-1.07 (m, 40H), 0.81 (t, J=7.0, 6H), 0.79 (m, 8H);

$^{13}$C NMR (126 MHz, CDCl$_3$) δ=154.4, 151.3, 151.1, 141.3, 140.7, 136.2, 133.6, 128.1, 127.9, 127.2, 126.8, 123.9, 123.0, 119.9, 119.7, 55.2, 40.3, 31.8, 30.1, 29.2, 29.2, 23.9, 22.6, 14.0;

MALDI-TOF: calc. for C$_{64}$H$_{84}$N$_2$S$^+$ 913.4, found 913.4.

Synthesis of 4

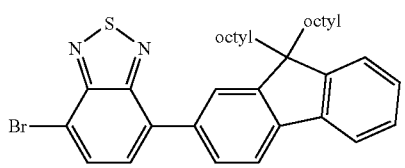

4,7-dibromobenzo[c][1,2,5]thiadiazole (2.7 g, 9.3 mmol), tri"butyl(9,9'-dioctyl-9H-fluoren-2-yl)-stannane, (75 g, 11 mmol) and PdCl$_2$(PPh$_3$)$_2$ (0.64 g, 0.092 mmol) were mixed in dry THF (80 ml) under an nitrogen atmosphere and stirred for 36 h under reflux. The mixture was cooled to room temperature and then diluted with ethyl acetate (100 mL). The reaction mixture was then washed with brine (2×100 mL), water (2×200 mL), and then dried over MgSO$_4$. After evaporating the solvent, the residue was purified by column chromatography on silica gel [eluent: hexane/DCM (9/1)] to afford 4 as a yellow viscous oil. Yield: 2.27 g, 54%.

$^1$H NMR (400 MHz, CDCl$_3$) δ=7.96 (d, J=7.6 Hz, 1H), 7.94-7.90 (m, 1H), 7.89-7.81 (m, 2H), 7.80-7.73 (m, 1H), 7.66 (d, J=7.6 Hz, 1H), 7.42-7.31 (m, 3H), 2.02 (td, J=7.0, 9.7 Hz, 4H), 1.26-1.00 (m, 20H), 0.85-0.63 (m, 10H);

$^{13}$C NMR (126 MHz, CDCl$_3$) δ=154.0, 153.3, 151.3, 151.2, 141.7, 140.4, 135.2, 134.6, 132.3, 128.1, 127.9, 127.4, 126.9, 123.8, 123.0, 120.0, 119.8, 112.6, 55.2, 40.2, 31.8, 30.0, 29.2, 23.8, 22.6, 14.0;

MALDI-TOF: calc. for C$_{35}$H$_{43}$N$_2$SBr$^+$ [M+H]$^+$ 604.7, found 604.7.

Synthesis of 5

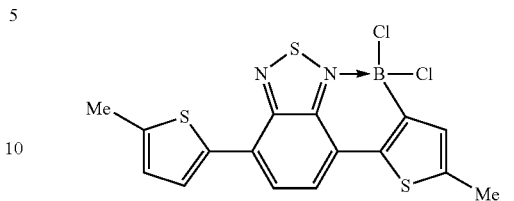

BCl$_3$ (1M solution in Heptanes) (0.15 mL, 0.15 mmol) was added to a bright red solution of 1 (0.050 g, 0.015 mmol) in DCM (0.7 mL) in a Young's NMR tube resulting in large amounts of dark blue precipitate forming. 2,6-dichloropyridine (0.022, 0.15 mmol) was added to the reaction mixture followed by the addition of AlCl$_3$ after rotating for 20 minutes. After rotating for 16 hours, the sparingly soluble desired product was extracted with C$_6$D$_6$ (1.5 mL) for NMR examination. The low solubility frustrated attempts to record a $^{13}$C{$^1$H} NMR spectrum.

$^1$H NMR (400 MHz, C$_6$D$_6$) δ=7.58 (d, J=3.6 Hz, 1H), 7.86 (s, 1H), 7.04 (d, J=7.6, 1H), 6.86 (d, J=7.2 Hz, 1H), 6.59 (dd, J=1.0, 3.8, 1H), 2.18 (s, 3H), 2.15 (s, 3H) ppm;

$^{11}$B NMR (128.4 MHz, CD$_2$Cl$_2$) δ=~4 (broad) ppm.

Synthesis of 6:

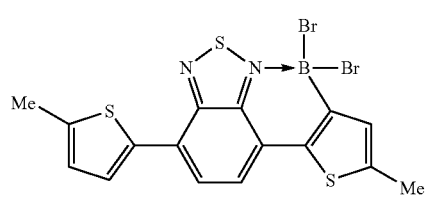 [SMILES: Cc1ccc(-c2ccc3c4c2ns[n+]4[B-](Br)(Br)c2cc(C)sc2-3)s1]

BBr$_3$ (1M solution in Heptanes) (0.10 mL, 0.10 mmol) was added to a bright red solution of 1 (0.033 g, 0.010 mmol) in DCM (0.7 mL) in a Young's NMR tube resulting in large amounts of dark blue precipitate forming. A second equivalent of BBr$_3$ (1M solution in Heptanes) (0.10 mL, 0.10 mmol) was then added (0.022, 0.15 mmol) to the reaction mixture followed by the addition of Hünigs base (0.017 mL, 0.010 mmol). The reaction mixture was then rotated for 20 minutes and then heated at 60° C. for 16 hours. After rotating for 16 hours the sparingly soluble desired product was extracted with dry THF (1.5 mL) for NMR examination. The low solubility frustrated attempts to record a $^{13}$C{$^1$H} NMR spectrum.

$^1$H NMR (400 MHz, THF) δ=8.00 (d, J=4.0 Hz, 1H), 7.92 (d, J=7.6, 1H), 7.64 (d, J=7.6, 1H), 6.886 (s, 1H), 6.81 (d, 3.6, 1 H), 2.51 (s, 3H), 2.50 (s, 3H) ppm;

$^{11}$B NMR (128.4 MHz, THF) δ=~17 ppm

Synthesis of 7:

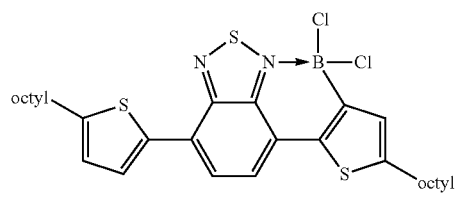

BCl₃ (1M solution in heptanes) (0.60 mL, 0.6 mmol) was added to a bright orange solution of 2 (0.312 g, 0.060 mmol) in DCM (10 mL) in a Schlenk flask resulting in a colour change to dark blue and the reaction mixture was stirred for 16 hours (addition of a base was unnecessary as in the open system of a Schlenk flask gaseous HCl is lost from solution under the flow of nitrogen). The solvent was removed under reduced pressure and 7 was isolated as a dark blue powder (322 mg, 89%).

¹H NMR (400 MHz, C₆D₆): δ=7.65 (d, J=3.8 Hz, 1H), 7.54 (s, 1H), 7.11 (d, J=7.6 Hz, 1H), 6.97 (d, J=7.6 Hz, 1H), 6.73 (d, J=3.8 Hz, 1H), 2.68 (q, J=8.0 Hz, 4H), 1.72-1.52 (m, 4H), 1.38-1.14 (m, 20H), 0.92 (t, J=6.9 Hz, 6H);

¹³C NMR (101 MHz, DCM) δ=151.3, 150.8, 150.0, 145.0, 134.7, 131.7, 129.2, 128.8, 127.9, 126.2, 126.0, 125.7, 122.2, 32.0, 31.7, 31.7, 30.6, 30.4, 29.4, 29.4, 29.2, 22.8, 14.0;

All CH₂ resonances were not distinctly observed due to similar magnetic environments, some CH environments are obscured by solvent.

¹¹B NMR (128.4 MHz, C₆D₆) δ=~3 (broad) ppm.

Synthesis of 8:

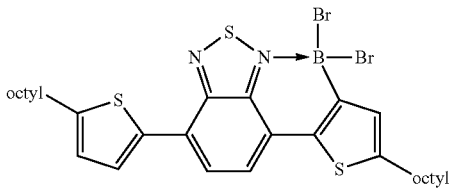

BBr₃ (1M solution in Heptanes) (0.20 mL, 0.20 mmol) was added to a bright orange solution of 2 (0.026 g, 0.005 mmol) in DCM (0.7 mL) in a Young's NMR tube resulting in a colour change to dark blue and the formation of precipitate. 2,6-Lutidine (0.011 mL, 0.1 mmol) was added to the reaction mixture. The reaction mixture was heated at 60° C. for 24 hours and upon slowly cool crystals of 8 precipitated from the reaction mixture.

¹H NMR (500 MHz, C₆D₆) δ=7.64 (d, J=3.2 Hz, 1H), 7.55 (s, 1H), 7.09 (d, J=7.6 Hz, 1H), 6.94 (d, J=7.6 Hz, 1H), 6.73 (d, J=3.0, 1 H), 2.69 (t, J=7.57 Hz, 2H), 2.65 (t, J=7.72 Hz, 2H), 1.54-1.70 (m, 4H), 1.37-1.18 (m, 20H), 0.92 (t, J=6.94 Hz, 6H) ppm;

¹¹B NMR (128.4 MHz, C₆D₆) δ=~6 (broad) ppm.

Synthesis of 9:

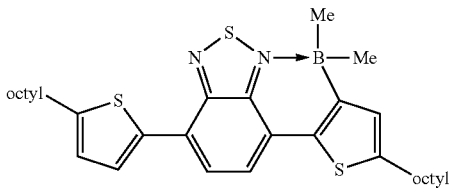

A solution of AlMe₃ (2M solution in heptanes) (0.4 mL, 0.080 mmol) in dry toluene (3 mL) was slowly added a stirred solution of 7 (0.20 g, 0.33 mmol) in dry toluene (3 mL). After stirring for 20 minutes the excess AlMe₃ and solvent were removed under reduced pressure. Compound 9 was isolated as a dark blue/purple powder without further purification (178 mg, 96%).

¹H NMR (400 MHz, C₆D₆) δ=7.84 (d, J=3.8 Hz, 1H), 7.35 (d, J=7.6 Hz, 1H), 7.11 (s, 1H), 7.05 (d, J=7.3 Hz, 1H), 6.78 (d, J=3.5 Hz, 1H), 2.81 (t, J=7.7 Hz, 2H), 2.72 (t, J=7.6 Hz, 2H), 1.76-1.61 (m, 4H), 1.38-1.17 (m, 20H), 0.92 (t, J=7.2, 3 H), 0.91 (t, J=7.2, 3 H), 0.72 (s, 6H) ppm;

¹³C NMR (101 MHz, C₆D₆) δ=152.46, 149.50, 148.09, 147.56, 136.97, 130.76, 130.73, 130.24, 127.75, 127.72, 126.47, 126.03, 123.77, 120.63, 32.61, 32.49, 32.38, 31.29, 30.93, 30.11, 30.00, 29.84, 23.43, 17.85, 14.73, 14.71 ppm;

All CH₂ resonances were not distinctly observed due to similar magnetic environments.

No peak was observable in the ¹¹B NMR spectrum at 20° C. in C₆H₆.

MALDI-TOF: calc. for C₃₁H₄₂BN₂S₃⁺ [M–CH₃]⁺ 549.7, found 549.6.

Synthesis of 10:

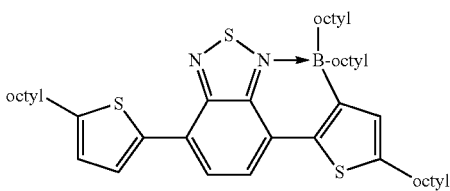

A solution of Al(octyl)₃ (0.477M solution in heptanes) (0.15 mL, 0.070 mmol) in dry toluene (2 mL) was slowly added a stirred solution of 7 (0.020 g, 0.033 mmol) in dry toluene (3 mL). After stirring for 3 hours the reaction was quenched with water (5 mL), extracted with chloroform (3×20 mL), dried (MgSO₄) and the solvents were removed under reduced pressure. The crude product was purified by chromatography on base treated (5% NEt₃ in hexane) silica gel by using hexane as eluent. Compound 10 was isolated as a dark blue/purple oil. Yield (14 mg, 57%).

¹H NMR (400 MHz, CDCl₃): δ=7.87 (d, J=4.0, 1H), 7.78 (d, J=7.6, 1H), 7.37 (d, J=7.6, 1H), 6.87 (d, J=4.0, 1H), 6.80 (s, 1H), 2.89 (t, J=7.6, 2H), 2.88 (t, J=7.6, 2H), 1.81-1.69 (m, 4H), 1.46-107 (m, 40H), 0.89 (2 overlapping triplets, 10H), 0.88 (t, J=6.8, 6H), 0.78-0.63 (m, 4H);

No peak was observable in the ¹¹B NMR.

Synthesis of 11

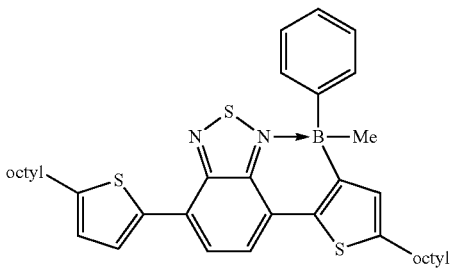

PhBCl₂ (0.013 mL, 0.1 mmol) was added to a bright orange solution of 2 (0.52 g, 0.010 mmol) in DCM (0.7 mL) in a Young's NMR tube resulting in a colour change to dark green and the reaction mixture was rotated for 16 hours. 2,6-Lutidine (0.011 mL, 0.1 mmol) was added to the reaction mixture and after rotating for 16 hours the solvent was removed under reduced pressure to leave a dark blue/green residue. The residue was dissolved in benzene (0.7 mL) and AlMe₃ (2M solution in heptanes) (0.05 mL, 0.01 mmol) was added. After the reaction mixture had been rotated for 16 hour the excess AlMe₃ and solvent were removed under reduced pressure. The crude product was purified by chromatography on base treated (5% NEt$_3$ in hexane) silica gel by using hexane as eluent and Compound 11 was isolated as a dark blue residue (22 mg, 35%).

$^1$H NMR (400 MHz, C$_6$D$_6$) δ=7.84 (d, J=3.8 Hz, 1H), 7.79 (d, J=7.6 Hz, 1H), 7.5 (d, J=7.57 Hz, 1H), 7.36-7.28 (m, 2H), 7.22 (t, J=7.2 Hz, 2H), 7.47 (tt, J=1.4, 7.2, 1 H), 6.86 (d, J=3.5 Hz, 1H), 6.74 (s, 1H), 2.88 (t, J=7.7 Hz, 2H), 2.83 (t, J=7.7 Hz, 2H), 1.79-1.56 (m, 4H), 1.45-1.24 (m, 20H), 0.90 (t, J=6.8, 6 H), 0.69 (s, 3H) ppm;

$^{13}$C NMR (101 MHz, CDCl$_3$) δ=151.86, 149.06, 147.69, 147.34-147.37 (m, 1C) 135.53, 131.73, 130.20, 129.85, 128.18, 127.67, 127.10, 126.03, 125.38, 125.32, 123.51, 120.98, 31.83, 31.58, 31.52, 30.92, 30.50, 30.25, 29.31, 29.25, 29.21, 29.12, 22.65, 14.09 ppm;

All C̲H$_2$ resonances were not distinctly observed due to similar magnetic environments.

No peak was observable in the $^{11}$B NMR.

MALDI-TOF: calc. for C$_{36}$H$_{44}$BN$_2$S$_3$$^+$ [M–C$_6$H$_5$]$^+$ 611.8, found 611.8.

Synthesis of 12:

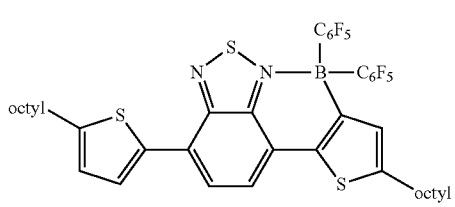

Zn(C$_6$F$_5$)$_2$ (152 mg, 0.4 mmols) was added to a toluene (5 mL) solution of 7, the reaction mixture was stirred for 3 hours and then after the addition of wet toluene the solution was passed through a plug of silica. Solvent was removed under reduced pressure to afford a dark blue residue (Yield 151 mg, 92%).

$^1$H NMR (400 MHz, CDCl$_3$) δ=7.88 (d, J=3.8 Hz, 1H), 7.83 (d, J=7.6 Hz, 1H), 7.61 (d, J=7.6 Hz, 1H), 6.89 (d, J=3.5 Hz, 1H), 6.78 (s, 1H), 2.89 (t, J=7.6, 2 H), 2.82 (t, J=7.6, 2H), 1.81-1.64 (m, 4H), 1.49-1.20 (m, 22H), 0.89 (t, J=6.8, 3H), 0.88 (t, J=6.8, 3 H).

$^{13}$C NMR (126 MHz, CDCl$_3$) δ=150.4, 148.9, 147.8, 146.0, 133.8, 128.8, 127.0, 127.0, 124.6, 123.4, 122.7, 122.6, 30.8, 30.8, 30.5, 30.5, 29.4, 29.3, 28.3, 28.3, 28.2, 28.1, 28.1, 21.6, 21.6, 13.0, 13.0

$^{19}$F NMR (376 MHz, CDCl$_3$) δ=−132.43 (dd, J=22.56, 7.90, 4F), −156.58 (t, 20.30, 2F), −162.40 (m, 8F)

MALDI-TOF: calc. for C$_{42}$H$_{39}$BN$_2$SF$_{10}$$^+$ 868.7, found 868.7.

Synthesis of 13:

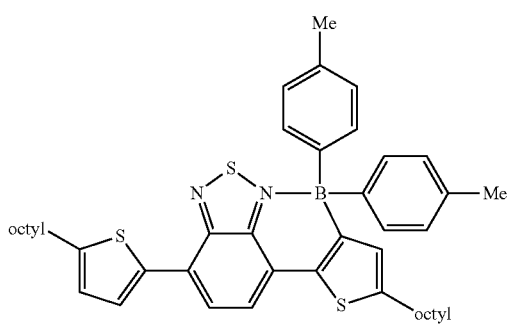

A 0.25M solution of Zn(p-Tolyl)$_2$ dissolved in THF (1.4 mL) was evaporated to dryness then suspended in dry toluene (3 mL). 7 (20 mg, 0.033 mmol) was added to the suspension and the reaction mixture was stored at room temperature for 12 hours. The crude product was purified by chromatography on base treated (5% NEt$_3$ in hexane) silica gel by using hexane as eluent. Solvent was removed under reduced pressure to afford a dark blue residue (Yield 5.5 mg, 23%).

$^1$H NMR (400 MHz, CDCl$_3$) δ=7.82 (d, J=3.5 Hz, 1H), 7.76 (d, J=7.6 Hz, 1H), 7.47 (d, J=7.6 Hz, 1H), 7.17 (d, J=8.1 Hz, 4H), 7.07 (d, J=7.8 Hz, 4H), 6.85 (d, J=3.8 Hz, 1H), 6.79 (s, 1H), 2.88 (t, J=7.6 Hz, 2H), 2.81 (t, J=7.6 Hz, 2H), 2.32 (s, 6H), 1.81-1.64 (m, 4H), 1.48-1.38 (m, 4H), 1.38-1.21 (m, 20H), 0.91 (t, J=5.2 Hz, 6H)

$^{13}$C NMR (126 MHz, CDCl$_3$) δ=151.7, 150.8, 148.9, 147.9, 147.5, 135.5, 133.2, 131.0, 130.2, 128.5, 128.1, 127.3, 125.5, 125.1, 123.7, 121.5, 31.9, 31.6, 31.5, 30.6, 30.3, 29.4, 29.3, 29.3, 29.2, 22.7, 22.7, 21.2, 14.1

Synthesis of 14

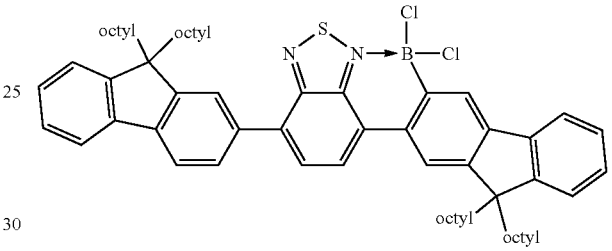

BCl$_3$ 1M solution in DCM) (0.15 mL, 0.12 mmol) was added to a bright orange solution of 3 (0.078 g, 0.085 mmol) in DCM (3 mL) in a Schlenk flask. The reaction mixture was stirred for 16 hours where upon a colour change to dark blue was observed. The solvent and excess BCl$_3$ was removed under reduced pressure to yield a dark blue residue.

$^1$H NMR (500 MHz, CD$_2$Cl$_2$) δ=8.61 (d, J=7.5 Hz, 1H), 8.40 (s, 1H), 8.16 (d, J=7.2 Hz, 1H), 8.02 (s, 1H), 8.01 (d, J=7.6, 1 H), 7.94-7.89 (m, 2H), 7.82 (d, J=5.7 Hz, 1H), 7.35-7.47 (m, 6H), 2.17-2.03 (m, 8H), 1.25-1.02 (m, 40H), 0.85-0.66 (m, 20H) ppm;

$^{13}$C NMR (126 MHz, CD$_2$Cl$_2$) δ=154.09, 152.22, 152.03, 152.00, 151.93, 146.17, 143.84, 143.22, 140.93, 140.78, 134.36, 134.07, 131.53, 128.77, 128.58, 128.44, 128.23, 127.62, 127.59, 127.07, 125.53, 124.50, 123.72, 123.57, 121.20, 120.78, 120.68, 116.92, 55.99, 55.81, 41.10, 40.77, 32.37, 30.65, 30.56, 29.82, 29.78, 24.53, 24.50, 23.18, 23.17, 14.40 ppm;

All C̲H$_2$ or C̲H resonances were not distinctly observed due to similar magnetic environments.

$^{11}$B NMR (128.4 MHz, CD$_2$Cl$_2$): δ=10.0 (s) ppm.

Synthesis of 15

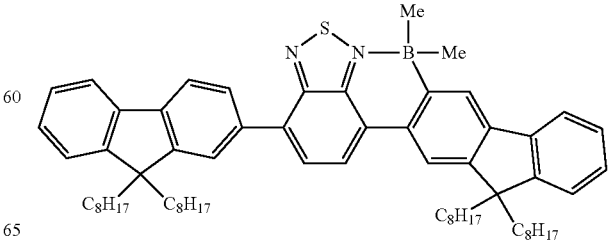

AlMe$_3$ 2M in heptanes (0.11 mL, 0.22 mmol) was added to a toluene (3 mL) solution of 14 (935 mg, 0.10 mmols). After 10 minutes the excess AlMe$_3$ was removed under reduced pressure. The reaction mixture was then filtered through base treated silica (5% NEt$_3$/95% Hexane) and solvent was removed under reduced pressure to afford a dark purple residue.

$^1$H NMR (500 MHz, DCM) δ=8.37 (d, J=7.9 Hz, 1H), 8.10-7.98 (m, 4H), 7.96 (s, 1H), 7.90 (d, J=7.6 Hz, 1H), 7.86-7.78 (m, 2H), 7.46-7.30 (m, 6H), 2.07 (m., 8H), 1.04-1.24 (m., 40H), 0.83-0.68 (m, 20H), 0.47 (s, 6H) ppm;

$^{13}$C NMR (101 MHz, DCM) δ=154.3, 151.7, 151.5, 148.5, 148.3, 142.0, 141.9, 141.3, 140.6, 134.7, 131.9, 130.9, 129.4, 129.2, 128.0, 127.7, 127.3, 127.1, 126.9, 123.7, 123.2, 123.1, 123.1, 120.2, 120.2, 120.0, 116.6, 55.5, 54.9, 32.0, 30.3, 30.2, 29.4, 29.4, 24.2, 24.1, 22.8, 17.9, 14.0.

Synthesis of 16

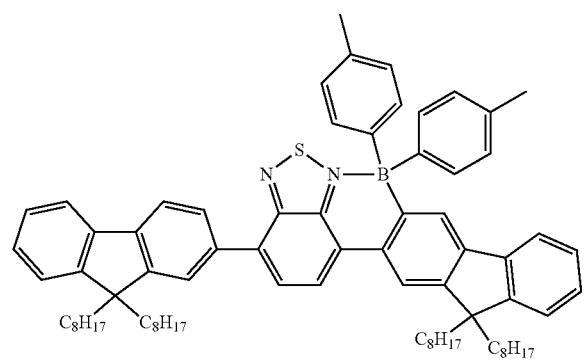

Zn(p-Tolyl)$_2$ (240 mg, 1 mmol) was added to a toluene (5 mL) solution of 14, the reaction mixture was stirred for 3 hours and then after the addition of wet toluene the solution was purified via silica gel chromatography (eluent hexane) to afford a dark purple residue. (Yield 152 mg, 57.3%).

$^1$H NMR (500 MHz, CDCl$_3$) δ=8.43 (d, J=7.9 Hz, 1H), 8.08 (s, 1H), 8.04 (d, J=7.5, 1 H), 7.98-7.92 (m, 2H), 7.88 (d, J=7.5, 1H), 7.85 (s, 1H), 7.80-7.78 (m, 1H), 7.65-7.62 (m, 1H), 7.44-7.33 (m, 4H), 7.31-7.21 (m, 6H), 7.09 (d, J=7.6 Hz, 4H), 2.33 (s, 6H), 2.12-1.99 (m, 8H), 1.25-1.07 (m, 40H), 0.83 (t, J=7.5, 6H), 0.82 (t, J=7.5, 6H), 0.77 (m, 8H).

Synthesis of 17

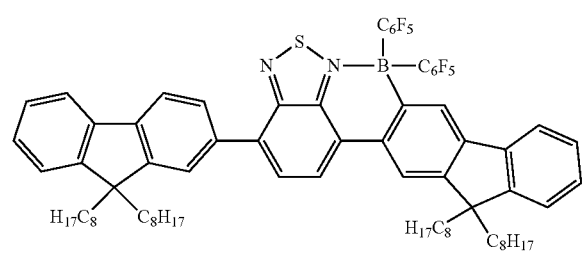

Zn(C$_6$F$_5$)$_2$ (97 mg, 0.242 mmol) was added to a toluene (5 mL) solution of 14 made in-situ (110 mg, 0.11 mmol), the reaction mixture was stirred for 3 hours and then after the addition of 'wet' toluene (unpurified toluene used as received) to quench unreacted diaryl zinc reagent the solution was purified via silica gel chromatography (eluent hexane) to afford 17 as a dark purple residue. (Yield 131 mg, 94%).

$^1$H NMR (400 MHz, CDCl$_3$) δ=8.58 (d, J=8.1 Hz, 1H), 8.21-8.07 (m, 2H), 8.03 (s, 1H), 7.94 (m., 2H), 7.89-7.78 (m, 2H), 7.74 (br. s., 1H), 7.49-7.30 (m, 6H), 2.11 (m., 8H), 1.13 (m 40H), 0.89-0.66 (m, 20H);

$^{13}$C NMR (101 MHz, CDCl$_3$) δ=153.7, 151.5, 151.3, 151.3, 150.2, 147.8, 143.0, 142.4, 140.4, 140.2, 133.6, 133.0, 131.0, 128.1, 128.1, 127.9, 127.8, 127.7, 127.0, 126.9, 125.8, 124.3, 123.8, 123.0, 122.9, 120.4, 120.2, 120.1, 116.3, 55.3, 55.0, 40.7, 40.3, 31.8, 30.1, 30.0, 29.2, 29.2, 29.2, 23.9, 23.8, 22.6, 22.6, 14.0, 14.0;

$^{19}$F NMR (376 MHz, CDCl$_3$) δ=−131.55 (dd, J=23.31, 8.65, 4F), −156.65 (t, 20.68, 2F), −162.62 (m, 4F) ppm;

$^{11}$B NMR (128.4 MHz, CD$_2$Cl$_2$): δ=~−4.0 (Broad).

MALDI-TOF: calc. for C$_{70}$H$_{83}$BF$_5$N$_2$S$^+$ [M−C$_6$F$_5$]$^+$ 1090.3, found 1090.4.

Synthesis of 18

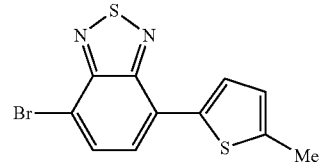 [SMILES: Cc1ccc(-c2ccc(Br)c3nsnc23)s1]

18 was isolated from the reaction mixture of 1 via column chromatography on silica gel [eluent: hexane/DCM (3/2)] to afford a yellow powder. (Yield: 0.252 g, 10%).

$^1$H NMR (400 MHz, CDCl$_3$) δ=7.91 (d, J=3.5 Hz, 1H), 7.86-7.80 (m, J=7.8 Hz, 1H), 7.66-7.61 (m, J=7.8 Hz, 1H), 6.87 (dd, J=1.0, 3.5 Hz, 1H), 2.58 (d, J=1.0 Hz, 3H)

Synthesis of 19

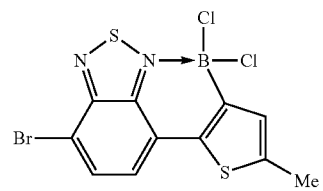 [SMILES: Cc1cc2c(s1)-c1ccc(Br)c3ns[n+](c13)[B-]2(Cl)Cl]

BCl$_3$ (ca. 0.8M solution in DCM) (0.3 mL, 0.24 mmol) was added to a bright yellow solution of 18 (0.031 g, 0.1 mmol) in DCM (3 mL) in a Schlenk flask. The reaction mixture instantly turned a dark purple colour and was stirred for 16 hours at room temperature. The solvent and excess BCl$_3$ was removed under reduced pressure. To afford compound 19.

Synthesis of 20

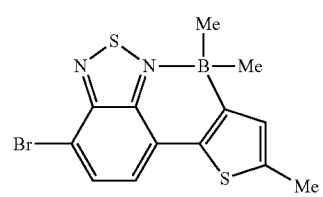

The reaction mixture containing 19 was then redissolved in dry toluene (8 mL) and a solution of AlMe$_3$ (2M solution in heptanes) (0.12 mL, 0.24 mmol) in toluene (1.0 mL) was slowly added. After 10 minutes the excess AlMe$_3$ and solvent were removed under reduced pressure. The crude product was purified by chromatography on base treated (5% NEt₃ in hexane) silica gel by using pentane as eluent. Compound 20 was isolated as a dark/purple air stable solid (11 mg, yield 32.6%).

¹H NMR (400 MHz, CD₂Cl₂) δ=7.86 (d, J=7.56 Hz, 1H), 7.27 (d, J=7.6 Hz, 1H), 6.80 (d, J=0.8 Hz, 1H), 2.53 (s, 3H), 0.28 (s, 6H) ppm;

¹³C NMR (101 MHz, CD₂Cl₂) δ=153.47, 147.86, 144.25, 136.18, 131.55, 129.50, 127.60, 120.60, 107.84, 15.94 ppm;

¹¹B NMR (128.4 MHz, CD₂Cl₂): δ=~1 (s) ppm.

Synthesis of 21

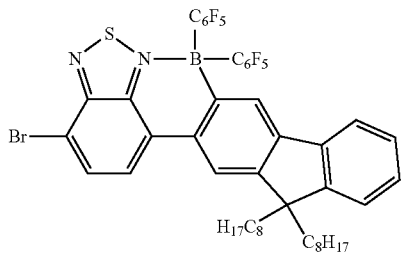

BCl₃ 1M solution in DCM) (2 mL, 2 mmol) was added to a bright yellow solution of 4 (200 mg, 0.33 mmol) in DCM (3 mL) in a Schlenk flask. The reaction mixture was stirred for 16 hours whereupon the colour change to the dark purple was observed. The solution was degassed and solvent was removed under reduced pressure to yield a dark purple residue. The reaction mixture was then dissolved in toluene (3 mL) and Zn(C₆F₅)₂ (265 mg, 0.66 mmol) was added. The reaction mixture was stirred for 2 hours and then after the addition of wet toluene the solution was passed through a plug of silica. The solvent was removed under reduced pressure to afford a dark purple residue. (Yield 296 mg, 95%).

¹H NMR (500 MHz, CDCl₃) δ=8.32 (d, J=7.9 Hz, 1H), 8.15 (d, J=7.8 Hz, 1H), 8.05 (s, 1H), 7.80 (s, 1H), 7.75-7.65 (m, 1H), 7.46-7.28 (m, 3H), 2.08 (t, J=8.3 Hz, 4H), 1.24-1.02 (m, 20H), 0.88-0.61 (m, 10H);

¹¹B NMR (128.4 MHz, CDCl₃) δ=~-4 (broad) ppm.

¹⁹F NMR (376 MHz, CDCl₃) δ=-131.48 (dd, J=22.56, 7.90, 4F), -156.17 (d, J=20.68, 2F), -162.31 (m, 4F);

Synthesis of 22

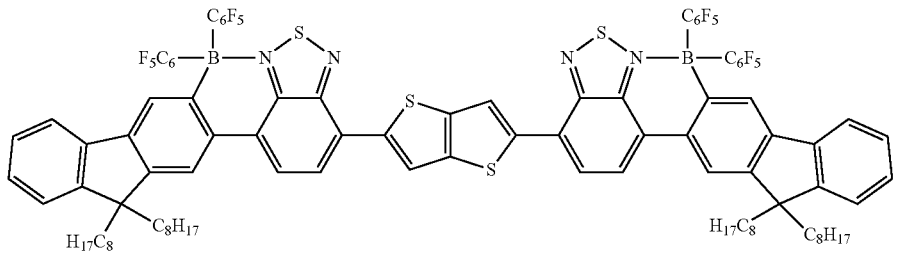

A mixture of compound 21 (150 mg, 0.16 mmol), 2,5-Bis(tributylstannyl)-thieno[3,2-b]thiophene (56 mg, 0.8 mmol) and Pd(PPh₃)₄ (17 mg, 0.016 mmol) was dissolved in toluene (4 mL) and heated at 100° C. for 40 hours. After evaporating the solvent, the residue was purified by column chromatography on silica gel [eluent: hexane/DCM (6/4)] to afford 22 as a dark green residue. (yield 51 mg, 35%).

¹H NMR (400 MHz, CDCl₃) δ=8.53-8.43 (m, 4H), 8.16 (d, J=7.8 Hz, 2H), 8.03 (s, 2H), 7.78 (s, 2H), 7.74-7.65 (m, 2H), 7.40-7.29 (m, 6H), 2.06 (t, J=8.2 Hz, 8H), 1.23-1.01 (m, 40H), 0.85-0.62 (m, 20H);

¹⁹F NMR (376 MHz, CDCl₃) δ=-131.52 (dd, J=24.06, 8.65, 4F), -156.32 (t, 20.30, 2F), -162.42 (m, 8F)

Synthesis of 23

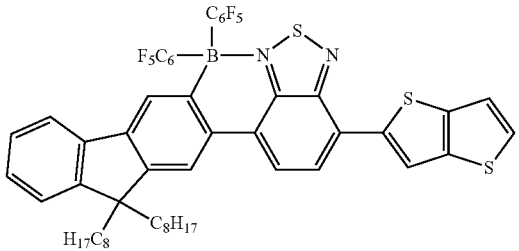

23 was isolated from the reaction mixture of 22.

¹H NMR (400 MHz, CDCl₃) δ=8.45-8.38 (m, 2H), 8.08 (d, J=7.8 Hz, 1H), 8.02 (s, 1H), 7.78 (s, 1H), 7.73-7.64 (m, 1H), 7.51 (d, J=5.3 Hz, 1H), 7.40-7.28 (m, 3H), 2.06 (t, J=8.2 Hz, 4H), 1.23-1.01 (m, 20H), 0.85-0.60 (m, 10H);

¹³C NMR (101 MHz, CDCl₃) δ=152.0, 151.3, 150.3, 147.7, 143.1, 140.6, 140.3, 140.1, 139.0, 129.5, 128.5, 128.0, 127.9, 127.7, 126.9, 125.9, 125.6, 124.3, 122.9, 121.0, 120.4, 119.6, 116.3, 55.0, 40.6, 31.8, 30.0, 29.2, 29.1, 23.8, 22.5, 14.0

¹⁹F NMR (376 MHz, CDCl₃) δ=-131.51 (dd, J=22.56, 8.65, 4F), -156.32 (t, 20.30, 2F), -162.49 (m, 8F)

Synthesis of 24

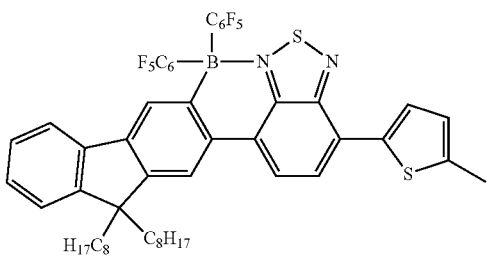

A mixture of compound 21 (80 mg, 0.84 mmol), trimethyl (5-methyl-2-thienyl)-stannane (25 mg, 0.95 mmol) and Pd(PPh₃)₄ (4 mg, 0.004 mmol) was dissolved in THF (1 mL) and heated at 80° C. for 20 hours. After evaporating the solvent, the residue was purified by preparative silica gel TLC [eluent: hexane/DCM (8/2)] to afford 24 as a dark blue residue. Yield 75 mg, 92%.

¹H NMR (400 MHz, CDCl₃) δ=8.41 (d, J=7.8 Hz, 1H), 8.01 (s, 1H), 8.01 (d, J=7.6 Hz, 1H), 7.95 (d, J=3.8 Hz, 1H), 7.77 (s, 1H), 7.74-7.65 (m, 1H), 7.43-7.30 (m, 3H), 6.91 (d,

J=3.5 Hz, 1H), 2.61 (s, 3H), 2.06 (t, J=8.3 Hz, 4H), 1.27-1.01 (m, 20H), 0.86-0.62 (m, 10H);

$^{13}$C NMR (101 MHz, CDCl$_3$) δ=152.1, 151.3, 150.2, 147.6, 143.2, 142.8, 140.4, 135.0, 128.7, 128.1, 127.9, 127.6, 127.1, 127.0, 126.8, 125.9, 125.8, 124.2, 122.9, 120.3, 116.2, 55.0, 40.6, 31.8, 30.0, 29.2, 29.1, 23.7, 22.5, 15.5, 14.0

$^{19}$F NMR (376 MHz, CDCl$_3$) δ=−131.55 (dd, J=22.56, 8.65, 4F), −156.32 (t, 20.68, 2F), −162.60 (m, 8F)

Synthesis of 25

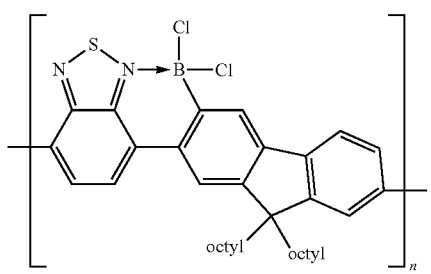

BCl$_3$ (1M solution in hexane) (0.015 mL, 0.015 mmol) was added to a solution of poly(9,9-dioctylfluorene-co-benzothiadiazole) poly-F8BT (8 mg, 0.015 mmols) in DCM (1 mL) in a Young's NMR tube resulting in a colour change from yellow to dark blue after rotating for 3 hours. NMR examination suggested the reaction was successful. The solvent was removed under reduced pressure to afford a dark blue residue.

$^1$H NMR (500 MHz, DCM) δ=8.71-8.63 (broad), 8.60-8.55 (broad), 8.53-8.47 (broad), 8.25-8.97 (m, broad), 2.30-2.04 (broad), 1.33-1.03 (m, broad), 0.91-0.74 (m, broad) ppm;

No peak was observable in the $^{11}$B NMR.

Synthesis of 26

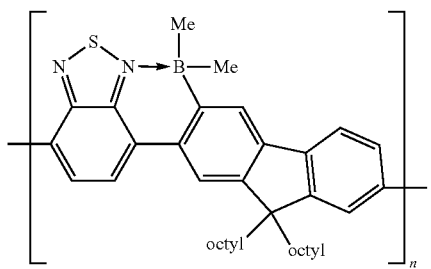

A solution of AlMe$_3$ (2M in heptanes) (0.11 mL, 0.22 mmol) in dry toluene (1 mL) was added to a stirred solution of 25 in dry toluene (4 mL). The solution changed colour from dark blue to purple and after 20 minutes the solvent and excess AlMe$_3$ was removed under reduced pressure this product was then precipitated in methanol. Yield 38 mg.

$^1$H NMR (400 MHz, CD$_2$Cl) δ=8.53-8.35 (m, 1H), 8.19-7.93 (m, 7H), 2.18 (br. s., 4H), 1.25-1.06 (m, 26H), 0.79 (t, J=6.3 Hz, 8H), 0.51 (br. s., 6H).

Synthesis of 27:

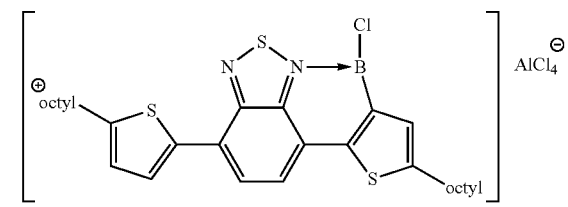

AlCl$_3$ (6 mg, 0.04 mmol) was added to a solution of 7 (25 mg, 0.04 mmol) in DCM (0.7 mL). The solution colour changed from dark blue to dark red.

$^1$H NMR (400 MHz, DCM): δ=8.66 (d, J=8.0, 1H), 8.37 (s, 1H), 8.14 (d, J=6.8, 1H), 7.14 (s, 1H), 7.14 (s, 1H), 3.09-2.92 (m, 4H), 1.86-1.73 (m, 4H), 1.49-1.19 (m, 20H), 0.87 (t, 6H) ppm;

$^{27}$Al NMR (104.3 MHz, DCM): δ=103 (broad) ppm.

No peak was observable in the $^{11}$B NMR.

Synthesis of 28

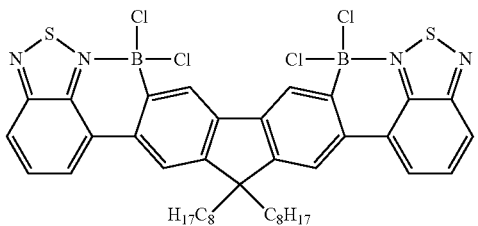

BCl$_3$ (1M solution in DCM) (0.40 mL, 0.40 mmol) was added to a bright yellow solution of 4,4'-(9,9-dioctyl-9H-fluorene-2,7-diyl)bis(benzo[c][1,2,5]thiadiazole) (BT-F8-BT) (66 mg, 0.01 mmol) in DCM (0.7 mL) in a Young's NMR tube. The solution instantly changed colour to a dark red. 2,4,6-Tri[t]butylpyridine (50 mg) and AlCl$_3$ (40 mg, 0.3 mmol) was added to the reaction mixture. After rotating for 16 hours, AlCl$_3$ (14 mg, 0.1 mmol) was added and the solution was rotated for a further 16 hours whereupon the solution had turned dark green. N[n]Bu$_4$Cl (48 mg, 0.2 mmol) was then added to the reaction mixture and the solution turned dark purple. NMR examination indicated the desired product had been formed.

$^1$H NMR (400 MHz, DCM) δ=8.71 (d, J=7.2 Hz, 2H), 8.46 (s, 2H), 8.04 (m, 2H), 8.31 (d, J=8.8 Hz, 2H), 8.16 (s, 2H), 2.22 (m, 4H), 0.72 (t, J=6.8 Hz, 6H) ppm;

Synthesis of 29

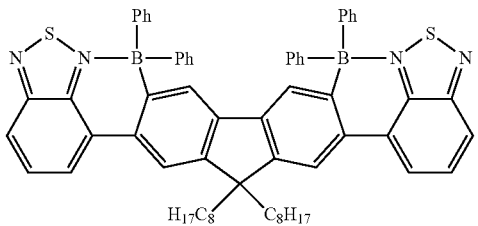

A reaction mixture containing 28 (0.45 mmol) and the ionic by-products from borylation (e.g., ammonium[AlCl$_4$]) was dissolved in DCM (15 mL) and ZnPh$_2$ (400 mg, 1.82 mmol) was added. The reaction mixture was then stirred for 16 hours after which it was passed through a plug of silica. The solvent was then removed under reduced pressure and the product was isolated by column chromatography on base treated [hexane/NEt$_3$ (95:5)] silica gel [eluent: hexane/DCM (8:2)] Yield (236 mg, 53%).

$^1$H NMR (400 MHz, CD$_2$Cl$_2$) δ=8.39 (d, J=7.1 Hz, 2H), 8.18 (s, 2H), 7.90-7.77 (m, 6H), 7.31-7.15 (m, 20H), 2.32-2.13 (m, 4H), 1.18 (m, 20H), 0.97 (m, 4H), 0.82 (t, J=6.7 Hz, 6H);

$^{13}$C NMR (101 MHz, CD$_2$Cl$_2$) δ=155.8, 155.3, 152.7, 150.4, 148.2, 142.4, 134.0, 133.7, 131.0, 130.4, 128.1, 126.5, 126.4, 123.9, 119.5, 117.3, 55.1, 41.3, 32.4, 30.7, 29.8, 24.7, 23.2, 14.4;

$^{11}$B NMR (128.4 MHz, CD$_2$Cl$_2$): δ=2.0 (Broad);

MALDI-TOF: calc. for C$_{59}$H$_{59}$B$_2$N$_4$S$_2$$^+$ [M−C$_6$H$_5$]$^+$ 909.9, found 910.0.

Synthesis of 30

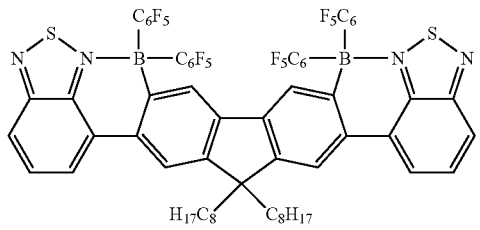

A reaction mixture of 28 (0.45 mmol) also containing the ionic by-products from borylation (e.g., ammonium[AlCl$_4$]) was dissolved in DCM (15 mL) and Zn(C$_6$F$_5$)$_2$ (728 mg, 1.82 mmol) was added. The reaction mixture was then stirred for 16 hours after which it was passed through a plug of silica. The solvent was then removed under reduced pressure and the product was isolated by column chromatography on base treated [hexane/NEt$_3$ (95:5)] silica gel [eluent: hexane/DCM (8:2)] Yield (435 mg, 71%).

$^1$H NMR (400 MHz, CD$_2$Cl$_2$) δ=8.48 (d, J=6.8 Hz, 2H), 8.10 (s, 2H), 8.02-7.85 (m, 4H), 7.67 (s, 2H), 2.25-2.05 (m, 4H), 1.20-1.00 (m, 20H), 0.78-0.68 (m, 10H);

$^{13}$C NMR (101 MHz, CDCl$_3$) δ=154.9, 150.7, 147.0, 142.2, 133.5, 129.7, 128.7, 125.0, 125.0, 119.4, 116.5, 55.0, 40.9, 31.8, 30.0, 29.2, 29.1, 22.5, 14.0;

$^{19}$F NMR (376 MHz, CDCl$_3$) δ=−132.23 (dd, J=22.56, 8.27, 8F), −157.83 (t, 20.68, 4F), −163.77 (m, 8F);

$^{11}$B NMR (128.4 MHz, CDCl$_3$): δ=3.0 (Broad);

MALDI-TOF: calc. for C$_{59}$H$_{44}$B$_2$F$_{15}$N$_4$S$_2$$^+$ [M−C$_6$F$_5$]$^+$ 1179.8, found 1179.7.

Synthesis of 31

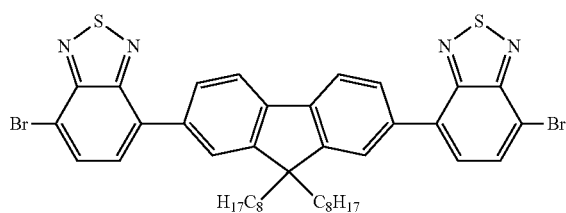

4,4'-(9,9-dioctyl-9H-fluorene-2,7-diyl)bis(benzo[c][1,2,5]thiadiazole) (BT-F8-BT) (512 mg, 0.78 mmol) was dissolved in chloroform (5 mL) and bromine (0.9 mL, 1.7 mmols) was added. The reaction mixture was then stirred for 18 hours after which the reaction mixture was quenched with Na$_2$S$_2$O$_3$ solution, washed with brine (50 mL) then water (50 mL), and dried (MgSO$_4$), The crude product was the purified via silica gel chromatography [eluent:hexane/EtOAc (98/2)] to afford 31 and a yellow solid. Yield (612 mg, 97%)

$^1$H NMR (400 MHz, CD$_2$Cl$_2$) δ=8.05-7.84 (m, 8H), 7.65 (d, J=7.6 Hz, 2H), 2.25-1.98 (m, 4H), 1.22-1.02 (m., 20H), 1.00-0.82 (m, 4H), 0.76 (t, J=6.7 Hz, 6H);

$^{13}$C NMR (101 MHz, CDCl$_3$) δ=153.7, 153.0, 151.6, 140.9, 135.4, 134.1, 132.1, 128.2, 127.8, 123.8, 120.1, 112.6, 55.3, 40.0, 31.6, 29.9, 29.1, 23.9, 22.5, 22.5, 14.0;

Synthesis of 32

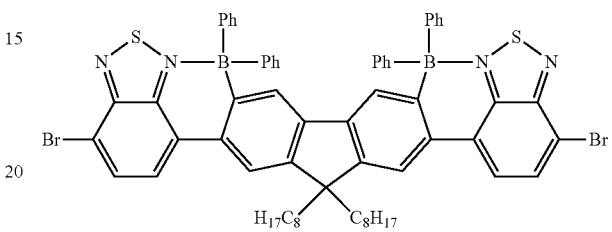

BCl$_3$ (1M in DCM) (4.5 mL, 4.5 mmols) was added to a solution of 31 (430 mg, 0.53 mmols) in DCM (5 mL). The reaction was stirred under the dynamic flow of nitrogen for 20 hours after which it was degassed and the solvent was removed under reduced pressure. The reaction mixture residue was dissolved in DCM (5 mL), ZnPh$_2$ (574 mg, 2.61 mmols) was then added to the reaction mixture. The reaction mixture was left to stir for 4 hours were it was diluted with DCM (5 mL) and the solution was passed through a plug of silica. The solvent was then removed under reduced pressure and the product was isolated via column chromatography on silica gel [eluent: Chloroform/hexane (7/3)] to afford 32 as a dark purple residue. (Yield 347 mg, 58%).

$^1$H NMR (400 MHz, CD$_2$Cl$_2$) δ=8.22 (d, J=7.95 Hz, 2H) 8.01-8.12 (m, 4H) 7.76 (s, 2H) 7.15-7.32 (m, 21H) 2.04-2.20 (m, 4H) 1.23 (br. s., 5H) 1.16 (br. s., 16H) 0.86-0.99 (m, 5H) 0.83 (t, J=6.72 Hz, 6H);

$^{13}$C NMR (101 MHz, CDCl$_3$) δ=154.3, 153.0, 152.1, 149.9, 147.7, 142.2, 135.3, 133.5, 130.0, 129.2, 127.6, 126.6, 126.1, 123.6, 116.4, 110.6, 54.3, 40.8, 31.8, 30.1, 29.2, 29.2, 24.1, 22.6, 14.1;

$^{11}$B NMR (128.4 MHz, CDCl$_3$): δ=~2.0 (Broad);

Synthesis of 33

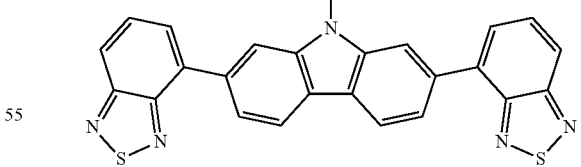

9-(heptadecan-9-yl)-2,7-bis(4,4,5,5-tetramethyl-1,3,2-dioxaborolan-2-yl)-9H-carbazole (0.62 g, 0.94 mmol. 1 eq) and bromobenzothiadiazole (0.46 g, 2.13 mmol, 2.2 eq) were degassed and dissolved in dry THF (10 mL). K$_3$PO$_4$.H$_2$O (1.30 g, 5.62, 6 eq), Pd$_2$(dba)$_3$ (42.9 mg, 0.047 mmol, 0.05 eq) and S-PHOS (38.5 mg, 0.094 mmol, 0.1 eq) were added to the reaction mixture; the red-brown solution turned green after mixing at r.t for 20 mins. Upon the addition of degassed H$_2$O the reaction mixture turned brown-orange then yellow. The reaction was stirred at 70° C. for 24 h. The cooled mixture was extracted with CH$_2$Cl$_2$, washed with brine water, then water, and dried with MgSO$_4$. After evaporation of solvents, the orange residue oil was purified by base treated silica gel (5% triethylamine, 95% hexane) chromatography (hexane followed by chloroform:hexane, 2:8) obtained yellow crystals. Yield (0.4857 g, 77%).

$^1$H NMR (400 MHz, CDCl$_3$) δ=0.78 (t, $^3J_{HH}$=8 Hz, 6H), 1.16 (m, br, 18H), 1.30 (m, br, 6H), 2.01 (m, br, 2H), 2.45 (m, br, 2H), 4.82 (m, br, 1H), 7.78 (m, $^3J_{HH}$=8 Hz, 4H), 7.85 (dd, br, 2H), 8.04 (dd, br, 2H), 8.10 (s, br, 1H), 8.29 (t, br, 2H);

$^{13}$C NMR (100 MHz, CDCl$_3$) δ=14.0, 22.5, 26.8, 29.2, 29.3, 29.4, 31.7, 33.8, 56.5, 110.3, 113.1, 120.1, 120.3, 120.5, 122.3, 123.6, 127.8, 129.7, 134.3, 134.9, 135.5, 139.4, 142.8, 153.8, 155.7;

Synthesis of 34

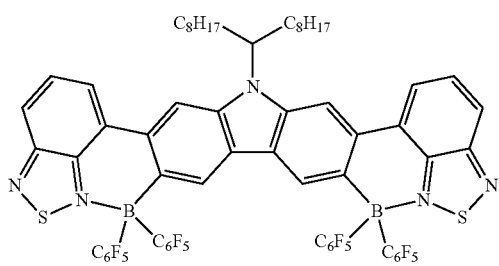

33 (100 mg, 0.1484 mmol, 1 eq) and tri-tert-butylpyridine (TBP) (73.4 mg, 0.2967 mmol, 2 eq) were dissolved in CH$_2$Cl$_2$ (3 mL), followed by the addition of BCl$_3$ in CH$_2$Cl$_2$ (0.6 mL, 1M, 4 eq). AlCl$_3$ (40 mg, 0.2967 mmol, 2 eq) was added and stirred for 2 h at r.t.; the red solution turned blue. An additional 2 eq of AlCl$_3$ was added and stirred for 2 h. Following the removal of excess BCl$_3$, the reaction mixture was redissolved in CH$_2$Cl$_2$ (5 mL) and NMe$_4$Cl (32.5 mg, 0.2967 mmol, 2 eq) was added. The solution instantly turned pink-purple. Subsequently, after the removal of CH$_2$Cl$_2$, the reaction mixture was redissolved in toluene (20 mL) and Zn(C$_6$F$_5$)$_2$ (237.4 mg, 0.5936 mmol, 4 eq) was added. The reaction was left to stir overnight at 60° C. which resulted in a purple solution. After evaporation, purification by a base treated (5% triethylamine 95% hexane) preparative TLC (Hexane:CH$_2$Cl$_2$, 7:3) a purple solid was obtained. Yield (47.7 mg, 0.035 mmol, 24%).

$^1$H NMR (400 MHz, CDCl$_3$) δ=0.76 (t, $^3J_{HH}$=8 Hz, 6H), 1.15 (m, br, 18H), 1.32 (m, br, 6H), 2.10 (m, br, 2H), 2.41 (m, br, 2H), 4.69 (m, br, 1H), 7.91 (br, 2H), 7.97 (br, 2H), 8.03 (br, 3H), 8.20 (s, br, 1H), 8.45 (br, 1H), 8.50 (br, 1H).

$^{13}$C NMR (100 MHz, CDCl$_3$) δ=14.0, 22.5, 27.0, 29.2, 29.3, 29.5, 31.7, 33.9, 56.5, 102.0, 104.7, 119.4, 121.6 (br), 124.4, 124.9, 125.2, 125.4, 125.7, 127.1, 127.5, 130.2, 133.4, 136.2 (br), 138.7 (br), 139.8, 141.4 (br), 143.1, 146.4 (br), 147.1, 148.8 (br), 155.0;

$^{19}$F NMR (376 MHz, CDCl$_3$)=−162.8 (m, 2F), −156.7 (m, 1F), −131.8 (d, $^3J_{FF}$=18.8 Hz, 2F).

Synthesis of 35

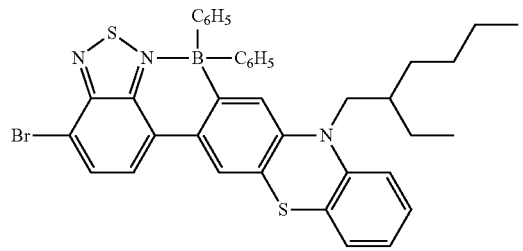

BCl$_3$ (1M in DCM) (0.4 mL, 0.4 mmol) was added to a stirred solution of 3-(7-bromobenzo[c][1,2,5]thiadiazol-4-yl)-10-(2-ethylhexyl)-1 OH-phenothiazine (33 mg, 0.06 mmols) in DCM (2 mL). The solution instantly changed colour from orange to dark blue. After 3 hours 2,4,6-tri-tert-butylpyridine (16 mg, 0.06 mmols) was added to the reaction mixture and the solution instantly changed colour from dark blue to dark green. After stirring for 16 hours the solvent and excess BCl$_3$ were removed under reduced pressure and the reaction mixture was redissolved in DCM (2 mL). Zn(Ph)$_2$ (31 mg, 0.14 mmols) was added to the reaction mixture and this was stirred for 3 hours. The reaction mixture was filtered through silica gel and purified by preparative silica gel TLC [eluent: hexane/DCM (8/2)] to afford 35 as a dark blue/green residue. Yield (17 mg, 39%)

$^1$H NMR (400 MHz, CDCl$_3$) δ=7.87 (d, J=7.8 Hz, 1H), 7.80 (d, J=7.9 Hz, 1H), 7.70 (s, 1H), 7.24-6.96 (m, 12H), 6.85-6.77 (m, 2H), 6.74 (d, J=8.1 Hz, 1H), 3.50 (d, J=6.7 Hz, 2H), 1.68 (td, J=6.1, 12.2 Hz, 1H), 1.25-0.95 (m, 8H), 0.72 (t, J=7.0 Hz, 3H), 0.63 (t, J=7.5 Hz, 3H);

$^{13}$C NMR (100 MHz, CDCl$_3$) δ=153.0, 147.5, 145.7, 145.6, 135.6, 133.6, 133.5, 128.9, 127.7, 127.4, 127.3, 126.2, 126.2, 124.6, 124.6, 124.2, 122.5, 122.3, 121.6, 121.3, 116.1, 109.9, 50.9, 35.6, 30.4, 28.3, 23.7, 23.0, 14.0, 10.3;

$^{11}$B NMR (128.4 MHz, CDCl$_3$): δ=2.0 (Broad);

Synthesis of 36

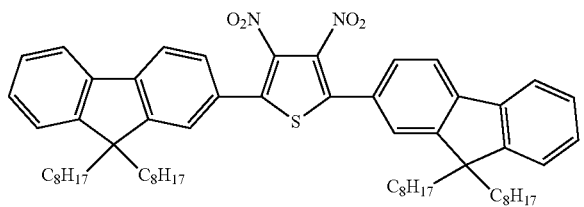

2,5-dibromo-3,4-dinitro-thiophene (1.01 g, 3.0 mmols), tri"butyl(9,9'-dioctyl-9H-fluoren-2-yl)-stannane (5.0 g, 7.3 mmols), Pd$_2$(dba)$_3$ (140 mg, 0.15 mmols) and S-Phos (264 mg, 0.6 mmols) were dissolved in THF (30 mL) and the reaction mixture was stirred at 70° C. for 20 hours. After cooling the reaction mixture was evaporated to dryness and purified using silica gel chromatography [eluent: Hexane/DCM (8/2)] to afford 36 as a light yellow solid. Yield (1.72 g, 59%)

$^1$H NMR (400 MHz, CDCl$_3$) δ=7.82 (d, J=7.6 Hz, 2H), 7.78 (dt, J=1.5, 3.9 Hz, 2H), 7.58-7.49 (m, 4H), 7.46-7.35 (m, 6H), 2.14-1.92 (m, 8H), 1.28-1.03 (m, 40H), 0.84 (t, J=7.1 Hz, 12H), 0.78-0.59 (m, 8H);

$^{13}$C NMR (101 MHz, CDCl$_3$) δ=151.6, 151.3, 143.9, 141.2, 139.6, 136.7, 128.3, 127.9, 127.1, 126.3, 123.6, 123.0, 120.4, 120.2, 77.3, 76.7, 55.4, 40.1, 31.7, 29.9, 29.2, 23.8, 22.6, 14.0;

Synthesis of 37

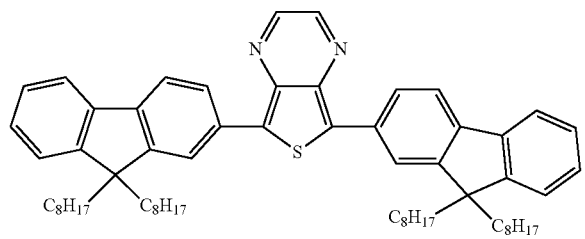

35 (300 mg, 0.32 mmols) was dissolved in a mixture of ethanol (18 mL) and toluene (6 mL). Tin powder (0.5 g, 2.5 mmols) was added to this solution and concentrated HCl (37%) (6 mL) was added drop wise to the suspension. The reaction mixture was then heated at 50° C. for 6 hours. The reaction mixture was then neutralised with aqueous NaOH (2M) and extracted with DCM (3×20 mL). The organic layers were combined and evaporated to dryness under reduced pressure. The reaction mixture was dissolved in DCM (10 ml) and trimethylamine (2 mL) was added. Glyoxal (40 wt. % in $H_2O$) (0.5 mL, 3.4 mmols) was added drop wise to the reaction mixture and was stirred for 16 hours. The reaction mixture was dried ($MgSO_4$) and evaporated to dryness under reduced pressure and purified using silica gel chromatography [eluent: hexane/DCM (8/2)] to afford 37 as a dark red residue. Yield (232 mg, 79%)

$^1$H NMR (400 MHz, $CDCl_3$) δ=8.59 (s, 2H), 8.31 (d, J=9.0 Hz, 2H), 8.11 (s, 2H), 7.84 (d, J=7.9 Hz, 2H), 7.77 (d, J=7.1 Hz, 2H), 7.44-7.31 (m, 6H), 2.17-1.96 (m, 8H), 1.26-1.02 (m, 40H), 0.87-0.65 (m, 20H);

Synthesis of 38

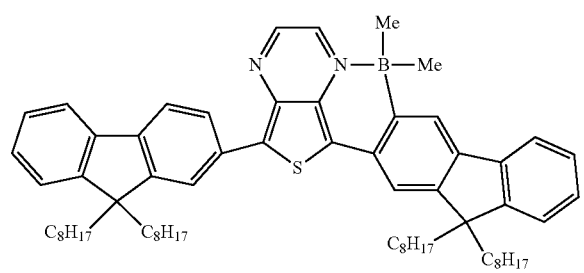

$BCl_3$ (1M in DCM) (0.1 mL, 0.1 mmols) was added to a stirred solution of 37 (57 mg, 0.06 mmols) in DCM (2 mL). The dark red solution instantly turned green and the solution was stirred for 10 minutes and then the excess $BCl_3$ and solvent was removed under reduced pressure. The resulting residue was dissolved in DCM (2 mL) and $AlMe_3$ (2M in heptanes) (0.1 mL, 0.2 mmols) was added to the reaction mixture. After 10 minutes the excess $AlMe_3$ and solvent was removed under reduced pressure. The resulting residue was purified by preparative silica gel TLC [eluent: hexane/DCM (8/2)] to afford 38 as a dark green residue. Yield (42 mg, 68%)

$^1$H NMR (400 MHz, $CDCl_3$) δ=8.76 (d, J=2.3 Hz, 1H), 8.31-8.18 (m, 2H), 8.08 (s, 1H), 7.89-7.72 (m, 4H), 7.60 (s, 1H), 7.43-7.28 (m, 6H), 2.17-1.91 (m, 8H), 1.24-1.13 (m, 14H), 1.09 (br. s., 29H), 0.80 (t, J=6.9 Hz, 22H), 0.34 (s, 6H);

Synthesis of 39

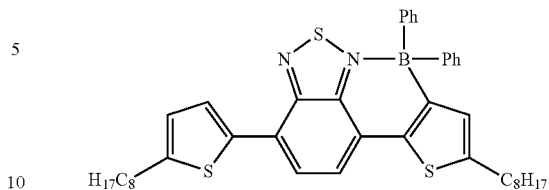

$BCl_3$ (1M solution in DCM) (0.12 mL, 0.12 mmol) was added to a bright orange solution of 2 (0.50 g, 0.1 mmol) in DCM (3 mL) in a Schlenk flask. The reaction mixture was stirred for 16 hours under a dynamic flow of nitrogen, where upon a colour change to dark blue was observed. The solvent and excess $BCl_3$ was removed under reduced pressure to yield a dark blue residue. The residue was redissolved in toluene and $Zn(Ph)_2$ (50 mg, 0.23 mmol) was then added to the reaction mixture and stirred for 3 hours the solution was then filtered through silica gel and the solvent was removed under reduced pressure to afford 39 as a dark blue residue. (Yield 46 mg, 69%).

$^1$H NMR (400 MHz, $CDCl_3$) δ=7.76 (d, J=3.7 Hz, 1H), 7.65 (d, J=7.6 Hz, 1H), 7.38 (d, J=7.7 Hz, 1H), 7.31-7.14 (m, 10H), 6.84-6.76 (m, 2H), 2.87 (t, J=7.6 Hz, 2H), 2.81 (t, J=7.6 Hz, 2H), 1.73 (quind, J=7.6, 15.1 Hz, 4H), 1.49-1.20 (m, 20H), 0.98-0.83 (m, 6H);

$^{13}$C NMR (101 MHz, $CDCl_3$) δ=160.7 (broad), 154.0 (broad), 151.5, 148.9, 147.8, 147.4, 135.4, 133.2, 130.9, 130.3, 127.9, 127.6, 127.3, 126.0, 125.4, 124.9, 123.6, 121.6, 31.9, 31.8, 31.6, 31.5, 30.5, 30.2, 29.3, 29.3, 29.2, 29.2, 29.1, 22.7, 14.1;

A number of the $\underline{C}H_2$ resonances were not distinctly observed due to similar magnetic environments.

$^{11}$B NMR (128.4 MHz, $CDCl_3$) δ=Not observed

MALDI-TOF: calc. for $C_{36}H_{44}BN_2S_3^+$ $[M-C_6H_5]^+$ 611.8, found 611.7.

Synthesis of 40

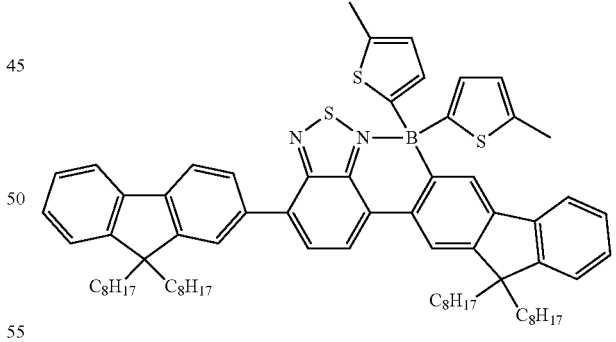

$BCl_3$ 1M solution in DCM (0.15 mL, 0.12 mmol) was added to a bright orange solution of 3 (0.095 g, 0.1 mmol) in DCM (3 mL) in a Schlenk flask. The reaction mixture was stirred for 16 hours where upon a colour change to dark blue was observed. The solvent and excess $BCl_3$ was removed under reduced pressure to yield a dark blue residue. 5-trimethylstannyl-2-methylthiophene (81 mg, 0.3 mmols) and $AlCl_3$ (1 mg) was added to the reaction mixture. The reaction mixture instantly changed from blue to purple. After stirring for 16 hours the reaction mixture was evaporated to dryness under reduced pressure and the residue was purified using base treated (5% NEt₃ in hexane) preparative silica gel TLC [eluent:hexane] to afford 40 as a purple residue. Yield (75 mg, 64%)
Synthesis of 41-43

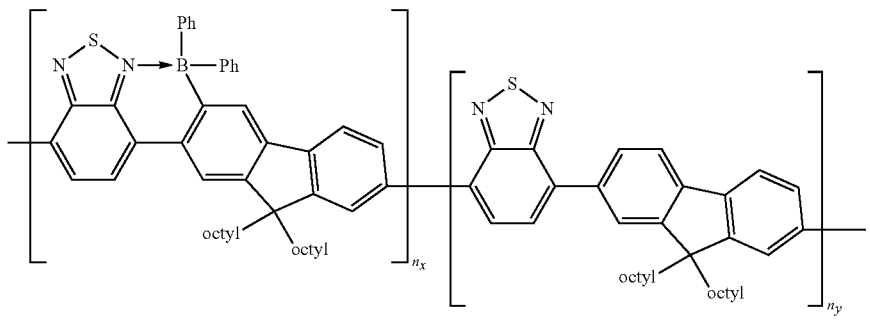

BCl₃ (1M in DCM) (X equivalents) and 2,4,6-tritertbutylpyridine (X equivalents) were added to a stirred solution of poly-F8BT in toluene. The reaction mixture was then stirred in a closed system for 16 hours. Zn(Ph)₂ (2.2× equivalents) was then added to the reaction mixture and the reaction mixture was stirred for 3 hours. The reaction mixture was then passed through a plug of silica and precipitated by drop wise addition of methanol.

41=80% borylated. Yield (390 mg)
¹H NMR (400 MHz, CDCl₃) δ=8.55-8.39 (m, 1H), 8.16-7.70 (m, 7.6H), 7.41-7.14 (m, 12H), 2.11 (br. s., 5.4H), 1.24-1.04 (m, 27H, 1.04-0.73 (m, 11H);
Mn=16000
42=42% borylated
43=25% borylated
Synthesis of 44

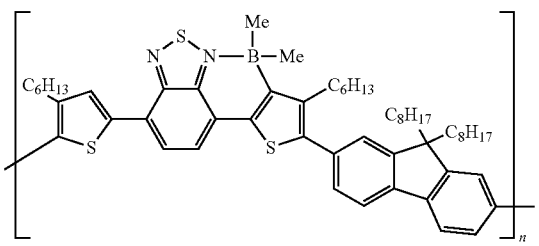

BCl₃ (1M in DCM) (0.3 mL, 0.3 mmols) was added to a solution of poly((9,9-dioctylfluorene)-2,7-diyl-alt-[4,7-bis (3-hexylthien-5-yl)-2,1,3-benzothiadiazole]-2',2"-diyl) (100 mg, 0.11 mmols) in toluene (10 mL) were the reaction mixture instantly changed colour from dark red to dark green. The reaction mixture was stirred under a dynamic flow of nitrogen for 16 hours. The reaction mixture was then degassed and AlMe₂ (2M in heptanes) (0.2 mL, 0.4 mmols) was added. The reaction mixture was stirred for 30 minutes and then degassed. The reaction mixture was then passed through a plug of silica and precipitated by addition of methanol. The resulting dark green powder was then purified by Soxhlet extraction using hexane, acetone and finally chloroform. The chloroform solution was then precipitated by addition of methanol and the resulting dark green powder was collected by filtration and dried. Yield (31 mg, 31%)
¹H NMR (400 MHz, CDCl₃) δ=8.03 (br. s., 1H), 7.92 (br. d., 1H), 7.80 (br. t., 2H), 7.64-7.49 (m, 5H), 2.90 (br. s., 2H), 2.82 (br. s., 2H), 2.05 (br. s., 4H), 1.54-1.03 (m, 48H), 0.96-0.69 (m, 20H), 0.51 (br, s, 6H);
Mn=33000
Synthesis of 45

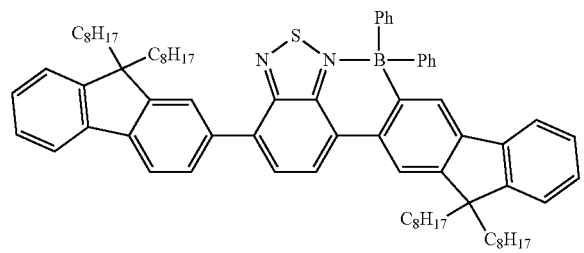

Zn(Ph)₂ (110 mg, 0.5 mmol) was added to a DCM (5 mL) solution of 14 (212 mg, 0.213 mmol, made in-situ as described above), the reaction was stirred for 3 hours and then the solution was filtered through silica gel and the solvent removed under reduced pressure to afford 45 as a dark purple residue. (Yield 231 mg, 0.213 mmol 99%).

¹H NMR (400 MHz, CDCl₃) δ=8.52 (d, J=7.8 Hz, 1H), 8.18 (s, 1H), 8.12 (d, J=7.6 Hz, 1H), 8.06 (s, 1H), 8.01 (d, J=7.9 Hz, 1H), 7.95 (d, J=8.0 Hz, 1H), 7.95 (s, 1H), 7.87 (dd, J=2.4, 5.4 Hz, 1H), 7.76-7.68 (m, 1H), 7.53-7.24 (m, 16H), 2.27-2.03 (m, 8H), 1.36-1.20 (m, 40H), 1.00-0.76 (m, 20H);

¹³C NMR (101 MHz, CDCl₃) δ=154.3, 153.0, 152.2, 151.3, 149.1, 147.8, 142.4, 140.7, 135.3, 133.6, 130.1, 128.9, 127.6, 127.4, 126.7, 126.1, 125.8, 123.5, 122.7, 120.6, 116.4, 110.5, 54.8, 40.6, 31.7, 30.0, 29.2, 29.1, 23.9, 22.5, 14.0

¹¹B NMR (128.4 MHz, CD₂Cl₂): δ=2.0 (Broad singlet);

A number of the $\underline{C}H_2$ or $\underline{C}H$ resonances were not distinctly observed due to similar magnetic environments.

MALDI-TOF: calc. for $C_{70}H_{88}BN_2S^+$ [M−C₆H₅]+ 1000.4, found 1000.5.

Synthesis of 46

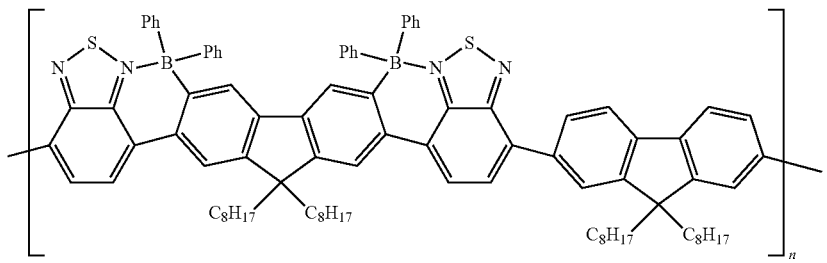

32 (70 mg, 0.06 mmols), 9,9-dioctylfluorene-2,7-diboronic acid (40 mg, 0.06 mmols) and bis(tri-tert-butylphosphine)palladium (8 mg, 0.016 mg) were dissolved in THF (5 mL) and 2M $K_3PO_4$ (0.62 mL, 0.12 mmols) was then added to the solution. The reaction mixture was stirred for 30 minutes at room temperature and then washed with water (30 mL) and dried ($MgSO_4$). The solution was concentrated under reduced pressure was precipitated in methanol. The resulting dark blue solid was collected by filtration and then dried. Yield (47 mg, 55%);
$^1$H NMR (400 MHz, $CDCl_3$) δ=8.47 (br. s., 2H), 8.24-7.87. (br. m., 10H), 7.76 (br. s., 3H), 7.32 (br. s., 11H), 7.24 (br. s., 17H), 2.25-1.96 (m, 7H), 1.31-0.68 (br. m., 80H); Mn=32000

EXAMPLE 2—ABSORPTION & EMISSION STUDIES

The UV-Vis absorption spectra for solution ranging 0.5-$2\times10^{-5}$ were recorded on a Varian Cary 5000UV-Vis-NIR spectrophotometer, in DCM at room temperature. Fluorescence spectra were recorded on a Varian Cary Eclipse fluorometer for solution ranging 0.5-$2\times10^{-5}$ in DCM at room temperature. Fluorescence quantum yield was measured on toluene solutions and estimated by using cresyl violet as standard (QY=54% in methanol). Solid state fluorescence and absolute quantum yields were measured on spin coated films of polymer host/5 wt % emitter using a Hamamatsu C9920-02 Absolute quantum yield measurement system.

Figure 1:
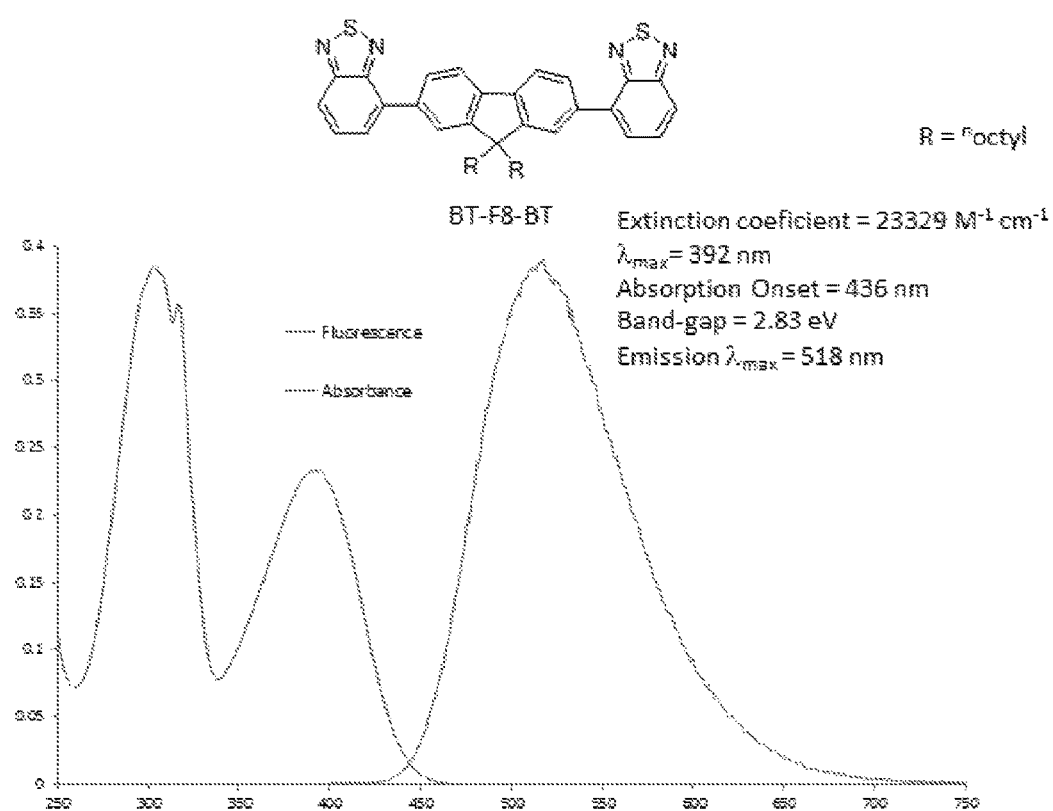
FIG. 1 shows absorption and emission spectra for the unborylated BT-F8-BT.
Figure 2:
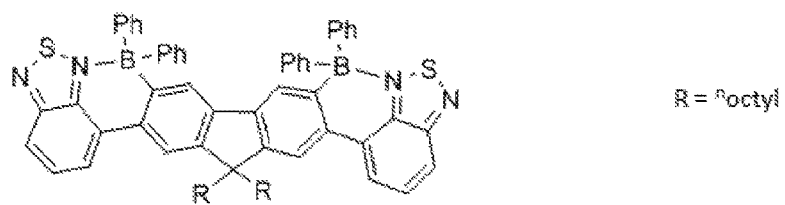
FIG. 2 shows absorption and emission spectra for borylated compound 29.
Figure 2:
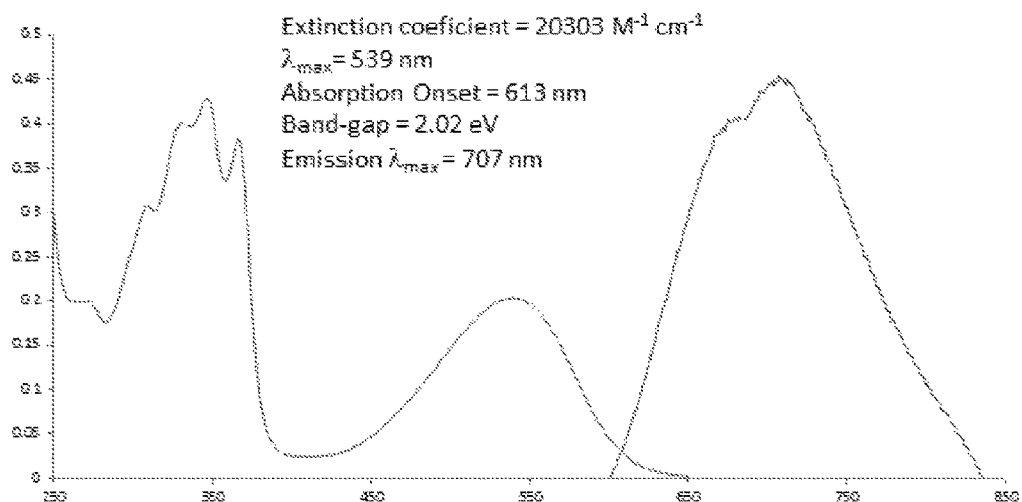
Figure 3:
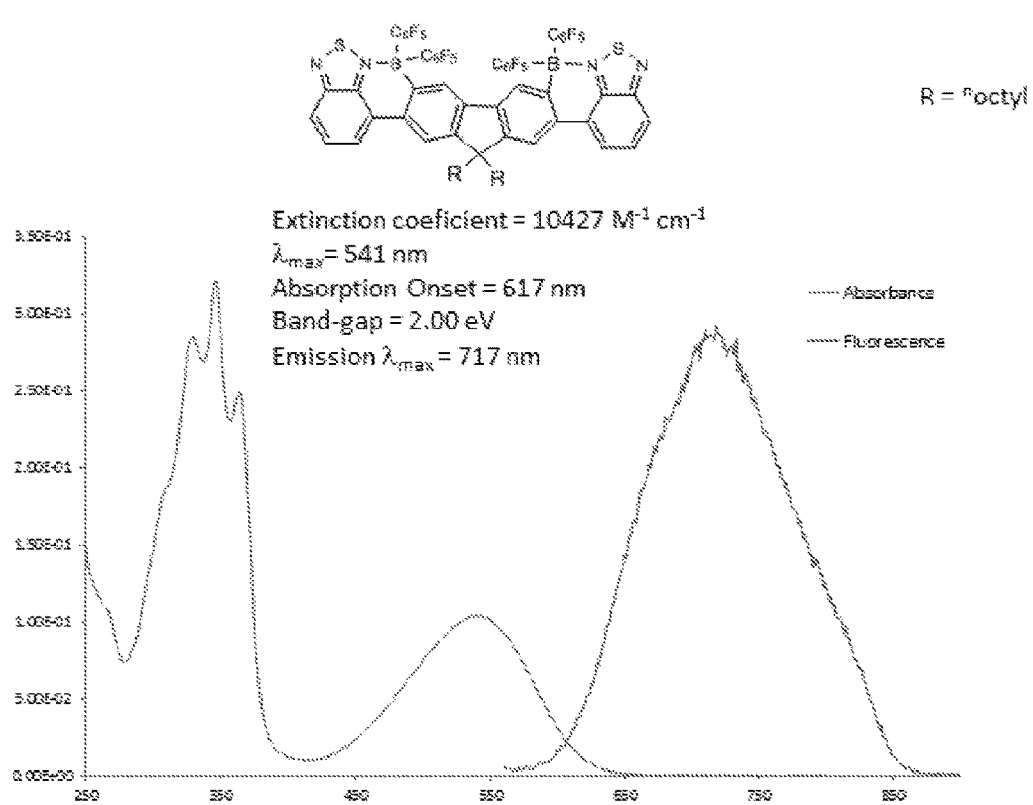
FIG. 3 shows absorption and emission spectra for borylated compound 30.
Figure 4:
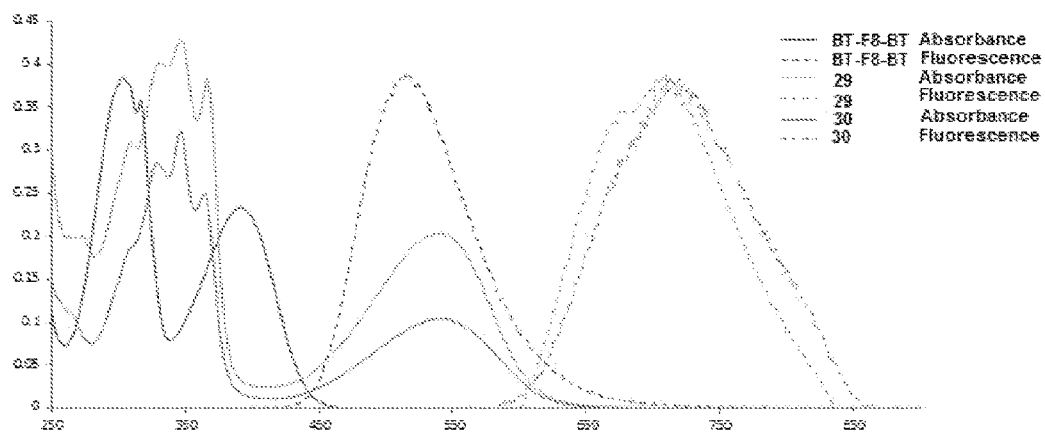
FIG. 4 shows a comparison of the absorption and emission spectra for unborylated BT-F8-BT and compounds 29 and 30.

FIG. 1 shows absorption and emission spectra for the unborylated BT-F8-BT. The compound was characterised as follows:
Extinction coefficient=23329 $M^{-1}$ $cm^{-1}$
$\lambda_{max}$=392 nm
Absorption Onset=436 nm
Band-gap=2.83 eV
Emission $\lambda_{max}$=518 nm
FIG. 2 shows absorption and emission spectra for borylated compound 29. The compound was characterised as follows
Extinction coefficient=20303 $M^{-1}$ $cm^{-1}$
$\lambda_{max}$=539 nm
Absorption Onset=613 nm
Band-gap=2.02 eV
Emission $\lambda_{max}$=707 nm
FIG. 3 shows absorption and emission spectra for borylated compound 30. The compound was characterised as follows:
Extinction coefficient=10427 $M^{-1}$ $cm^{-1}$
$\lambda_{max}$=541 nm
Absorption Onset=617 nm
Band-gap=2.00 eV
Emission $\lambda_{max}$=717 nm FIG. 4 and Table 1 below show a comparison of the absorption and emission spectra for unborylated BT-F8-BT and compounds 29 and 30.

TABLE 1

Comparison of absorption and emission data for unborylated BT-F8-BT and compounds 29 and 30

| | $\lambda_{abs}$ (nm) | $\lambda_{onset}$ (nm) | ε ($M^{-1}cm^{-1}$) | Band-Gap (eV) | $\lambda_{em}$ | QY |
|---|---|---|---|---|---|---|
| BT-F8-BT | 392 | 436 | 23329 | 2.83 | 593 | |
| 29 | 539 | 613 | 20303 | 2.02 | 707 | 0.18 |
| 30 | 541 | 617 | 10427 | 2.00 | 717 | 0.12 |

The above data show a significant reduction in optical band-gap and a large bathochromic shift in emission upon diborylation and formation a ladder structure. Whilst replacing $C_6F_5$ substituents on the boron for phenyl groups result little change in the UV-Vis absorbance spectra and emission $\lambda_{max}$, the phenyl substituted compound demonstrates much stronger fluorescence.

Figure 5:
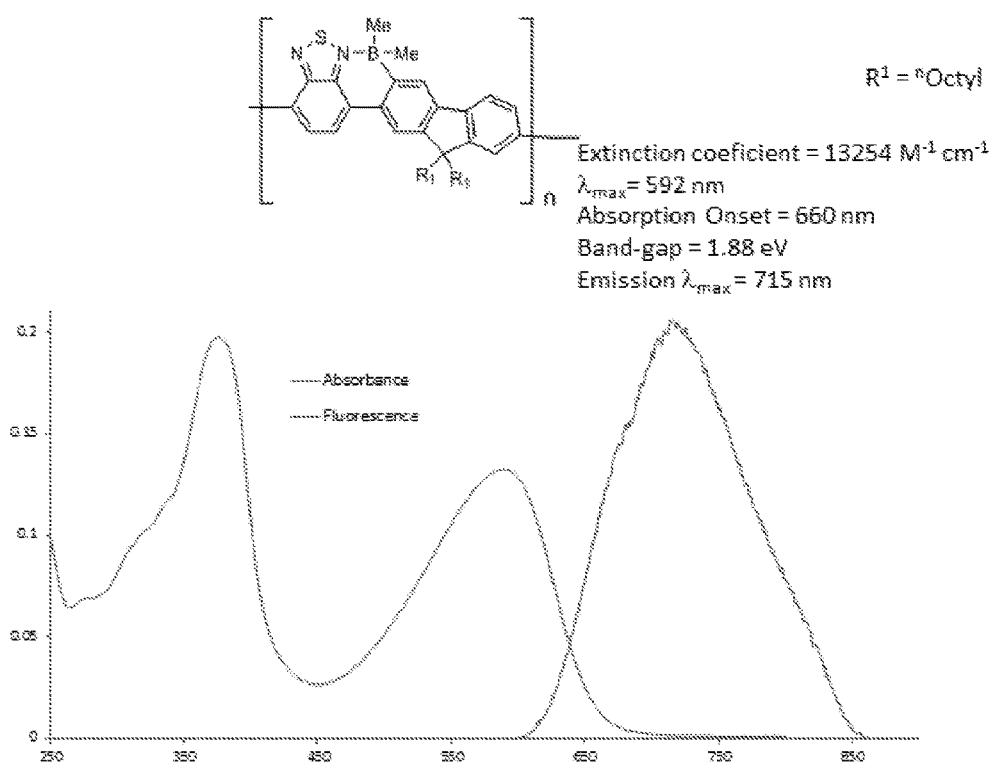
FIG. 5 shows absorption and emission spectra for borylated compound 26.

FIG. 5 shows absorption and emission spectra for borylated compound 26. The compound was characterised as follows:
Extinction coefficient=13254 $M^{-1}$ $cm^{-1}$
$\lambda_{max}$=592 nm
Absorption Onset=660 nm
Band-gap=1.88 eV
Emission $\lambda_{max}$=715 nm
The above data show a significant reduction in optical band-gap and a large bathochromic shift in emission upon borylation of F8BT. This polymer also exhibits some fluorescence in the solid state.

FIG. 6 shows the solid state photoluminescence spectra of thin films from a 5 wt % mixture of borylated compounds 45, 29 and 30 dispersed in PF8-BT polymer spin coated from toluene, excited at 468 nm.

| Film | Transmittance | PLQY % | CIE X | CIE Y |
|---|---|---|---|---|
| PF8-BT: 45 (95:5 wt %) | 0.36 | 33.5 | 0.660 | 0.338 |
| PF8-BT: 29 (95:5 wt %) | 0.36 | 32.9 | 0.633 | 0.360 |
| PF8-BT: 30 (95:5 wt %) | 0.36 | 19.9 | 0.628 | 0.368 |

FIG. 7 shows absorption and emission spectra for borylated compounds 41, 42 and 43 dissolved in toluene.

EXAMPLE 3—X-RAY ANALYSIS

Data for all compounds were recorded on either an Oxford Xcalibur Sapphire2 diffractometer, with Mo Kα radiation (graphite monochromator, λ=0.71073). The CrysAlisPro[5] software package was used for data collection, cell refinement and data reduction. Empirical absorption corrections were applied using spherical harmonics, implemented in SCALE3 ABSPACK scaling algorithm or a Bruker APEX-II diffractometer, with Cu Kα radiation (graphite monochromator, λ=1.54178). The Bruker APEX2 software package was used for data collection, and the Bruker SAINT[6] software package was used for cell refinement and data reduction. Empirical absorption corrections were applied using SADABS-2008/1—Bruker AXS area detector scaling and absorption correction. All structures were solved using direct methods[7] and refined against $F^2$ using the Crystals[8] software package. Non-hydrogen atoms were refined anisotropically. Hydrogen atoms were all located in a difference map and repositioned geometrically.

FIG. 8 shows the X-ray structure for the unborylated BT-F8-BT. The structure shows significant twisting between the neighbouring π-donor and π-acceptor units indicating unfavourable steric interactions.

FIG. 9 shows the X-ray structure for the borylated compound 29, wherein the $^n$octyl R substituents have been removed for clarity. FIG. 10 shows the X-ray packing structure of compounds 29. It is seen that proximal quaternary centres prevent core close packing, whilst peripheral BPh$_2$ π-π stack with the backbone, allowing 3D packing through close π-π contacts.

FIG. 11 shows the X-ray structure for the borylated compound 30. It can be seen that the torsion angle of adjacent π-donor and π-acceptor units is significantly reduced in relation to the unborylated BT-F8-BT. FIG. 12 shows the X-ray packing structure of compounds 30 wherein the $^n$octyl R substituents have been removed for clarity. It can be seen that C—F—C—F interactions dominate solid state packing, whilst no π-π stacking is observed due to the presence of proximal quaternary centres.

FIG. 13 shows the X-ray structure for the borylated compound 22. FIG. 14 shows the X-ray packing structure of compounds 22. This compound is seen to have a similar packing structure to that of the $C_6F_5$ substituted ladder compound (compound 30) with C—F—C—F interactions dominating the solid state packing. No π-π stacking was observed.

FIG. 15 shows the X-ray structure for the borylated compound 35. π-π stacking interactions were observed.

EXAMPLE 4—COMPUTATIONAL ANALYSIS

Samples were optimised at the M06-2x/6311G(dp) level using Gaussian 09 and confirmed to have zero imaginary frequencies.

FIG. 16 shows computational modelling of the molecular orbital of compound 29. It can be seen that the HOMO is located mainly on fluorene, with no HOMO character on the peripheral phenyl groups. The LUMO is seen to be located exclusively on benzothiadiazole, with no LUMO character observed on the peripheral phenyl groups.

EXAMPLE 5—CYCLIC VOLTAMMETRY

Cyclic voltammetry was performed using a CH-Instrument 1110C Electrochemical/Analyzer potentiostat under a nitrogen flow. Measurements were made using a 0.001 M analyte solution with 0.1 M tetrabutylammonium hexafluorophosphate (Fluka ≥99.0%) as the supporting electrolyte in distilled methylene chloride that had been degassed prior to use and obtained from a dry solvent system. A glassy carbon served as the working electrode and a platinum wire as the counter electrode. An Ag/AgNO$_3$ non-aqueous reference electrode was used. All scans were calibrated against the ferrocene/ferrocenium (Fc/Fc$^+$) redox couple, which in this work is taken to be 5.39 eV below vacuum [9]. The half-wave potential of the ferrocene/ferrocenium (Fc/Fc$^+$) redox couple ($E_{1/2, Fc,Fc+}$) was estimated from $E_{1/2, Fc,Fc+}=(E_{ap}+E_{cp})/2$, where $E_{ap}$ and $E_{cp}$ are the anodic and cathodic peak potentials, respectively.

FIG. 17 shows the cyclic voltammogram for compound 22. Data extracted from the scan is provided in Table 2 below.

TABLE 2

| Cyclic voltammogram for compound 22 | | | | | |
|---|---|---|---|---|---|
| | $E_{red}^{onset}$ (V) | $E_{ox}^{onset}$ (V) | HOMO (eV) | LUMO (eV) | Gap$_{HOMO-LUMO}$ (eV) |
| Compound vs Fc/Fc$^+$ | −0.946 | 0.630 | −6.02 | −4.44 | 1.58 |

Cyclic voltammetry measurement of this molecule show 2 reversible oxidation peaks and at least 1 reversible reduction peak. This molecule demonstrates an extremely low LUMO of −4.44 eV.

FIG. 18 and Table 3 show the cyclic voltammograms for compounds 2, 9, 11, 39, and 12. This series shows the modulation of the frontier molecular orbital energies possible by varying the substituents on boron.

TABLE 3

| Cyclic voltammograms for compounds 2, 9, 11, 39, and 12 | | | | | | | | |
|---|---|---|---|---|---|---|---|---|
| Compound | λmax$_{abs}$ (nm)$^a$ | ε (M$^{-1}$ cm$^{-1}$)$^a$ | Optical Band Gap (eV)$^b$ | $E_{ox}^{onset}$ (V)$^c$ | $E_{red}^{onset}$ (V)$^c$ | HOMO (eV)$^c$ | LUMO (eV)$^c$ | Electrochemical Band Gap (eV) |
| 2 | 471 | 15700 | 2.29 | 0.60 | −1.66 | −6.00 | −3.73 | 2.27 |
| 9 | 602 | 9700 | 1.73 | 0.46 | −1.33 | −5.85 | −4.06 | 1.79 |
| 11 | 611 | 9800 | 1.72 | 0.52 | −1.30 | −5.91 | −4.09 | 1.82 |
| 39 | 617 | 12600 | 1.70 | 0.57 | −1.24 | −5.96 | −4.15 | 1.81 |
| 12 | 641 | 7800 | 1.60 | 0.67 | −1.05 | −6.07 | −4.34 | 1.73 |

$^a$1 × 10$^{-5}$M solution in toluene.
$^b$Band gap estimated from onset of absorption.
$^c$Measured in DCM, (1 nM), with [nBu$_4$N][PF$_6$] (0.1M) as the supporting electrolyte at a scan rate of 50 mV/s, potentials are given relative to Fc/Fc$^+$ redox couple which is taken to be 5.39 eV below vacuum.

EXAMPLE 6—OLED DEVICE STUDIES

A series of un-optimised OLED devices (devices 1-4, Table 4) were fabricated by solution processing. The emission layer (EmL) was deposited from a toluene solution containing 5 wt % of the appropriate borylated compound in 80 wt % PF8-BT/15 wt % PF8TFB (PF8TFB=Poly[(9,9-dioctylfluorenyl-2,7-diyl)-co-(4,4'-(N-(4-sec-butylphenyl) diphenylamine)]), with the latter used to improve hole transport. The devices were constructed as follows, ITO (45 nm)/Plexcore OC® (65 nm)/PF8-TFB (22 nm)/EmL (100 nm)/Ba (3.5 nm) An additional device was fabricated where the EmL was deposited from a solution containing only 5 wt % of 45 and 95% of PF8-BT (i.e. in the absence of hole transport material PF8TFB, device 4).

TABLE 4

Summary of OLED device performance

| Compound X | PL λmax/nm (QY/%)$^a$ | Device$^b$ | EL λ max/nm$^c$ | $V_{on}{}^d$/V | EQE$^e$(%) |
|---|---|---|---|---|---|
| 45 | 696 (34) | 1 | 678 | 2.3 | 0.46 |
| 29 | 651 (33) | 2 | 634 | 2.1 | 0.14 |
| 30 | 673 (20) | 3 | 643 | 2.2 | 0.13 |
| 45 | 696 (34) | 4$^f$ | 679 | 2.5 | 0.48 |

$^a$= Photoluminescence of a film deposited from a 5/95 wt % solution of compound X/PF8-BT. Excitation at 468 nm and quantum yields determined using an integrating sphere.
$^b$OLED device structure: ITO (45 nm)/Plexcore OC (65 nm)/PF8-TFB (22 nm)/emissive layer (100 nm 85% PF8-BT/15% PF8-TFB/5% Compound X)/Ba (3.5 nm).
$^c$= electroluminescence emission maxima.
$^d$Turn-on voltage.
$^e$maximum external quantum efficiency.
$^f$emissive layer 95:5 wt % PF8BT/2-BPh$_2$.

All devices possessed low turn-on voltages and showed electroluminescence spectra similar to their photoluminescence data in PF8-BT hosts, albeit with slightly blue shifted emission maxima (18-30 nm). Devices 1 and 4, both containing 45 as the emitter, showed the highest maximum EQE values (0.46 and 0.48%, respectively) of the series of compounds with a $\lambda_{max}$ of 678 nm and a broad emission stretching into the NIR. All devices showed minimal green emission from the F8-BT host except device 2 where this emission was significant.

While specific embodiments of the invention have been described herein for the purpose of reference and illustration, various modifications will be apparent to a person skilled in the art without departing from the scope of the invention as defined by the appended claims.

REFERENCES

1. K. Colladet, S, Fourier, T. J. Cleij, L. Lutsen, J. Gelan, D. Vanderzande, L. H. Nguyen, H. Neugebauer, S. Sariciftci, A. Aguirre, G. Janssen and E. Goovaerts, *Macromolecules* 2007, 40, 65-72.
2. Van Mullekom, H. A. M.; Vekemans, J. A. J. M.; Havinga, E. E.; Meijer, E. W. Mater. Sci. Eng., R 2001, 32, 1-40.
3. G. C. Welch and G. C. Bazan, *J. Am. Chem. Soc.,* 2011, 133 (12), 4632-4644.
4. Poverenov, N. Zamoshchik, A. Patra, Y. Ridelman and M. Bendikov, J. Am. Chem. Soc. 2014, 136, 5138-5149.
5. CrysAlisPro, Agilent Technologies, Version 1.171.35.19 (release 27 Oct. 2011 CrysAlis171.NET) (compiled Oct. 27 2011, 15:02:11)
6. APEX2 V2012.2-0
7. SIR92, Altomare, A., Cascarano, G., Giacovazzo, C., Guagliardi, A., Burla, M. C., Polidori, G. & Camalli, M. (1994). J. Appl. Cryst. 27, 435.
8. Crystals, Version 14.40b, January 2012, Betteridge, P. W., Carruthers, J. R., Cooper, R. I., Prout, K. & Watkin, D. J. (2003). J. Appl. Cryst. 36, 1487.
9. C. M. Cardona, W. Li, A. E. Kaifer, D. Stockdale, G. C. Bazan, *Adv. Mater.* 2011, 23, 2367-2371.

The invention claimed is:
1. A compound comprising one or more moieties of formulae (I)-(V):

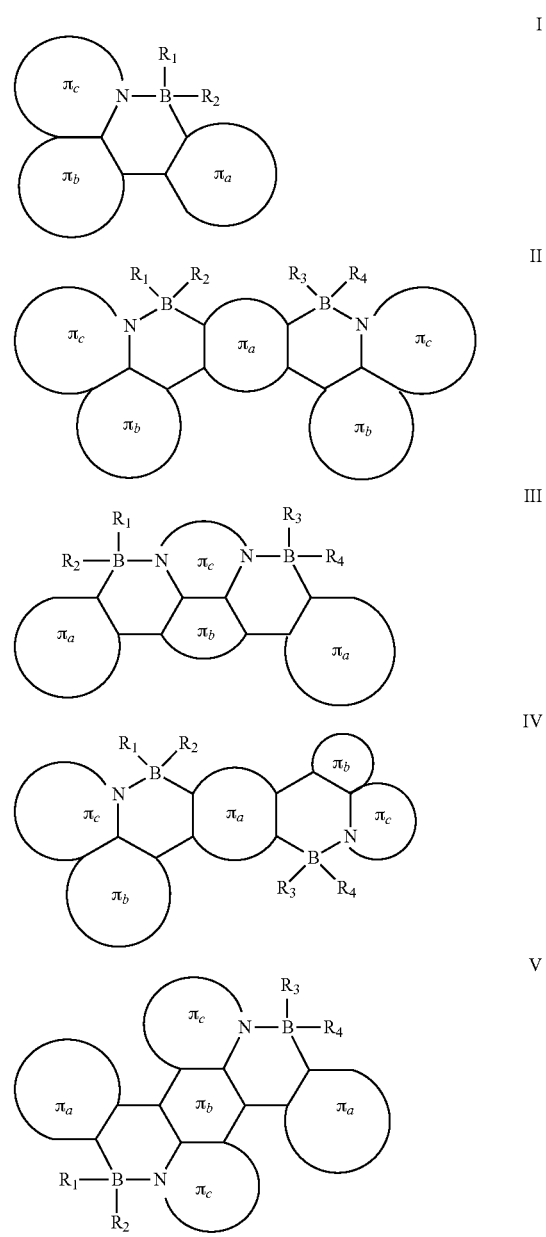

wherein:
R$_1$, R$_2$, R$_3$ and R$_4$ are each independently selected from the group consisting of hydrogen, fluoro, chloro, bromo, substituted or unsubstituted (1-10C)alkyl, substituted or unsubstituted (2-10C)alkenyl, substituted or unsubstituted (2-10C)alkynyl, substituted or unsubstituted aryl, substituted or unsubstituted heteroaryl, substituted or unsubstituted amino, substituted or unsubstituted (1-10C)alkoxy, substituted or unsubstituted arylalkoxy, and hydroxyl;

each $\pi_a$ independently is a π-conjugated π-donor ring system formed from one, two, three or four rings selected from the group consisting of 6-membered aryl rings and 5 to 6-membered heteroaryl rings;

when taken in combination, each $\pi_b$ and $\pi_c$ independently forms a moiety $\pi_{bc}$ selected from the group consisting of:

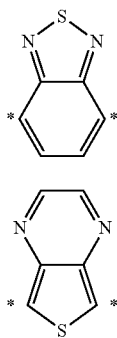

wherein moieties $\pi_{bc1}$ and $\pi_{bc4}$ are directly bonded to 1 or 2 boron atoms via either or both nitrogen atoms respectively;

moieties $\pi_{bc1}$ and $\pi_{bc4}$ are directly bonded to 1 or 2 $\pi_a$ moieties via either or both C*;

any or all of the rings forming $\pi_a$ and $\pi_{bc}$ may be independently optionally substituted with one more ring substituents selected from the group consisting of halo, (1-20C)alkyl, (2-20C)alkenyl, (2-20C)alkynyl, aryl, heteroaryl, cycloalkyl, heterocyclyl, carboxyl, phosphoryl, sulfonyl, hydroxyl, (1-20C)alkoxy, nitro, amino, mercapto, silyl, siloxy, azido, boronic acid group, sulfonic acid group, hydroxamic acid group, cyanoacrylate group, and dioxocyclobutenyl group having at least one functional group selected from the group consisting of a carboxyl, phosphoryl, sulfonyl, hydroxyl, alkoxy, nitro, amino, mercapto, silyl, siloxy, azido, boronic acid group, sulfonic acid group, hydroxamic acid group and cyanoacrylate group, and the bond linking B to N in the moieties of formulae (I)-(V) is covalent or coordinate covalent.

2. The compound of claim 1, wherein any or all of the rings forming $\pi_a$ and $\pi_{bc}$ may be independently optionally substituted with one more ring substituents selected from the group consisting of halo, (1-10C)alkyl, (2-10C)alkenyl, (2-10C)alkynyl, aryl, heteroaryl, cycloalkyl, heterocyclyl, carboxyl, hydroxyl, (1-10C)alkoxy and amino.

3. The compound of claim 1, wherein any or all of the rings forming $\pi_a$ and $\pi_{bc}$ may be independently optionally substituted with one more ring substituents selected from the group consisting of halo, (1-10C)alkyl, (2-10C)alkenyl, (2-10C)alkynyl, aryl, heteroaryl, cycloalkyl and heterocyclyl.

4. The compound of claim 1, wherein any or all of the rings forming $\pi_a$ may be independently optionally substituted with one or more ring substituents selected from the group consisting of bromo and (1-8C)alkyl.

5. The compound of claim 1, wherein $R_1$, $R_2$, $R_3$ and $R_4$ are each independently selected from the group consisting of hydrogen, fluoro, chloro, bromo, substituted or unsubstituted (1-10C)alkyl, substituted or unsubstituted (2-10C)alkenyl, substituted or unsubstituted (2-10C)alkynyl, substituted or unsubstituted aryl, substituted or unsubstituted heteroaryl, and hydroxyl.

6. The compound of claim 1, wherein $R_1$, $R_2$, $R_3$ and $R_4$ are each independently selected from the group consisting of hydrogen, fluorine, substituted or unsubstituted (1-10C) alkyl, substituted or unsubstituted aryl, substituted or unsubstituted heteroaryl, and hydroxyl.

7. The compound of claim 1, wherein when taken in combination, each $\pi_b$ and $\pi_c$ independently forms the moiety $\pi_{bc1}$ shown below:

wherein each moiety $\pi_{bc1}$ is independently optionally substituted with one or more ring substituents selected from the group consisting of halo, (1-20C)alkyl, (2-20C)alkenyl, (2-20C)alkynyl, aryl, heteroaryl, cycloalkyl, heterocyclyl, carboxyl, phosphoryl, sulfonyl, hydroxyl, (1-20C)alkoxy, nitro, amino, mercapto, silyl, siloxy, azido, boronic acid group, sulfonic acid group, hydroxamic acid group, cyanoacrylate group, and dioxocyclobutenyl group having at least one functional group selected from the group consisting of a carboxyl, phosphoryl, sulfonyl, hydroxyl, alkoxy, nitro, amino, mercapto, silyl, siloxy, azido, boronic acid group, sulfonic acid group, hydroxamic acid group and cyanoacrylate group.

8. The compound of claim 1, wherein each $\pi_a$ is independently formed from one, two or three rings selected from the group consisting of 6-membered aryl rings and 5 to 6-membered heteroaryl rings, and wherein any or all of the rings are optionally substituted with one or more ring substituents as claimed in claim 1.

9. The compound of claim 1, wherein each $\pi_a$ is a moiety independently selected from the group consisting of:

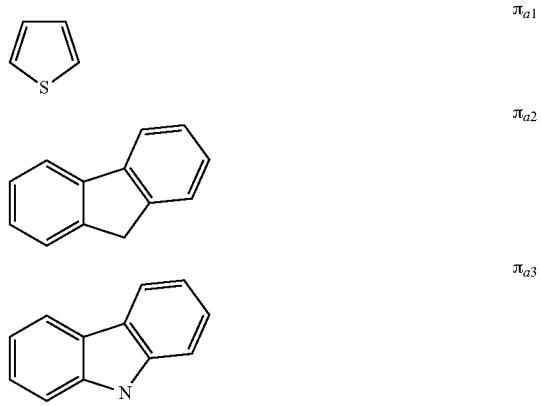

-continued

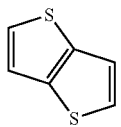
π_{a4}

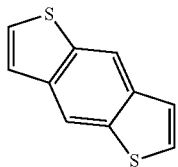
π_{a5}

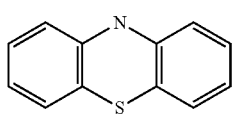
π_{a6} wherein moieties $\pi_{a1}$, $\pi_{a2}$, $\pi_{a3}$, $\pi_{a4}$, $\pi_{a5}$ and $\pi_{a6}$ are independently optionally substituted with one or more ring substituents as claimed in claim 1.

10. The compound of claim 1, wherein each $\pi_a$ is a moiety independently selected from the group consisting of:

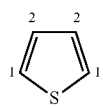
π_{a1}

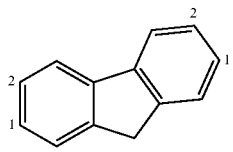
π_{a2}

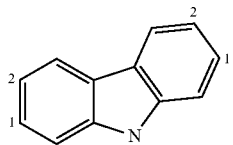
π_{a3}

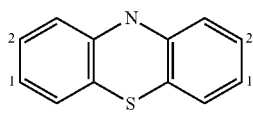
π_{a6} wherein
i) moieties $\pi_{a1}$, $\pi_{a2}$, $\pi_{a3}$ and $\pi_{a6}$ are directly bonded to 1 or 2 $\pi_b$ moieties via either or both of C1; and
moieties $\pi_{a1}$, $\pi_{a2}$, $\pi_{a3}$ and $\pi_{a6}$ are directly bonded to 1 or 2 boron atoms via either or both of C2;
or
ii) moieties $\pi_{a1}$, $\pi_{a2}$, $\pi_{a3}$ and $\pi_{a6}$ are directly bonded to 1 or 2 $\pi_b$ moieties via either or both of C2; and
moieties $\pi_{a1}$, $\pi_{a2}$, $\pi_{a3}$ and $\pi_{a6}$ are directly bonded to 1 or 2 boron atoms via either or both of C1;
and
moieties $\pi_{a1}$, $\pi_{a2}$, $\pi_{a3}$ and $\pi_{a6}$ are independently optionally substituted with one or more ring substituents as claimed in claim 1.

11. The compound of claim 1, wherein the compound comprises one or more moieties selected from the group consisting of:

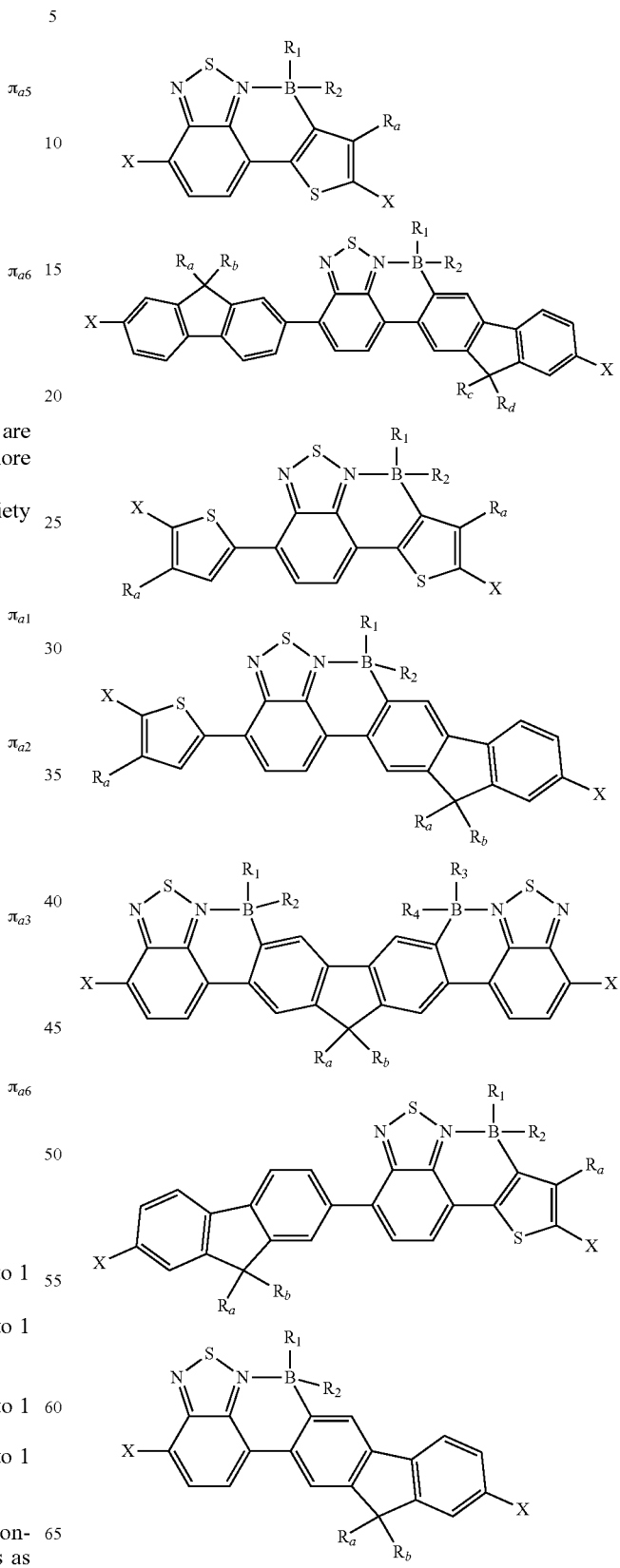

-continued

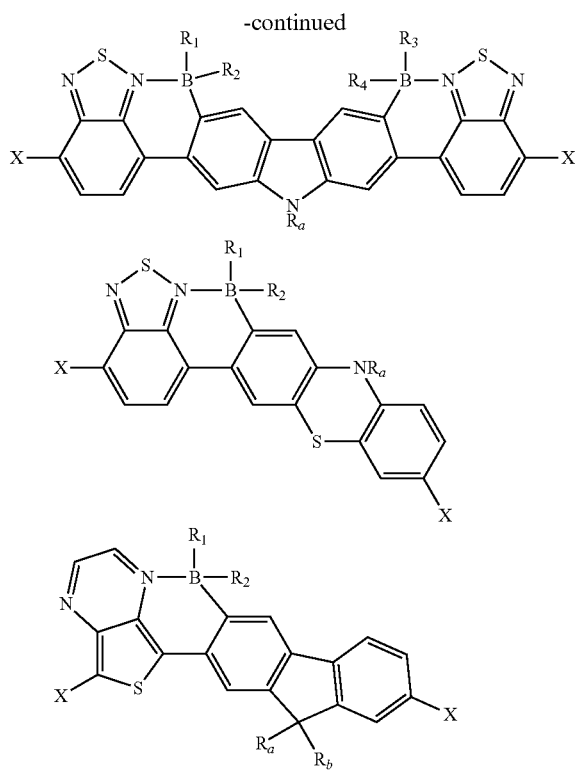

wherein $R_1$, $R_2$, $R_3$ and $R_4$ are independently as defined in claim 1;

$R_a$, $R_b$, $R_c$ and $R_d$ are independently selected from the group consisting of hydrogen, (1-20C)alkyl, (2-20C)alkenyl and (2-20C)alkynyl; and each X is hydrogen, or is independently:

(i) bromo, (1-10C)alkyl, (2-10C)alkenyl or (2-10C) alkynyl; or (ii) another moiety having one of the structural formulae defined above.

12. The compound of claim 11, wherein $R_1$, $R_2$, $R_3$ and $R_4$ are each independently selected from the group consisting of hydrogen, fluoro, chloro, bromo, substituted or unsubstituted (1-10C)alkyl, substituted or unsubstituted aryl, substituted or unsubstituted heteroaryl, and hydroxyl;

$R_a$, $R_b$, $R_c$ and $R_d$ are independently selected from the group consisting of hydrogen and (1-10C)alkyl; and each X is hydrogen, or is independently:

(i) bromo or (1-10C)alkyl; or (ii) another moiety having one of the structural formulae (I)-(V).

13. The compound of claim 1, wherein the compound is a polymer or oligomer comprising two or more moieties of formulae (I)-(V).

14. A method of preparing a compound comprising one or more moieties of any of formulae (I)-(V) as claimed in claim 1, the method comprising the steps of:

a) reacting a moiety of any of formulae (I')-(V') shown below with a reagent $BX_3$:

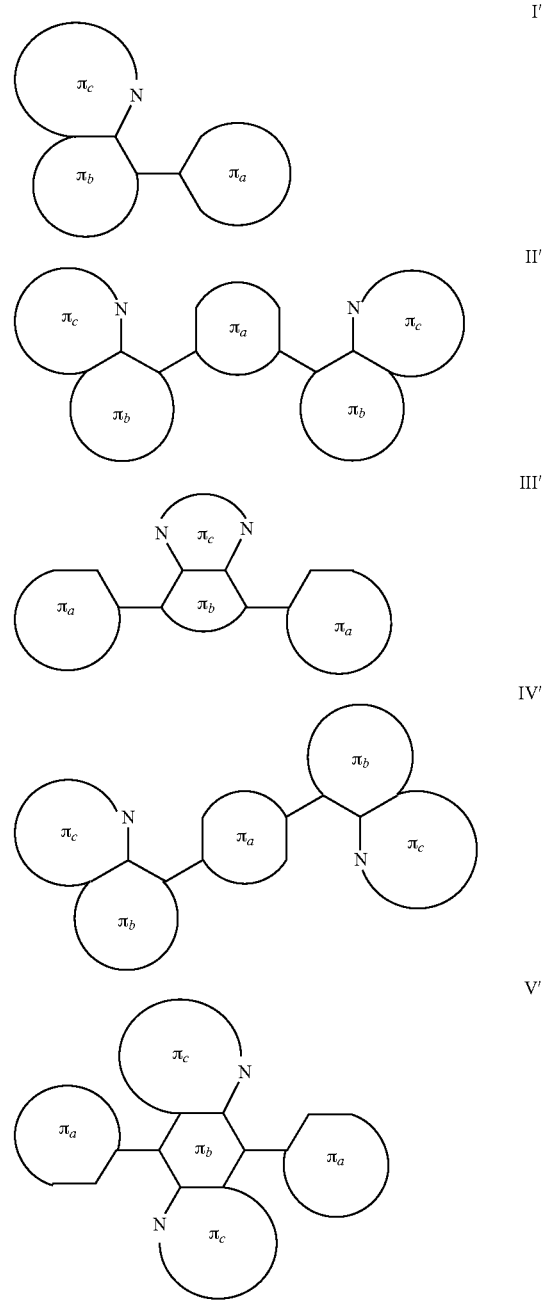

wherein moieties $\pi_a$, $\pi_b$ and $\pi_c$ are independently as defined in claim 1; and each X is selected from the group consisting of Cl, Br, aryl and heteroaryl;

b) reacting the product of step a) with a weak nucleophile in the presence or absence of a halophilic Lewis acid; and c) performing one or more subsequent steps on the product of step b) to functionalise the boron atom with or more $R_1$, $R_2$, $R_3$ and $R_4$ groups as defined in claim 1.

15. The method of claim 14, wherein the weak nucleophile is 2,4,6-tri-tert-butylpyridine.

16. The method of claim 14, wherein each X is selected from the group consisting of Cl and Br, and the halophilic Lewis acid is a halophilic main group Lewis acid.

17. The method of claim 14 wherein the reaction of step b) is additionally performed in the presence of a chloride donor.

18. The method of claim 14, further comprising the step d) of linking the product of step c) with one or more other moieties of formulae (I)-(V).

19. A method of preparing a compound comprising one or more moieties of formula (I) as claimed in claim 1, the method comprising the steps of:

a) reacting a compound comprising one or more moieties of formula (I') shown below with a reagent $BX_3$:

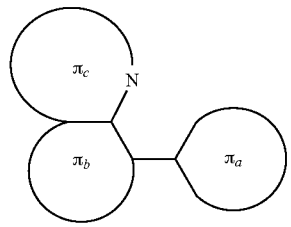

I' wherein moieties $\pi_a$, $\pi_b$ and $\pi_c$ are independently as defined in claim 1; and each X is selected from the group consisting of Cl, Br, aryl and heteroaryl; and b) performing one or more subsequent steps on the product of step b) to functionalise the boron atom with or more $R_1$, $R_2$, $R_3$ and $R_4$ groups as defined in claim 1.

20. The method of claim 19, furthering comprising the step c) of linking the product of step b) with one or more other moieties of formulae (I)-(V).

21. The method claim 14, wherein the compound comprising one or more moieties of formulae (I')-(V') is a polymer or oligomer.

22. A semiconducting material comprising a compound as claimed in claim 1.

23. An electro, optical or electro-optical device or component comprising a semiconducting material as claimed in claim 22.

* * * * *